[12] United States Patent
Broeckx et al.

(10) Patent No.: US 9,745,306 B2
(45) Date of Patent: *Aug. 29, 2017

(54) 2-((4-AMINO-3-(3-FLUORO-5-HYDROXYPHENYL)-1H-PYRAZOLO[3,4-D]PYRIMIDIN-1-YL)METHYL)-3-(2-(TRIFLUOROMETHYL)BENZYL)QUINAZOLIN-4(3H)-ONE DERIVATIVES AND THEIR USE AS PHOSPHOINOSITIDE 3-KINASE INHIBITORS

(71) Applicant: RESPIVERT LIMITED, Buckinghamshire (GB)

(72) Inventors: Rudy Laurent Maria Broeckx, Turnhout (BE); Alex Herman Copmans, Lille (BE); Alun John Smith, Nottingham (GB); David Michel Adrien Taddei, Nottingham (GB); Stuart Thomas Onions, Nottingham (GB)

(73) Assignee: Respivert Limited, Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/777,021

(22) PCT Filed: Mar. 14, 2014

(86) PCT No.: PCT/GB2014/050770
§ 371 (c)(1),
(2) Date: Sep. 15, 2015

(87) PCT Pub. No.: WO2014/140597
PCT Pub. Date: Sep. 18, 2014

(65) Prior Publication Data
US 2016/0039826 A1 Feb. 11, 2016

(30) Foreign Application Priority Data

Mar. 15, 2013 (EP) .................................... 13275070
Nov. 18, 2013 (EP) .................................... 13193372

(51) Int. Cl.
C07D 487/04 (2006.01)
A61K 31/519 (2006.01)
A61K 45/06 (2006.01)
(52) U.S. Cl.
CPC .......... *C07D 487/04* (2013.01); *A61K 31/519* (2013.01); *A61K 45/06* (2013.01)
(58) Field of Classification Search
CPC .............................. C07D 487/04; A61K 31/519
USPC ........................................ 544/262; 514/262.1
See application file for complete search history.

(56) References Cited

U.S. PATENT DOCUMENTS 9,227,977 B2 * 1/2016 Taddei ................ C07D 487/04
2007/0037805 A1 2/2007 Hayakawa et al.

FOREIGN PATENT DOCUMENTS

| EP | 1604981 B1 | 12/2005 |
| EP | 1661879 B1 | 5/2006 |
| EP | 1277738 B1 | 3/2011 |
| EP | 1790637 B1 | 1/2014 |
| WO | WO 00/42042 A2 | 7/2000 |
| WO | WO 00/42042 A3 | 7/2000 |
| WO | WO 01/81346 A2 | 11/2001 |
| WO | WO 01/81346 A3 | 11/2001 |
| WO | WO 01/83456 A1 | 11/2001 |
| WO | WO 02/051831 A1 | 7/2002 |
| WO | WO 03/006628 A2 | 1/2003 |
| WO | WO 03/006628 A3 | 1/2003 |
| WO | WO 03/007955 A2 | 1/2003 |

(Continued)

OTHER PUBLICATIONS

Knight et al., "A Pharmacological Map of the PI3-K Family Defines a Role for p110α in Insulin Signaling", Cell, vol. 125, 2006, pp. 733-747.

(Continued)

*Primary Examiner* — Deepak Rao
(74) *Attorney, Agent, or Firm* — Ada O. Wong

(57) ABSTRACT

The present invention relates inter alia to a compound of formula (I) and to compositions comprising the same and to the use of the compounds and to compositions of the compounds in treatment, for example in the treatment of inflammatory diseases, in particular respiratory inflammatory disease. The invention also extends to methods of making the said compounds.

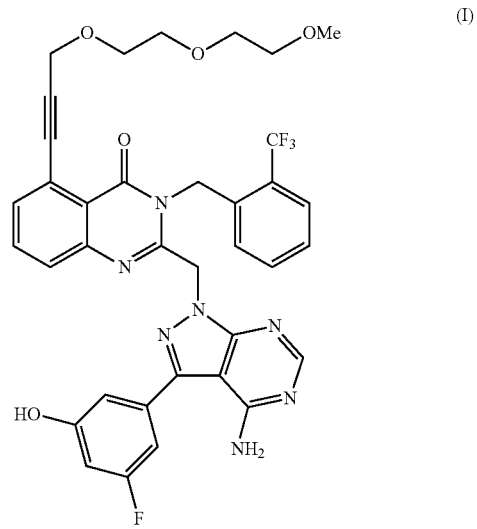

(I)

15 Claims, 17 Drawing Sheets

(56) References Cited

FOREIGN PATENT DOCUMENTS

| WO | WO 03/007955 A3 | 1/2003 |
|---|---|---|
| WO | WO 03/035075 A1 | 5/2003 |
| WO | WO 2004/037176 A2 | 5/2004 |
| WO | WO 2004/037176 A3 | 5/2004 |
| WO | WO 2004/080966 A1 | 9/2004 |
| WO | WO 2004/083174 A2 | 9/2004 |
| WO | WO 2004/083174 A3 | 9/2004 |
| WO | WO 2005/007085 A2 | 1/2005 |
| WO | WO 2005/007085 A3 | 1/2005 |
| WO | WO 2005/012221 A1 | 2/2005 |
| WO | WO 2005/016348 A1 | 2/2005 |
| WO | WO 2005/016349 A1 | 2/2005 |
| WO | WO 2005/067901 A2 | 7/2005 |
| WO | WO 2005/067901 A3 | 7/2005 |
| WO | WO 2005/112935 A1 | 12/2005 |
| WO | WO 2005/113554 A2 | 12/2005 |
| WO | WO 2005/113554 A3 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2006/030925 A1 | 3/2006 |
| WO | WO 2006/089106 A2 | 8/2006 |
| WO | WO 2006/089106 A3 | 8/2006 |
| WO | WO 2007/037805 A2 | 2/2007 |
| WO | WO 2007/037805 A3 | 2/2007 |
| WO | WO 2007/114926 A2 | 10/2007 |
| WO | WO 2007/114926 A3 | 10/2007 |
| WO | WO 2008/005262 A1 | 1/2008 |
| WO | WO 2008/058402 A1 | 5/2008 |
| WO | WO 2008/067219 A2 | 6/2008 |
| WO | WO 2008/067219 A3 | 6/2008 |
| WO | WO 2008/104077 A1 | 9/2008 |
| WO | WO 2008/127226 A2 | 10/2008 |
| WO | WO 2008/127226 A3 | 10/2008 |
| WO | WO 2008/140750 A1 | 11/2008 |
| WO | WO 2009/088986 A1 | 7/2009 |
| WO | WO 2009/088990 A1 | 7/2009 |
| WO | WO 2010/036380 A1 | 4/2010 |
| WO | WO 2010/059593 A1 | 5/2010 |
| WO | WO 2010/065923 A2 | 6/2010 |
| WO | WO 2010/065923 A3 | 6/2010 |
| WO | WO 2010/065932 A1 | 6/2010 |
| WO | WO 2010/111432 A1 | 9/2010 |
| WO | WO 2011/015037 A1 | 2/2011 |
| WO | WO 2011/048111 A1 | 4/2011 |
| WO | WO 2012/052753 A1 | 4/2012 |
| WO | WO 2013/136075 A1 | 9/2013 |
| WO | WO 2013/136076 A1 | 9/2013 |

OTHER PUBLICATIONS

Aspel et al., "Targeted polypharmacology: discovery of dual inhibitors of tyrosine and phosphoinositide kinases", Nature Chemical Biology, vol. 4, 2008, pp. 691-699.

Laplante, et al., "Assessing Atropisomer Axial Chemistry Chirality in Drug Discovery and Development", Journal of Medicinal Chemistry, 2011; vol. 54, pp. 7005-7011.

Clayden, et al., "The Challenge of Atropisomerism in Drug Discovery", Angew. Chem. Int. Ed. 2009; vol. 48, pp. 6398-6401.

Brana, et al., "Clinical development of phosphatidylinositol 3-kinase inhibitors for cancer treatment", BMC Medicine, 2012; vol. 10: 161, pp. 1-15.

Thomas, et al. "Inhibition of PI-3 kinase for treating respiratory disease: good idea or bad idea?", Current Opinion in Pharmacology, 2008; vol. 8, pp. 267-274.

Rameh, L.E. et al., "The Role of Phosphoinositide 3-Kinase Lipid Products in Cell Function", Journal Biol. Chem., 1999, 274:8347-8350.

Ito, K. et al., "Therapeutic Potential of Phosphatidylinositol 3-Kinase Inhibitors in Inflammatory Respiratory Disease", J. Pharmacol., Exp. Ther., 2007, 321:1-8.

Lee, K.S. et al., "Phosphoinositide 3-kinase-δ inhibitor reduces vascular permeability in a murine model of asthma", J. Allergy Clin Immunol., 2006, 118:403-409.

Lee, K.S. et al., "Inhibition of phosphoinositide 3-kinase δ attenuates allergic airway inflammation and hyperresponsiveness in murine asthma model", 3FASEB J. 2006, 20:455-65.

Sadhu, C. et al., "Selective role of PI3Kδ in neutrophil inflammatory responses", Biochem. Biophys, Res. Commun. 2003, 308:764-9.

Wymann, M.P. et al., "Phosphoinositide 3-kinase γ: a key modulator in inflammation and allergy", Biochem. Soc. Trans., 2003, 31:275-80.

Lim, D. H. et al., "PI3K-γ-deficient mice have reduced levels of allergen-induced eosinophilic inflammation and airway remodeling", Am. J. Physiol. Lung Cell. Mol. Physiol., 2009, 296(2): L210-L219.

Jiang, H. et al., "Targeting Phosphoinositide 3-Kinase γ in Airway Smooth Muscle Cells to Suppress Interleukin-13-Induced Mouse Airway Hyperresponsiveness", J. Pharmacol., Exp. Ther., 2012, 342(2):305-11.

Doukas, J., et al., "Aerosolized Phosphoinositide 3-Kinase γ/δ Inhibitor TG100-115 [3-[2,4]Diamino-6-(3-hydroxyphenyl)pteridin-7-yl]phenol] as a therapeutic Candidate for Asthma and Chronic Obstrutive Pulmonary Disease", J. Pharmacol. Exp. Ther, 2009, 328:758-765.

Williams, O. et al., "Discovery of Dual Inhibitors of the Immune Cell PI3Ks p110δ and p110γ: a Prototype for New Anti-inflammatory Drugs", Chem Biol., 2010, 17(2):123-34.

To, Y. et al., "Targeting Phosphoinositide-3-Kinase-δ with Theophylline Reverses Corticosteroid Insensitivity in Chronic Obstructive Pulmonary Diseases", Am. J. Respir. Crit. Care Med., 2010, 182:897-904.

Medicherla, S., et al., "p38γ-Selective Mitogen-Activated Protein Kinase Inhibitor SD-282 Reduces Inflammation in a subchronic Model of Tobacco Smoke-Induced Airway Inflammation", J. Pharmacol. Exp. Ther. 2008, 324:921-9.

* cited by examiner

The effects of treatment with compound (I) or compound A on poly-I:C-induced neutrophil accumulation in mouse airways.

NT: non treatment, in: intranasal

Comparison of the inhibitory potencies of compound (I) with compound A on poly-I:C-induced neutrophil accumulation in mouse airways The effect of treatment with compound (I) or compound A on cigarette smoke-induced macrophage accumulation in murine BALF.

The effect of treatment with compound (I) or compound A on cigarette smoke-induced neutrophil accumulation in murine BALF.

2-((4-AMINO-3-(3-FLUORO-5-HYDROXYPHENYL)-1H-PYRAZOLO[3,4-D]PYRIMIDIN-1-YL)METHYL)-3-(2-(TRIFLUOROMETHYL)BENZYL)QUINAZOLIN-4(3H)-ONE DERIVATIVES AND THEIR USE AS PHOSPHOINOSITIDE 3-KINASE INHIBITORS

CROSS-REFERENCE TO RELATED APPLICATIONS

This application is a national phase entry of International Application Number PCT/GB2014/050770, filed 14 Mar. 2014, which claims the benefit of European Application Numbers 13275070.4, filed 15 Mar. 2013 and 13193372.3 filed 18 Nov. 2013. The entire contents of each of the aforesaid applications are incorporated herein by reference in their entirety.

FIELD OF THE INVENTION

The invention relates to compounds that inhibit phosphoinositide 3-kinases, (PI3 kinases, PI3K). In particular the disclosure relates to compounds that inhibit the PI3K delta sub-type and, in addition, the gamma sub-type thereof, and to their use in therapy, including in pharmaceutical combinations, especially in the treatment of inflammatory diseases, including inflammatory diseases of the lung, such as COPD and asthma. The invention also extends to methods of preparing the said compounds and to pharmaceutical compositions comprising the same.

BACKGROUND OF THE INVENTION

Lipid kinases catalyse the phosphorylation of lipids to produce species involved in the regulation of a wide range of physiological processes, including cellular migration and adhesion. The PI3 kinases (PI3K) are membrane associated proteins and belong to the class of enzymes which catalyse the phosphorylation of lipids which are themselves associated with cell membranes. The PI3K delta isozyme (PI3K δ) is one of four isoforms of type I PI3K kinases responsible for generating various 3'-phosphorylated phosphoinositides, that mediate cellular signalling and have been implicated in inflammation, growth factor signalling, malignant transformation and immunity [See Review by Rameh, L. E. and Cantley, L. C. *J. Biol. Chem.*, 1999, 274:8347-8350.].

The involvement of PI3K in controlling inflammation has been confirmed in several models using pan-active PI3K inhibitors, such as LY-294002 and Wortmannin [Ito, K. et al., *J Pharmacol. Exp. Ther.*, 2007, 321:1-8.]. Recent studies have been conducted using either selective PI3K inhibitors or in knock-out mice lacking a specific enzyme isoform as described below. These studies have demonstrated the role of pathways controlled by PI3K enzymes in inflammation. The PI3K δ selective inhibitor IC-87114 was found to inhibit airways hyper-responsiveness, IgE release, pro-inflammatory cytokine expression, inflammatory cell accumulation into the lung and vascular permeability in ovalbumin-sensitized, ovalbumin-challenged mice [Lee, K. S. et al., *J. Allergy Clin. Immunol.*, 2006, 118:403-409 and Lee, K. S. et al., *FASEB J.*, 2006, 20:455-65.]. In addition, IC-87114 lowered neutrophil accumulation in the lungs of mice and neutrophil function, stimulated by TNFα [Sadhu, C. et al., *Biochem. Biophys. Res. Commun.*, 2003, 308:764-9].

The PI3K δ isoform is activated by insulin and other growth factors, as well as by G-protein coupled protein signaling and inflammatory cytokines. Furthermore, studies using knockout mice revealed that activation of PI3K gamma (PI3K γ) may be important in the pathogenesis of asthma. For example, murine mast cell responses are exacerbated in vitro and in vivo by autocrine signals which require functional PI3K γ. Mice that lacked PI3K γ did not exhibit edema when challenged by passive systemic anaphylaxis [Wymann M. P. et al., *Biochem. Soc. Trans.*, 2003, 31:275-80.]. Thus PI3K γ relays inflammatory signals through various G-protein coupled receptors (GPCRs), especially by controlling mast cell function. Eosinophil accumulation in ovalbumin sensitised and challenged mice was also reported to be inhibited in these PI3K γ-deficient mice, as compared with wild-type animals [Lim D. H. et al., *Am. J. Physiol. Lung Cell. Mol. Physiol.*, 2009, 296(2):L210-L219]. Finally, treatment with a PI3K γ inhibitor attenuated IL-13-augmented airway contractility of lung slices [Jiang H. et al., *J. Pharmacol. Exp. Ther.*, 2012, 342(2):305-11].

Recently the PI3K dual δ/γ inhibitor TG100-115 was reported to inhibit pulmonary eosinophilia and decrease interleukin-13 levels, mucin accumulation and airways hyper-responsiveness in a murine model, when administered by aerosolisation. The same authors also reported that the compound was able to inhibit pulmonary neutrophilia elicited by either LPS or cigarette smoke [Doukas, J. et al., *J Pharmacol. Exp. Ther.*, 2009, 328:758-765.]. Other small molecule inhibitors of PI3K δ and γ were reported to produce superior inhibition of LPS induced TNFα production and T cell activation when compared with PI3K δ selective inhibitors [Williams O. et al., *Chem Biol.*, 2010, 17(2):123-34.].

Since it is also activated by oxidative stress, the PI3K δ isoform is likely to be relevant as a target for therapeutic intervention in those diseases where a high level of oxidative stress is implicated. Downstream mediators of the PI3K signal transduction pathway include Akt (a serine/threonine protein kinase) and the mammalian target of rapamycin, the enzyme mTOR. Recent work has suggested that activation of PI3K δ, leading to phosphorylation of Akt, is able to induce a state of corticosteroid resistance in otherwise corticosteroid-sensitive cells [To, Y. et al., *Am. J. Respir. Crit. Care Med.*, 2010, 182:897-904.]. These observations have led to the hypothesis that this signalling cascade could be one mechanism responsible for the corticosteroid-insensitivity of inflammation observed in the lungs of patients suffering from COPD, as well as in those asthmatics who smoke, thereby subjecting their lungs to increased oxidative stress. Indeed, theophylline, a compound used in the treatment of both COPD and asthma, has been suggested to reverse steroid insensitivity through mechanisms involving interaction with pathways controlled by PI3 kinase δ [To, Y. et al., *Am. J. Respir. Crit. Care Med.*, 2010, 182:897-904.].

At present the mainstay of treatment for both asthma and COPD is inhaled therapy, using a combination of corticosteroids, muscarinic antagonists and $\beta_2$-agonists, as judged clinically appropriate. One way of addressing the unmet medical needs in COPD and asthma is to identify new inhaled medicines, which have the potential to provide significant benefit when used either as a monotherapy or in combination with one or more medicaments from these three pharmacological classes. Therefore, there remains a need to identify and develop isoform selective PI3K inhibitors which have the potential to provide enhanced therapeutic efficacy in asthma, COPD and other inflammatory diseases.

WO 2012/052753 discloses: 6-(2-((4-amino-3-(3-hydroxyphenyl)-1H-pyrazolo[3,4-d]pyrimidin-1-yl)methyl)-

3-(2-chlorobenzyl)-4-oxo-3,4-dihydroquinazolin-5-yl)-N,N-bis(2-methoxyethyl)hex-5-ynamide, referred to herein as prior art Compound A.

WO 2011/048111 discloses certain 3-benzyl-5-alkynyl-quinazolin-4(3H)-ones

A compound example disclosed therein is 2-((4-amino-3-(3-hydroxyphenyl)-1H-pyrazolo[3,4-d]pyrimidin-1)methyl)-3-(2-fluorobenzyl)-5-(3-(2-(2-methoxyethoxy)ethoxy)prop-1-ynyl)quinazolin-4(3H)-one, referred to herein as Example 50.

Neither of these prior art compounds possess the same advantageous profile of the compound of formula (I) described herein.

SUMMARY OF THE INVENTION

According to the invention, there is provided a compound of formula (I):

(I)

or a pharmaceutically acceptable salt thereof, including all stereoisomers, tautomers and isotopic derivatives thereof.

In another aspect of the invention there is provided a compound of formula (I) in solid crystalline form.

In a further aspect of the invention there is provided a compound of formula (I) in the form of its Form 2 crystalline polymorph (sometimes referred to herein as "the Form 2 crystalline polymorph").

In a further aspect of the invention there is provided a compound of formula (I) in the form of its Form 3 crystalline polymorph (sometimes referred to herein as "the Form 3 crystalline polymorph").

A comparison of the in vitro profiles of prior art compounds Compound A and Example 50 with the compound of the present disclosure is presented herein below (see Table 5 in Experimental Section). The compound of the present invention is a particularly potent dual PI3K δ/γ isoform inhibitor, a pharmacological feature that confers upon it a distinct and advantageous therapeutic profile over compounds disclosed previously. This aspect of the invention is particularly evident from the in vivo profile of the compound of formula (I) in animal models that are predictors of therapeutic efficacy and clinical benefit in pulmonary inflammation (see Tables 8-12 in the Experimental Section).

In one embodiment the compound of the present disclosure has improved inhibitory activity over prior art compounds when compared in an in vivo assay that measures the ability of a test substance to inhibit poly IC induced influx of neutrophils into mouse lung. The improvement demonstrated may be 1, 2, 3, 4, 5, 6, 7, 8, 9 or 10 fold (or more) over known compounds, previously disclosed in the art.

Activity in the in vivo poly IC assay is considered indicative of the potential of the compound of the present invention to inhibit virus-induced exacerbations in patients suffering with asthma or with COPD. It is thought that viral infections induce disease exacerbations by worsening inflammation in the lungs of patients and by generating a steroid resistant phenotype. Poly IC stimulates one of the mechanisms through which viruses are pro-inflammatory.

The drug-like properties of the compound described herein, including its intrinsic physical and chemical stability, solubility profile, and especially its distinctive biological activity render the said compound particularly suitable for use as a pharmaceutical agent and in particular for the treatment of inflammatory mediated diseases.

DETAILED DESCRIPTION OF THE INVENTION

Figure 1A:
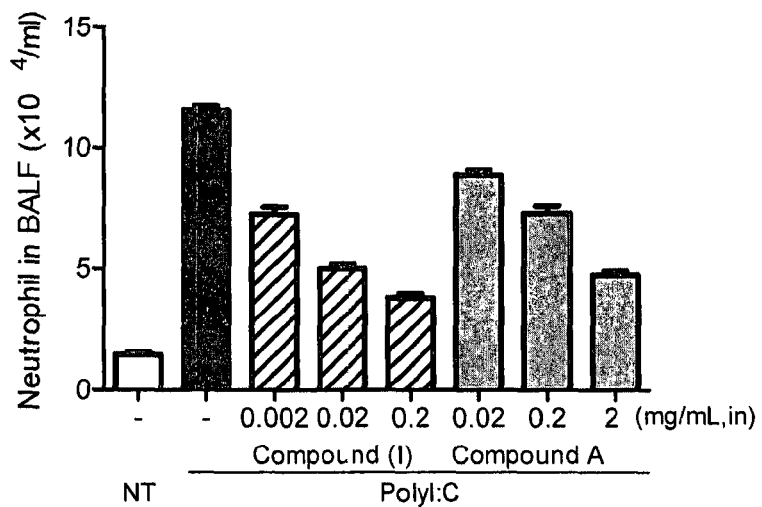
FIG. 1a: is a bar graph representing the effects of treatment with compound (I) or compound A on poly-I:C-induced neutrophil accumulation in mouse airways.

The term inhibitor as employed herein is intended to refer to a compound that reduces (for example by at least 10%, 20%, 30%, 40%, 50% or more) or eliminates the biological activity of the target protein, for example the PI3K δ isozyme, in an in vitro enzyme assay.

The term delta/gamma (δ/γ) inhibitor as employed herein is intended to refer to the fact that the compound inhibits, to some degree, inhibitory activity at both enzyme isoforms although not necessarily to the same extent.

The compound of the present disclosure is active in cell based screening systems and thereby demonstrates that it possesses suitable properties for penetrating cells and is able to exert intracellular pharmacological effects (see Table 6 and Table 7 in the Experimental Section).

The compound of the present disclosure has therapeutically relevant and desirable pharmaceutical properties for a medicament, for example physico-chemical features including adequate chemical and photostability, an appropriate solubility profile and potent activity.

In one embodiment there is provided a pharmaceutically acceptable salt of the compound of the invention.

In one embodiment there is provided a pharmaceutically acceptable acid addition salt of the compound of the invention.

The pharmaceutically acceptable acid addition salts referred to hereinabove are meant to comprise the therapeutically active, non-toxic, acid addition salts that the compounds of formula (I) are able to form. These pharmaceutically acceptable acid addition salts can conveniently be obtained by treating the free base form of the compound of formula (I) with an example of such appropriate acids. Examples of appropriate acids include, for example, inorganic acids such as hydrochloric acid, hydrobromic acid, and sulfuric, and phosphoric acids and the like; or organic acids such as, for example, acetic, propanoic, hydroxyacetic, lactic, malonic, succinic, maleic, fumaric, malic, tartaric, citric, methanesulfonic, para-toluenesulfonic, cyclamic, salicylic, para-aminosalicylic, pamoic acid and the like. A further example of an appropriate acid is benzenesulfonic acid.

Examples of salts of the compound of formula (I) include all pharmaceutically acceptable salts, such as, without limitation, acid addition salts of mineral acids such as HCl and HBr salts and addition salts of organic acids such as a methanesulfonic acid salt. Further examples include sulphuric acid salts and phosphoric acid salts.

In another embodiment, there is provided a pharmaceutically acceptable salt of the compound of the invention formed by reacting the compound of formula (I) with a suitable base. Examples of appropriate bases include, for example sodium hydroxide, potassium hydroxide, magnesium hydroxide, calcium hydroxide, L-arginine, choline and L-lysine.

In one embodiment there is provided 2-((4-amino-3-(3-fluoro-5-hydroxyphenyl)-1H-pyrazolo[3,4-d]pyrimidin-1-yl)methyl)-5-(3-(2-(2-methoxyethoxy)ethoxy)prop-1-yn-1-yl)-3-(2-(trifluoromethyl)benzyl)quinazolin-4(3H)-one as the free base.

The invention also extends to solvates of the compounds disclosed herein. Examples of solvates include hydrates.

The compounds of the disclosure include those where the atom specified is a naturally occurring or non-naturally occurring isotope. In one embodiment the isotope is a stable isotope. Thus the compounds of the disclosure include, for example those containing one or more deuterium atoms in place of hydrogen atoms and the like.

The disclosure also extends to all polymorphic forms of the compounds herein defined.

The compounds of formula (I) may be conveniently prepared by a process comprising reacting a compound of formula (II):

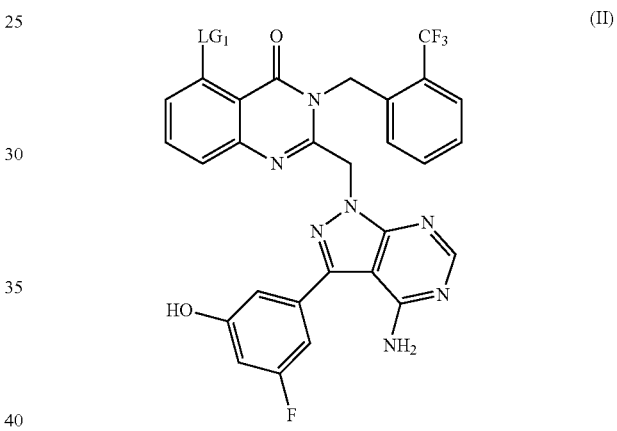

or a protected derivate thereof wherein $LG_1$ represents a leaving group such as halo, in particular bromo, with a compound of formula (III):

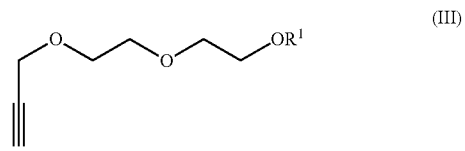

in the presence of a suitable catalyst and an organic base and in a polar aprotic solvent under an inert atmosphere. Suitable catalysts include palladium catalysts such as bis(triphenylphosphine)palladium (II) dichloride, in the presence of copper iodide. A suitable polar aprotic solvent for this transformation is DMF and a suitable inert atmosphere is nitrogen.

For synthetic processes in which the compound of formula (II) is a protected derivative, the compound of formula (I) is revealed by an appropriate deprotection step, as is well known and practiced in the art. For example when the phenol present in the compounds of formula (I) is protected with a silyl group, for example with a tert-butyldimethylsilyl group the deprotection step can be effected by treatment with a reagent such as tetrabutylammonium fluoride in the presence of a polar aprotic solvent such as DMF. The reaction may be performed at a reduced temperature, such as at 0° C.

Compounds of formula (II) can be prepared by reacting a compound of formula (IV):

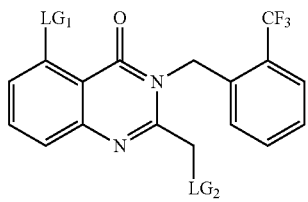

(IV)

or a protected derivative thereof, wherein $LG_1$ is a leaving group, as defined hereinabove for compounds of formula (II) and $LG_2$ is also a leaving group such as halo, for example a halogen atom and suitably a chlorine, with a compound of formula (V):

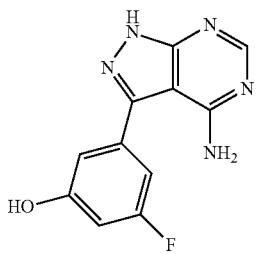

(V)

or a protected derivative thereof, in the presence of a base and in a polar aprotic solvent.

Suitable bases for this transformation include potassium carbonate and a suitable polar aprotic solvent is DMF.

Synthetic processes include those for which it is deemed advantageous to protect the phenolic hydroxyl of the compound of formula (VII) during the coupling step and suitable protected derivatives include a tertbutyldimethylsilyl ether and a tert-butyl ether.

Alternatively compounds of formula (II) can be prepared by reacting a compound of formula (VI):

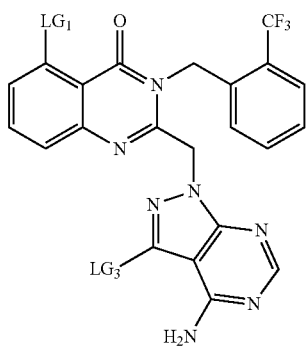

(VI)

or a protected derivative thereof, wherein $LG_1$, is as defined above for compounds of formula (II) and $LG_3$ represents a leaving group such as halo, in particular iodo, with a compound of formula (VII):

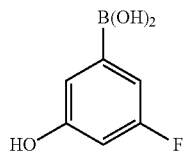

(VII)

or a protected derivate thereof, in the presence of a suitable noble metal catalyst, an inorganic base and in a polar protic solvent, under an inert atmosphere; followed, where appropriate, by deprotection.

A suitable catalyst is tetrakis(triphenylphosphine)palladium(0).

A suitable inorganic base is sodium carbonate and a suitable polar protic solvent is ethanol.

The reaction may be performed at an elevated temperature, for example at 85° C. for an extended period such as, for example, 3 days before cooling to RT.

Protecting groups may be advantageous to mask chemically sensitive groups during one or more of the reaction sequences described above, to ensure that one or more of the processes are efficient. Thus if desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; $4^{th}$ Rev Ed., 2006, ISBN-10: 0471697540.

Novel intermediates are claimed as an aspect of the invention.

Advantageously, compound (I) of the present invention does not exhibit atropisomerism.

Figure 3:
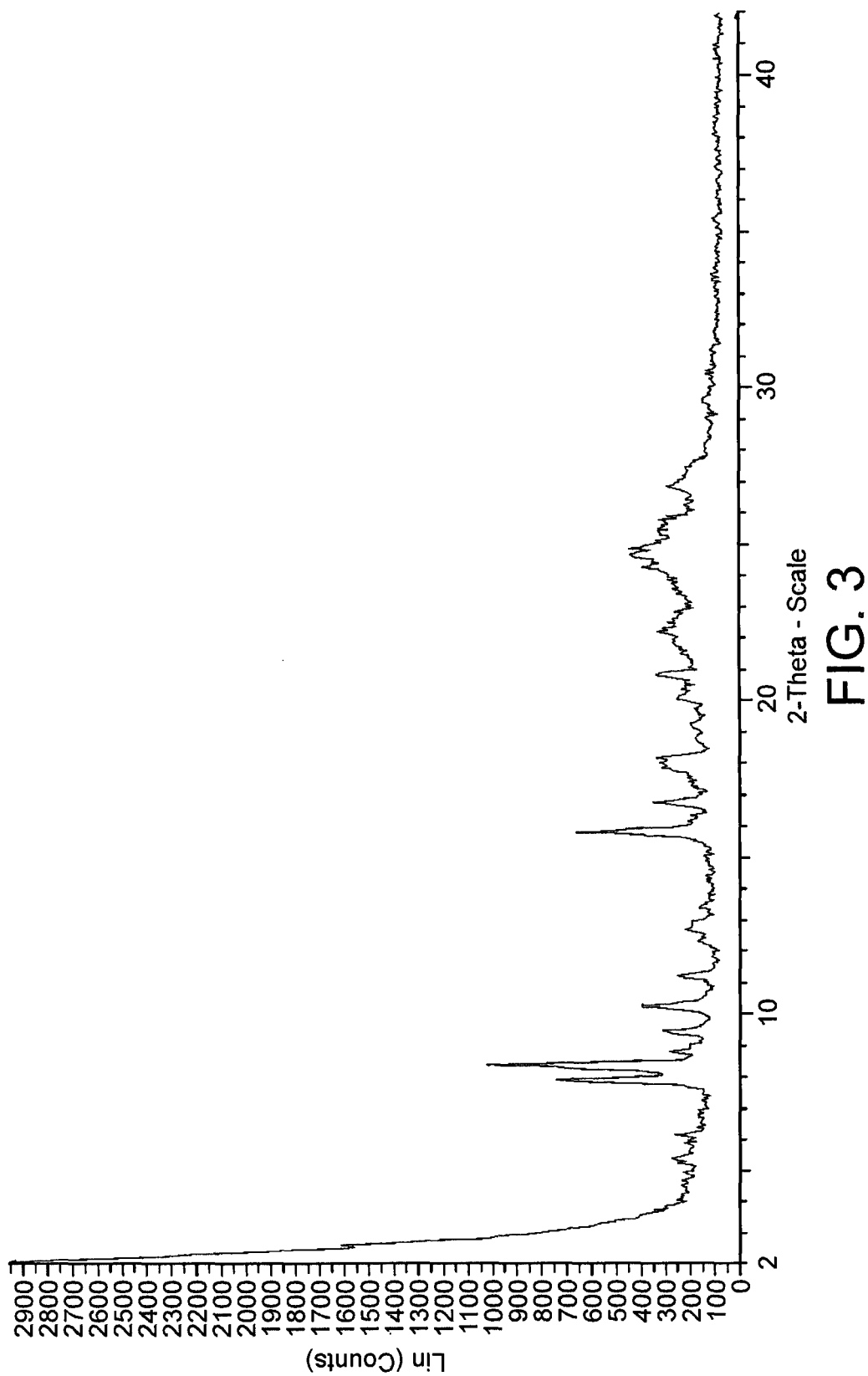
FIG. 3: is an X-ray powder diffraction (XRPD) pattern acquired from a sample of the Form 1 crystalline polymorph (see Example 2).

Compound (I) prepared according to Example 2 of this disclosure is produced as the Form 1 crystalline polymorph. The Form 1 crystalline polymorph is characterised by an XRPD pattern substantially as shown in FIG. 3.

The thermal behaviour of a sample of the Form 1 crystalline polymorph was found to be complex. As discussed in Example 2 and illustrated in the DSC analysis shown in FIG. 4 (bottom plot), a sample of the Form 1 crystalline polymorph underwent a number of events on heating, and ultimately transformed into different crystalline polymorph—referred to herein at the Form 2 crystalline polymorph.

The Form 2 crystalline polymorph was found to be anhydrous and melted with decomposition at about 190° C. (peak maximum). Slurrying experiments performed on the Form 1 crystalline polymorph lead to the formation of the Form 2 crystalline polymorph for most solvents, although an anhydrous crystalline polymorph—referred to herein as the Form 3 crystalline polymorph, was obtained by slurrying Form 1 crystalline polymorph in dichloromethane. The Form 3 crystalline polymorph was found to be anhydrous and melted with decomposition at about 186° C. (peak maximum; see Example 8). A number of pseudopolymorphs of compound (I) (Form 4, 5, 6 and 7 pseudopolymorphs) were also obtained from slurrying the Form 1 crystalline polymorph or compound (I) in amorphous form with THF, 1,4-dioxane, 10% water/acetonitrile or 10% water/acetone (see Examples 9 to 12).

Of the seven different polymorphic and pseudopolymorphic forms of compound (I), the Form 2 and Form 3 crystalline polymorphs had the most promising solid state properties, with the Form 2 crystalline polymorph being most favourable due to having the higher melting point.

Competitive slurry experiments were performed using a 50/50 mixture of the Form 2 and Form 3 crystalline polymorphs in various solvents at various temperatures (see Example 13). All experiments yielded the Form 2 crystalline polymorph, confirming that this is the more thermodynamically stable form. Given that it is desirable to minimise the risk of polymorphic form inter-conversion during storing of the compound and manufacture of pharmaceutical products containing the compound, or during the lifetime of such a product after manufacture, the Form 2 crystalline polymorph has advantages over the Form 3 crystalline polymorph and other polymorphic forms of compound (I).

Suitably, the Form 2 crystalline polymorph is prepared by crystallizing compound (I) from a solution in 1-propanol. Exemplary procedures using 1-propanol are described in Example 3, with and without seeding.

The Form 2 crystalline polymorph may also be prepared by slurrying the Form 1 crystalline polymorph in methanol, ethanol, 2-propanol, 1-propanol, acetone, ethyl acetate, acetonitrile, toluene, isopropylacetate, TBME, 2-butanone, DMSO, diethyl ether, MIBK, heptane, nitromethane, 10% water/ethanol, 10% water/acetonitrile or 10% water/2-propanol.

Alternatively, the Form 2 crystalline polymorph may be prepared by slurrying compound (I) in amorphous form in methanol, ethanol, 2-propanol, 1-propanol, acetone, ethyl acetate, acetonitrile, toluene, isopropylacetate, TBME, 2-butanone, DMSO, diethyl ether, MIBK, nitromethane, 10% water/ethanol or 10% water/2-propanol.

The inventors' experimentation has shown that slurrying compound (I) in amorphous form, in dichloromethane, leads to the formation of the Form 3 crystalline polymorph. Therefore use of dichloromethane in crystallisation conditions intended to form the Form 2 crystalline polymorph should be avoided.

The inventors' experimentation has shown that slurrying compound (I) in amorphous form or the Form 1 crystalline polymorph, in THF, leads to the formation of the Form 4 pseudopolymorph. Therefore use of THF in crystallisation conditions intended to form the Form 2 crystalline polymorph should be avoided.

The inventors' experimentation has shown that slurrying compound (I) in amorphous form or the Form 1 crystalline polymorph, in 1,4-dioxane, leads to the formation of the Form 5 pseudopolymorph. Therefore use of 1,4-dioxane in crystallisation conditions intended to form the Form 2 crystalline polymorph should be avoided.

The inventors' experimentation has shown that slurrying compound (I) in amorphous form in 10% water/acetonitrile leads to the formation of the Form 6 pseudopolymorph. Therefore use of 10% water/acetonitrile in crystallisation conditions intended to form the Form 2 crystalline polymorph from compound (I) in amorphous form should be avoided.

The inventors' experimentation has shown that slurrying compound (I) in amorphous form in 10% water/acetone leads to the formation of the Form 7 pseudopolymorph. Therefore use of 10% water/acetone in crystallisation conditions intended to form the Form 2 crystalline polymorph from compound (I) in amorphous form should be avoided.

Figure 5:
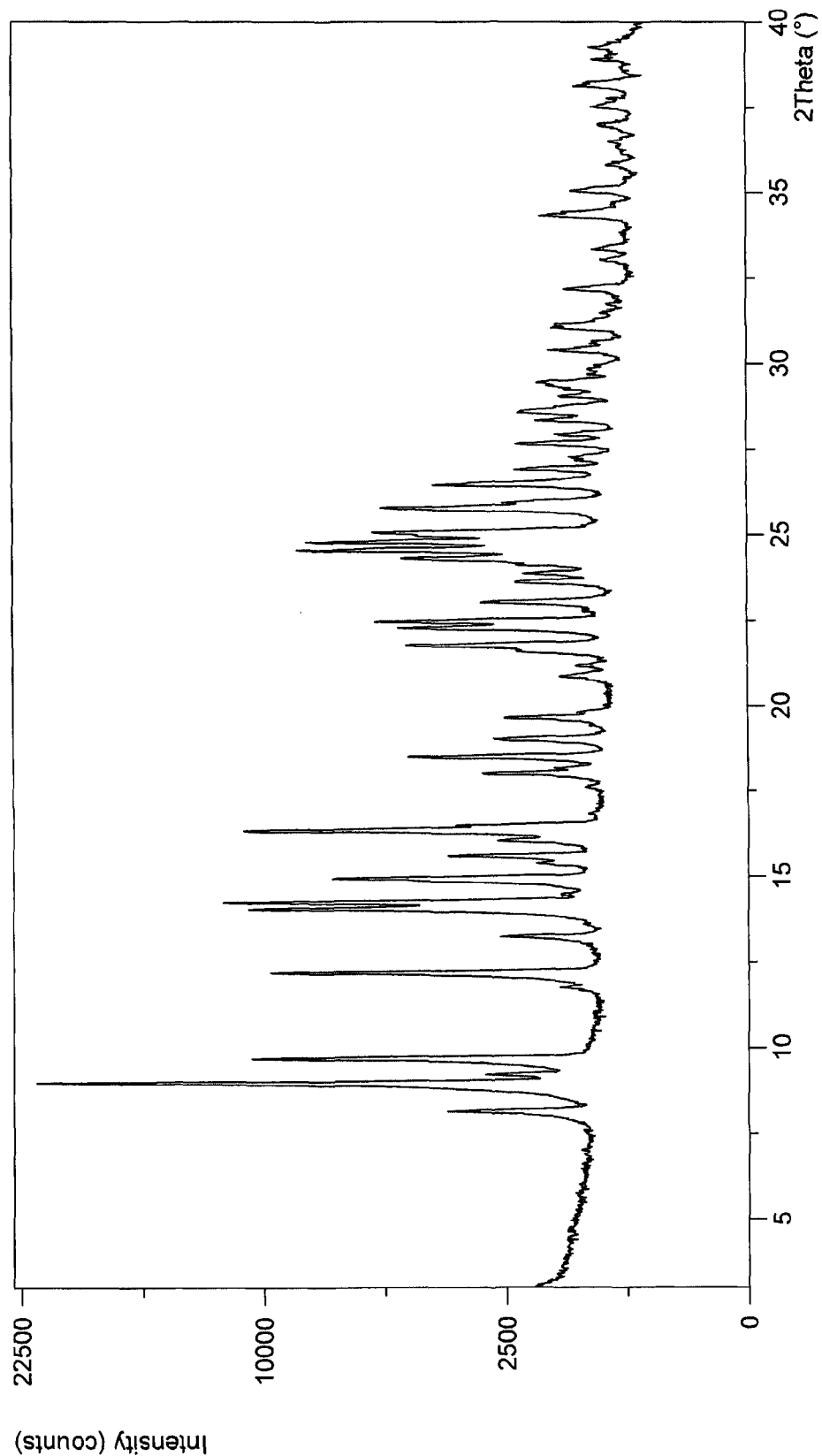
FIG. 5: is an XRPD pattern acquired from a sample of the Form 2 crystalline polymorph (see Example 4).

The Form 2 crystalline polymorph is characterised by an XRPD pattern substantially as shown in FIG. 5. This pattern has major peaks at positions 8.2, 9.0, 9.2, 9.7, 12.2, 14.1, 14.3, 15.0, 16.4, 18.0, 18.5, 19.0, 19.6, 21.8, 22.3, 22.5, 24.3, 24.5, 24.8, 25.1 and 25.8 (±0.2 degrees, 2-theta values). It is typical that at least three (for example three, four, five, six, seven, eight, nine, ten, eleven, twelve, thirteen, fourteen, fifteen, sixteen, seventeen, eighteen, nineteen, twenty or all twenty one) of these are observable in the resulting XRPD pattern. The peaks at 9.7, 12.2, 14.1 and 14.3 are particularly characteristic for the Form 2 crystalline polymorph and therefore it is typical that at least one (for example one, two, three, or all four) of these peaks are observable in the XRPD pattern.

Figure 12:
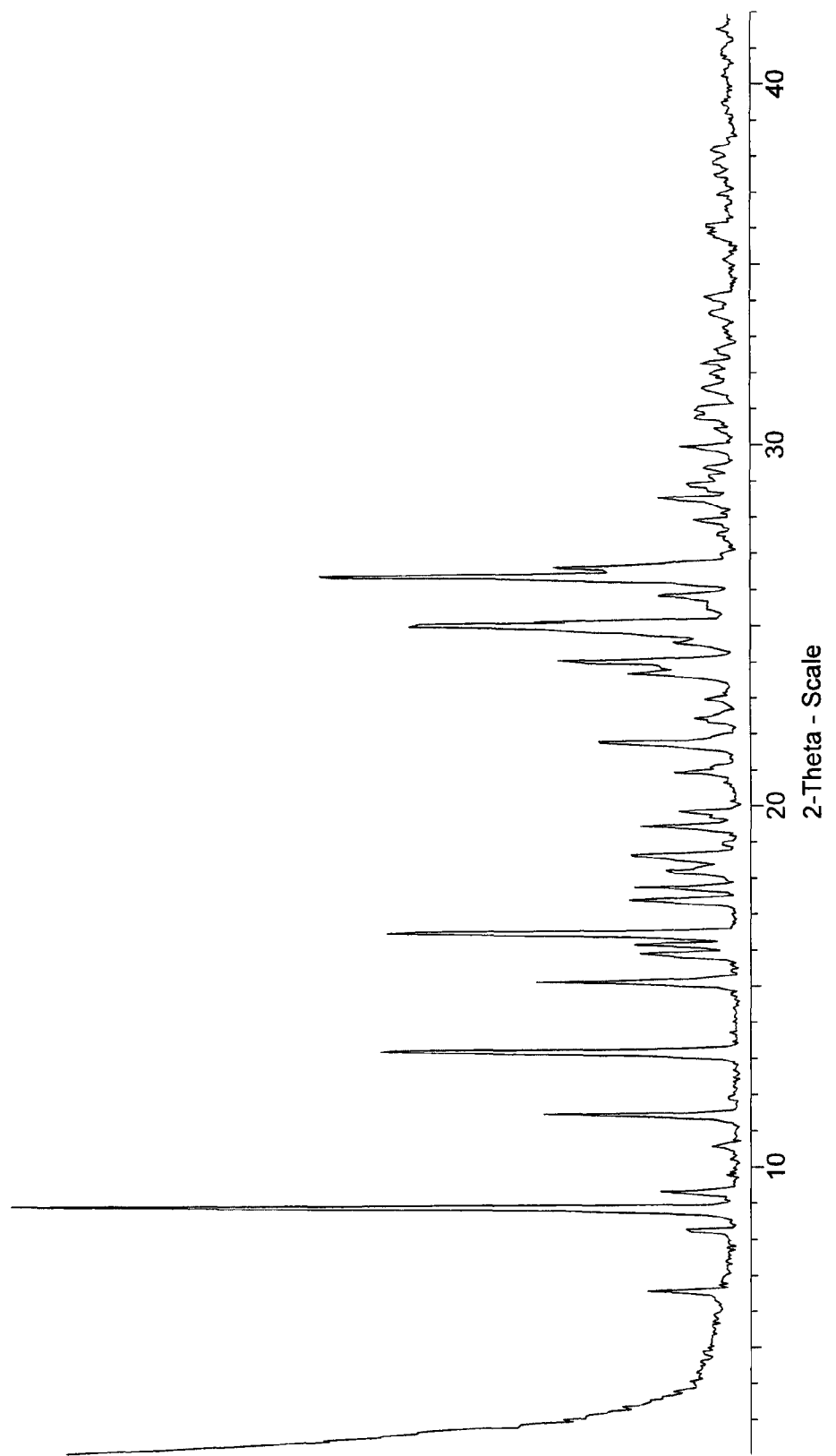
FIG. 12: is an XRPD pattern acquired from a sample of the Form 3 crystalline polymorph (see Example 8).

The Form 3 crystalline polymorph is characterised by an XRPD pattern substantially as shown in FIG. 12.

Figure 17:
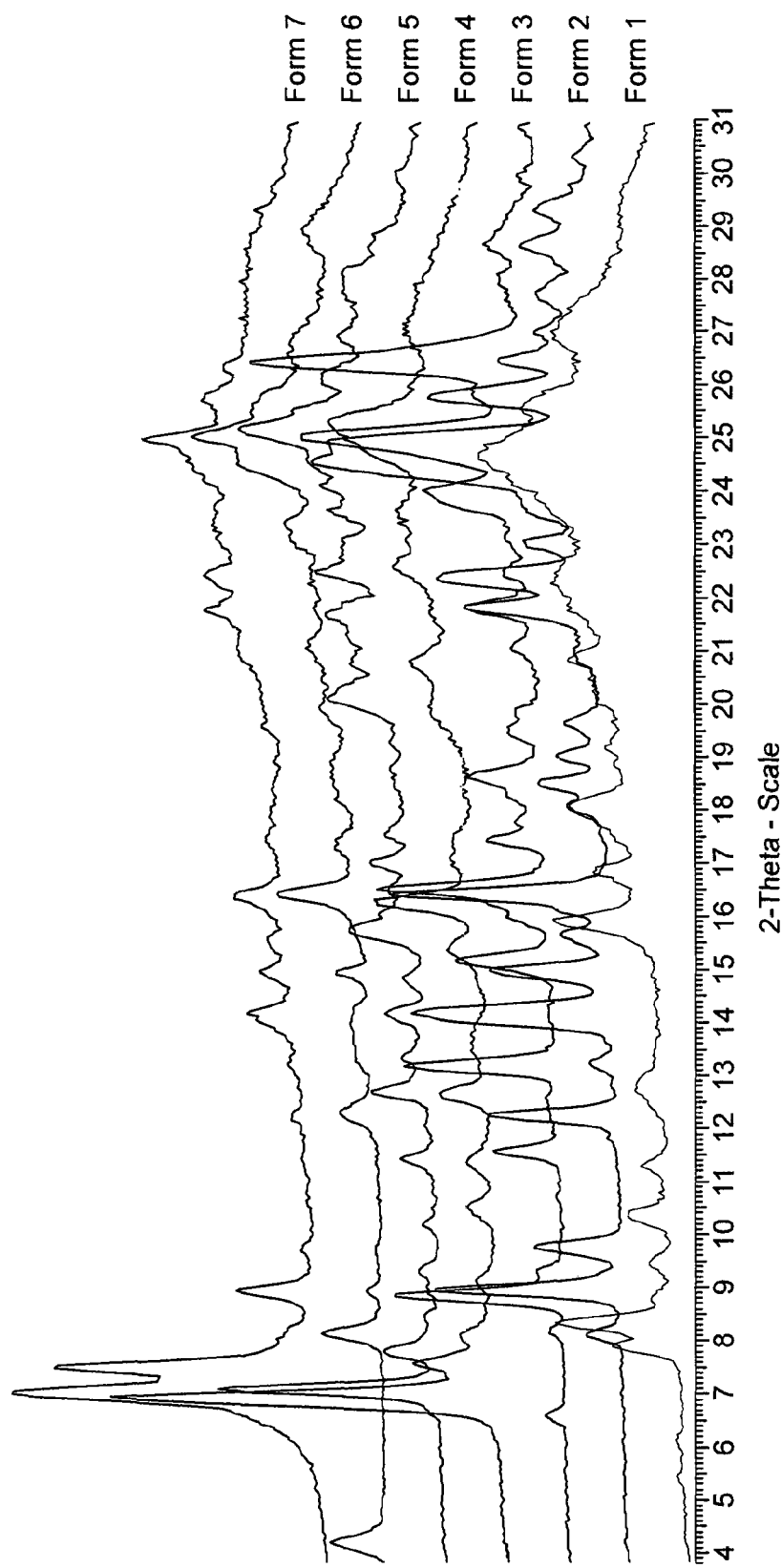
FIG. 17: shows an overlay of XRPD patterns acquired from samples of Form 7 (top plot), Form 6, Form 5, Form 4, Form 3, Form 2 and Form 1 (bottom plot) (see Examples 9 to 12).

The Form 4 pseudopolymorph is characterised by an XRPD pattern substantially as shown in FIG. 17.

The Form 5 pseudopolymorph is characterised by an XRPD pattern substantially as shown in FIG. 17.

The Form 6 pseudopolymorph is characterised by an XRPD pattern substantially as shown in FIG. 17.

The Form 7 pseudopolymorph is characterised by an XRPD pattern substantially as shown in FIG. 17.

In one aspect the compound is useful in treatment, for example COPD and/or asthma.

The PI3K compounds developed to date have typically been intended for oral administration. Typically this strategy involves the optimisation of a compound's pharmacokinetic profile in order to achieve an adequate duration of action. In this way a sufficiently high drug concentration is established and maintained between doses to provide continuous clinical benefit. An inevitable and frequently undesired consequence of this approach is that non-targeted body tissues, especially the liver and the gut, are likely to be exposed to pharmacologically active concentrations of the drug.

An alternative strategy is to design treatment regimens in which the drug is dosed directly to the inflamed organ (for example topical therapy). Although this approach is not suitable for treating all chronic inflammatory conditions, it has been extensively exploited in treating lung diseases (asthma, COPD, cystic fibrosis), skin lesions (atopic dermatitis and psoriasis), nasal diseases (allergic rhinitis), eye disease (allergic conjunctivitis) and gastrointestinal disorders (ulcerative colitis).

In topical therapy, the desired efficacy can sometimes be achieved by ensuring that the drug has a sustained duration of action and is retained predominantly in the target organ, thereby minimising the risks of systemic toxicity. Alternatively an appropriate formulation can be used which generates a "reservoir" of the active drug which is then available to sustain the desired effects. The first approach is exemplified in the use of the anticholinergic drug tiotropium bromide (Spiriva HandiHaler®), which is administered topically to the lung as a treatment for COPD. This compound has an exceptionally high affinity for its target receptor resulting in a very slow off rate (dissociation rate) and a consequent sustained duration of action.

There is provided according to one aspect of the present disclosure use of the compound of formula (I) or a pharmaceutical formulation containing it, as a PI3 kinase inhibitor, for example administered topically to the lung.

Thus in one embodiment the compound of the present disclosure is intended for use by topical administration to the lungs in order to maximise therapeutic benefit to patients whilst minimising the potential for undesirable systemic effects. It is therefore advantageous that the compound of formula (I) is rapidly metabolised once it has reached the general circulation and that the product(s) of turnover is/are less active than the parent molecule.

A likely principal product of first pass metabolism of the compound of formula (I) is the corresponding alcohol, compound (Ia), which would arise from O-demethylation, a metabolic process which is a common feature for structures of this chemotype. This possible metabolic product is significantly less active than the compound of formula (I) as a PI3K inhibitor at both the α and β subtypes (see Table 6 in the Experimental Section).

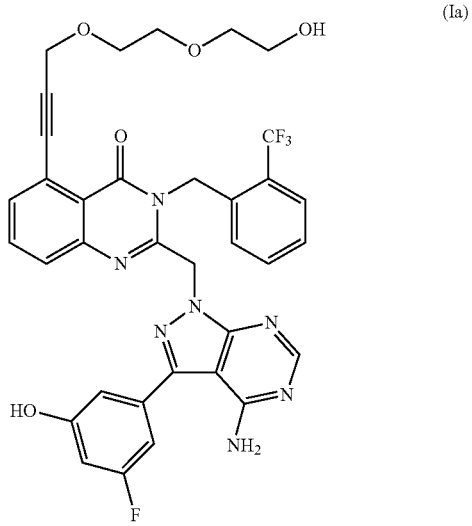 [SMILES: Nc1ncnc2c1c(-c1cc(O)cc(F)c1)nn2Cc1nc2cccc(C#CCOCCOCCO)c2c(=O)n1Cc1ccccc1C(F)(F)F]

(Ia)

Thus, in one aspect is provided a compound of formula (Ia) or a pharmaceutically acceptable salt thereof, including all stereoisomers, tautomers and isotopic derivatives thereof.

In one aspect of the disclosure the compound of the invention is particularly suitable for topical delivery, such as topical delivery to the lungs, in particular for the treatment of COPD.

Thus in one aspect there is provided use of a compound of the invention for the treatment of COPD and/or asthma, in particular COPD or severe asthma, by inhalation i.e. by topical administration to the lung. Advantageously, administration to the lung allows the beneficial effects of the compounds to be realised whilst minimising the side-effects, for patients.

In one embodiment the compounds are suitable for sensitizing patients to treatment with a corticosteroid.

Further, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration, and may be different depending on the route of administration.

In one embodiment compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository. In another embodiment, compositions may be prepared for oral administration in the form of liquid solutions or suspensions; for topical administration in the form of liquid solutions, liquid suspensions, nasal drops comprising solutions or suspensions or pressurised or non-pressurised aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). The compositions may also conveniently be administered in multiple unit dosage form.

Formulations for parenteral administration may contain as excipients sterile water or saline, alkylene glycols such as propylene glycol, polyalkylene glycols such as polyethylene glycol, oils of vegetable origin, hydrogenated naphthalenes and the like.

Formulations for nasal administration may be solid and may contain excipients, for example, lactose or dextran, or may be aqueous or oily solutions for use in the form of nasal drops or metered spray. Formulations for nasal administration may also be in the form of aqueous suspensions. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or polyvinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules. Such two-piece hard shell capsules may be made from, for example, gelatin or hydroxypropyl methylcellulose (HPMC).

A dry shell formulation typically comprises of about 40%-60% concentration of gelatin, about a 20%-30% concentration of plasticizer (such as glycerin, sorbitol or propylene glycol) and about a 30%-40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence in one embodiment there is provided a pharmaceutical composition comprising a compound of the disclosure optionally in combination with one or more topically acceptable diluents or carriers.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. These may be administered by means of a nebuliser e.g. one that can be hand-held and portable or for home or hospital use (ie non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean diameter (MMAD) of 1-10 μm or a $D_{50}$ of 0.5-10 μm e.g. around 1-5 μm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. a mass mean diameter (MMAD) of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Example dry powder delivery systems include SPINHALER®, DISKHALER®, TURBOHALER®, DISKUS®, SKYEHALER®, ACCUHALER® and CLICKHALER®. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLI PTA, ORIEL dry powder inhaler, MICRODOSE, PULVI NAL, EASYHALER, ULTRAHALER, TAIFUN, PULMOJET, OMNIHALER, GYROHALER, TAPER, CONIX, XCELOVAIR and PROHALER.

In one embodiment a compound of the present invention is provided as a micronized dry powder formulation, for example comprising lactose of a suitable grade, filled into a device such as DISKUS. Suitably, such a device is a multidose device, for example the formulation is filled into blisters for use in a multi-unit dose device such as DISKUS.

In one embodiment a compound of the present invention is provided as a micronized dry powder formulation, comprising lactose of a suitable grade and magnesium stearate, filled into blisters for use in a multi-dose device such as DISKUS. Suitably, such a device is a multidose device.

In another embodiment a compound of the present invention is provided as a micronized dry powder formulation, for example comprising lactose of a suitable grade, filled into hard shell capsules for use in a single dose device such as AEROLISER.

In another embodiment a compound of the present invention is provided as a micronized dry powder formulation, comprising lactose of a suitable grade and magnesium stearate, filled into hard shell capsules for use in a single dose device such as AEROLISER.

Exemplary compositions of compound (I) which are suitable for use in a dry powder inhaler are listed in Example 15.

The compounds according to the disclosure are intended to have therapeutic activity. In a further aspect, the present invention provides a compound of the disclosure for use as a medicament.

The compounds according to the disclosure may also be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis and virally induced exacerbations of any one of the same, respiratory virus infection, especially asthma, chronic bronchitis and COPD.

Respiratory viruses include influenza, respiratory syncytial virus, human parainfluenza virus, SARS coronavirus and adenoviruses. A further example of a respiratory virus is rhinovirus.

The compound of the disclosure may also re-sensitise the patient's condition to treatment with a corticosteroid, when previously the patient's condition had become refractory to the same.

In one embodiment of the invention a dose of the present compound is employed that is equal to that suitable for use as a monotherapy but administered in combination with a corticosteroid.

In one embodiment a dose of the compound of formula (I) that would be sub-therapeutic as a single agent is employed, in combination with a corticosteroid, thereby restoring patient responsiveness to the latter, in instances where the patient had previously become refractory to the same.

In one embodiment, a dose of the compound of formula (I) is employed, in combination with a dose of corticosteroid that would be sub-therapeutic if administered in the absence of compound of formula (I), thereby restoring patient responsiveness to the corticosteroid, in instances where the patient had previously become refractory to the same.

Additionally, the compound of the disclosure may exhibit anti-viral activity and, for example, prove useful in the treatment of viral exacerbations of inflammatory conditions such as asthma and/or COPD.

The compound of the present disclosure may also be useful in the prophylaxis, treatment or amelioration of disease or the complications of disease associated with influenza virus, rhinovirus and/or respiratory syncytial virus.

In one embodiment there is provided a compound of formula (I) for use in the treatment or prevention of viral infection or inflammatory complications induced by viral infection.

The compound of formula (I), according to the disclosure is also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

In one embodiment the compound of formula (I) is considered useful in the treatment of Hepatitis C and/or HIV, when administered by an appropriate route. Appropriate routes of administration may include oral, intravenous injection or infusion.

In one embodiment the compound of formula (I) for the treatment of Hepatitis C is delivered to the blood pre-entry to the liver.

The compound of the disclosure is also expected to be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

In one embodiment the presently disclosed compound and pharmaceutical formulations comprising the same are useful in the treatment or prevention of cancer, in particular lung cancer, especially by topical administration to the lung.

Thus, in a further aspect, the present invention provides the compound as described herein for use in the treatment of one or more of the above mentioned conditions.

In a further aspect, the present invention provides use of the compound as described herein for the manufacture of a medicament for the treatment of one or more of the above mentioned conditions.

In a further aspect, the present invention provides a method of treatment of the above mentioned conditions which comprises administering to a subject an effective amount of the compound of the disclosure or a pharmaceutical composition thereof.

The compound described herein may also be used in the manufacture of a medicament for the treatment of one or more of the above-identified diseases.

The word "treatment" is intended to embrace prophylaxis as well as therapeutic treatment.

The compound of the disclosure may also be administered in combination with one or more other active ingredients e.g. active ingredients suitable for treating the above mentioned conditions. For example possible combinations for treatment of respiratory disorders include combinations with corticosteroids (e.g. budesonide, beclomethasone dipropionate, fluticasone propionate, mometasone furoate, fluticasone furoate), beta agonists (e.g. terbutaline, salbutamol, salmeterol, formoterol, indacaterol), xanthines (e.g. theophylline), muscarinic antagonists, (e.g. ipratropium) and/or a p38 MAP kinase inhibitor. A further example of a suitable corticosteroid is ciclesonide or flunisolide. Suitably the beta agonist is a beta2 agonist. Further examples of beta2 agonists are reproterol, vilanterol, olodaterol, reproterol and fenoterol. Further examples of muscarinic antagonists include tiotropium, umeclidinium, glycopyrronium, aclidinium and daratropium, any of these for example as the bromide salt. A further possible combination for treatment of respiratory disorders is the compound of the disclosure and a phosphodiesterase inhibitor.

In one embodiment the compound of the disclosure is administered in combination with an antiviral agent, for example acyclovir, oseltamivir, zanamavir (Relenza®) or interferon.

In one embodiment the combination of active ingredients are co-formulated.

In one embodiment the compound of the present disclosure is co-formulated with a corticosteroid as a formulation for inhalation, for example for use in maintenance therapy of COPD or lung cancer including prevention of the latter.

In one embodiment the combination of active ingredients is simply co-administered.

In one embodiment there is provided a combination product comprising:
  (A) a compound of the present disclosure; and
  (B) a further active ingredient e.g. selected from corticosteroids, beta agonists, xanthines, muscarinic antagonists, phosphodiesterase inhibitors and p38 MAP kinase inhibitors (e.g. selected from corticosteroids, beta agonists, xanthines, muscarinic antagonists and p38 MAP kinase inhibitors).

wherein each of components (A) and (B) is formulated in admixture with a pharmaceutically-acceptable diluent or carrier. The combination may optionally comprise additional relevant excipients. Suitably the beta agonist is a beta2 agonist.

In one embodiment there is provided a compound of formula (I) according to claim 1 for use as a medicament to be administered in combination with one or more further active ingredients e.g. selected from corticosteroids, beta agonists, xanthines, muscarinic antagonists and p38 MAP kinase inhibitors. Suitably the beta agonist is a beta2 agonist.

In one embodiment the compound of the disclosure is administered by inhalation and a corticosteroid is administered orally or by inhalation either in combination or separately.

In one embodiment the compound of the disclosure is administered by inhalation and a beta2 agonist is administered orally or by inhalation either in combination or separately.

EXPERIMENTAL SECTION

Abbreviations used herein are defined below (Table 1). Any abbreviations not defined are intended to convey their generally accepted meaning.

TABLE 1

| Abbreviations | |
|---|---|
| Aq | aqueous |
| Ac | acetyl |
| ACD | acid citrate dextrose |
| ATP | adenosine-5'-triphosphate |
| BALF | bronchoalveolae lavage fluid |
| br | broad |
| BSA | bovine serum albumin |
| COPD | chronic obstructive pulmonary disease |
| CXCL1 | CXC motif chemokine ligand 1 |
| CXCL8 | CXC motif chemokine ligand 8 |
| d | doublet |
| DCM | dichloromethane |
| DMA | dimethyl acetamide |
| DMAP | 4-dimethylaminopyridine |
| DMSO | dimethyl sulfoxide |
| EDC•HCl | 1-ethyl-3-(3-dimethylaminopropyl)carbodiimide hydrochloride |
| ELISA | enzyme linked immunosorbent assay |
| (ES+) | electrospray ionization, positive mode |
| Et | ethyl |
| EtOAc | ethyl acetate |
| EtOH | ethanol |
| FACS | fluorescence-activated cell sorting |
| FCS | foetal calf serum |
| FITC | fluorescein isothiocyanate |
| FP | fluticasone propionate |
| HPLC-MS | high performance liquid chromatography mass spectrometry |
| hr | hour(s) |
| HRP | horseradish peroxidase |
| IFNγ | Interferon gamma |
| i-n | intra-nasal |
| i-t | intra-tracheal |
| IL-4 | interleukin 4 |
| IL-5 | interleukin 5 |
| IL-13 | interleukin 13 |
| IL-17 | Interleukin 17 |
| LPS | lipopolysaccharide |
| IPA | isopropanol [propan-2-ol] |
| M | molar |
| (M + H)+ | protonated molecular ion |
| MCP-1 | monocyte chemoattractant protein |
| MDA | malondialdehyde |
| Me | methyl |
| MeOH | methanol |
| MHz | megahertz |
| min | minute(s) |
| MIBK | methyl isobutyl ketone |
| MOMA-2 | anti-monocyte and macrophage antibody |
| MTT | 3-(4,5-dimethylthiazol-2-yl)-2,5-diphenyltetrazolium bromide |
| m/z | mass-to-charge ratio |
| $NH_4OAc$ | ammonium acetate |
| nm | nanometre |
| NMP | N-methyl pyrrolidone |
| NMR | nuclear magnetic resonance (spectroscopy) |
| OVA | ovalbumin |
| PBMC | peripheral blood mononuclear cell(s) |
| PBS | phosphate buffered saline |
| $Pd_2(dba)_3$ | tris(dibenzylideneacetone)dipalladium(0) |
| $PdCl_2(PPh_3)_2$ | bis(triphenylphosphine)palladium(II) dichloride |
| Ph | phenyl |
| PIP2 | phosphatidylinositol 4,5-biphosphate |
| PIP3 | phosphatidylinositol 3,4,5-triphosphate |
| PMA | phorbol myristate acetate |
| po | by oral administration |
| $PPh_3$ | triphenylphosphine |
| q | quartet |
| quin | quintet |
| $R^t$ | retention time |
| RH | relative humidity |
| RT | room temperature |
| RP HPLC | reverse phase high performance liquid chromatography |
| s | singlet |
| SDS | sodium dodecyl sulfate |
| SEM | standard error of the mean |
| t | triplet |
| TBME | methyl tent-butyl ether |
| THF | tetrahydrofuran |
| TMB | 3,3',5,5'-tetramethylbenzidine |
| TNFα | tumour necrosis factor alpha |
| TR-FRET | time-resolved fluorescence resonance energy transfer |

General Procedures

All starting materials and solvents were obtained either from commercial sources or prepared according to the literature citation. Unless otherwise stated all reactions were stirred. Organic solutions were routinely dried over anhydrous magnesium sulfate.

Column chromatography was performed on pre-packed silica (230-400 mesh, 40-63 μm) cartridges using the amount indicated.

Analytical Methods

Analytical LCMS

Analytical LCMS was carried out using a Waters Xselect CSH $C_{18}$ 3.5 μm column (4.6×50 mm) with a flow rate of 2.5-4.5 mL $min^{-1}$ eluting with a $H_2O$-MeCN gradient containing 0.1% v/v formic acid over 4 min. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL $min^{-1}$; 3.01 3.50 min, held at 5% $H_2O$-95% MeCN; 3.50-3.60 min, returned to 95% $H_2O$-5% MeCN, flow rate reduced to 3.50 mL $min^{-1}$; 3.60-3.90 min, held at 95% $H_2O$-5% MeCN; 3.90-4.00 min, held at 95% $H_2O$-5% MeCN, flow rate reduced to 2.5 mL $min^{-1}$. Sample containing fractions were detected by their UV absorbance at 254 nm. Mass spectra of the eluted peaks were measured using an Agilent 6120 quadrupole mass spectrometer operating in mixed positive and negative ion electrospray modes.

$^1$H NMR Spectroscopy $^1$H NMR spectra were acquired on a Bruker Avance III spectrometer at 400 MHz using residual undeuterated solvent as reference and unless specified otherwise were run in DMSO-$d_6$.

X-Ray Powder Diffraction—Method 1 (Using a Brucker AXS C2 GADDS Diffractometer)

Diffraction patterns were collected using Cu Kα radiation (40 kV, 40 mA), automated XYZ stage, laser video microscope for auto-sample positioning and a HiStar 2-dimensional area detector. X-ray optics consisted of a single Göbel multilayer mirror coupled with a pinhole collimator of 0.3 mm. The beam divergence i.e. the effective size of the X-ray beam on the sample was approximately 4 mm. A θ-θ continuous scan mode was employed with a sample-detector distance of 20 cm which gave an effective 2θ range of 3.2°-29.7°. Typically the sample was exposed to the X-ray beam for 120 seconds. The software used for data collection was GADDS for XP/2004 4.1.43 and the data were analyzed and presented using Diffrac Plus EVA v13.0.0.2 or v15.0.0.0. Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat-conducting compound. The sample was then heated to the appropriate temperature at 20° C./min and subsequently held isothermally for 1 minute before data collection was initiated.

X-Ray Powder Diffraction—Method 2 (Using a Brucker AXS D8 Advance Diffractometer)

Diffraction patterns were collected using Cu Kα radiation (40 kV, 40 mA), θ-2θ goniometer, and divergence of V4 and receiving slits, a Ge monochromator and a Lynxeye detector. The software used for data collection was Diffrac Plus XRD Commander v2.6.1 and the data were analyzed and presented using Diffrac Plus EVA v13.0.0.2 or v15.0.0.0. Samples were run under ambient conditions as flat plate specimens using powder as received. The sample was gently packed into a cavity cut into polished, zero-background (510) silicon wafer. The sample was rotated in its own plane during analysis. The details of the data collection are: angular range: 2 to 42° 2θ; step size: 0.05° 2θ; collection time: 0.5 s/step.

X-Ray Powder Diffraction—Method 3 (Using a PANalytical (Philips) X'PertPRO MPD Diffractometer)

The instrument was equipped with a Cu LFF X-ray tube. The compound was spread on a zero background sample holder. The instrument parameters used are as follows: generator voltage: 45 kV; generator amperage: 40 mA; geometry: Bragg-Brentano; stage: spinner stage. The measurement conditions were as follows: scan mode: continuous; scan range: 3 to 50° 2θ; step size: 0.02°/step; counting time: 30 sec/step; spinner revolution time: 1 sec; radiation type: CuKα. The incident beam path parameters were as follows: program. divergence slit: 15 mm; Soller slit: 0.04 rad; beam mask: 15 mm; anti scatter slit: 1°; beam knife: +. The diffracted beam path parameters were as follows: long anti scatter shield: +; Soller slit: 0.04 rad; Ni filter: +; detector: X'Celerator.

Differential Scanning Calorimetry—Method 1 (Using a Mettler DSC 823e Instrument)

A Mettler DSC 823E is equipped with a 34 position auto-sampler. The instrument was calibrated for energy and temperature using certified indium. Typically 0.5-3 mg of each sample, in a pin-holed aluminium pan, was heated at 10° C./min from 25° C. to 300° C. A nitrogen purge at 50 ml/min was maintained over the sample. The instrument control and data analysis software was STARe v9.20.

Differential Scanning Calorimetry—Method 2 (Using a TA-Instruments Q1000 MTDSC Equipped with a RCS Cooling Unit)

A TA-Instrument sample pan was closed with the appropriate cover and the DSC curve recorded on a TA-Instruments Q1000 MTDSC equipped with a RCS cooling unit. The following parameters were used: initial temperature: 25° C.; heating rate: 10° C./min; final temperature: 250° C.

Thermo-Gravimetric Analysis—Method 1 (Using a Mettler TGA/SDTA 851e Instrument)

TGA data were collected on a Mettler TGA/SDTA 851e equipped with a 34 position auto-sampler. The instrument was temperature calibrated using certified indium. Typically 5-30 mg of each sample was loaded onto a pre-weighed aluminium crucible and was heated at 10° C./min from ambient temperature to 350° C. A nitrogen purge at 50 ml/min was maintained over the sample. The instrument control and data analysis software was STARe v9.20.

Thermo-Gravimetric Analysis (TGA)—Method 2 (Using a TA-Instruments Q500 TGA Thermogravimeter)

TGA data were collected on a TA-Instruments Q500 TGA thermogravimeter. The compound was transferred into an aluminium sample pan before being analysed using the following parameters: initial temperature: room temperature; heating rate: 20° C./min; resolution factor: 4; final condition: 350° C. or <80[(w/w) %].

Gravimetric Vapour Sorption (GVS)

Sorption isotherms were obtained using a SMS DVS Intrinsic moisture sorption analyser, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 ml/min The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (4 scans giving 2 complete cycle). The standard isotherm was performed at 25° C. at 10% RH intervals over a 0-90% RH range. Data analysis was undertaken in Microsoft Excel using DVS Analysis Suite v6.2 (or 6.1 or 6.0).

TABLE 2

Method Parameters for SMS DVS Intrinsic Experiments

| Parameters | Values |
| --- | --- |
| Adsorption-Scans 1 and 3 | 40-90 |
| Desorption/Adsorption-Scans 2 and 4 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |

The sample was recovered after completion of the isotherm and re-analysed by XRPD.

Dynamic Vapour Sorption (DVS)

About 20 mg of the compound was transferred into an SMS dynamic vapor sorption and the weight change recorded with respect to the atmospheric humidity at 25° C. using the following parameters: drying: 60 min under dry nitrogen; equilibrium: 60 min; RH (%) measurement points: cycle1: 5, 10, 20, 30, 40, 50, 60, 70, 80, 90, 95, 90, 80, 70, 60, 50, 40, 30, 20, 10, 5; cycle2: 10, 20, 30, 40, 50, 60, 70, 80, 90, 95, 90, 80, 70, 60, 50, 40, 30, 20, 10, 5, 0.

Example 1—Preparation of Compound (I) and Compound (Ia)

Intermediate A: 2-((4-Amino-3-iodo-1H-pyrazolo[3,4-d]pyrimidin-1-yl)methyl)-5-bromo-3-(2-(trifluoromethyl)benzyl)quinazolin-4(3H)-one

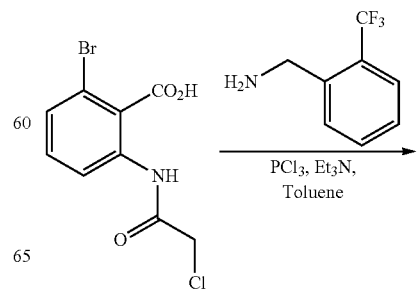

-continued

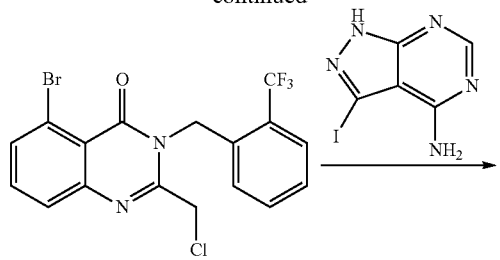

To a stirred mixture of 2-bromo-6-(2-chloroacetamido) benzoic acid [King-Underwood et al., WO2011/048111], (50.0 g, 171 mmol), (2-(trifluoromethyl)phenyl)methanamine (29.4 mL, 205 mmol) and triethylamine (34 mL, 430 mmol) in toluene (1.2 L) at −1° C. was added a solution of phosphorus trichloride (37 mL, 430 mmol) in toluene (100 mL) dropwise over 1 hr, during which time the internal temperature was maintained below 5° C. The reaction mixture was heated to reflux for 2.5 hr and the resulting suspension was then filtered whilst still hot. The filtrate was retained and the collected solid was suspended in fresh toluene (100 mL), and was heated to 90° C. with vigorous stirring. The solid was removed by filtration and the the organic extracts containing the crude product were combined.

A second batch of this material was prepared by repeating the reaction under identical conditions on the same scale. The combined filtrates from both reactions were evaporated in vacuo and the residue was triturated with IPA (2×400 mL). The crude material so obtained was dried in vacuo to afford 5-bromo-2-(chloromethyl)-3-(2-(trifluoromethyl) benzyl) quinazolin-4(3H)-one as an off-white solid (100 g, 90% purity by HPLC, 61%); R$^t$ 2.70 min; m/z 431/433 (M+H)$^+$ (ES$^+$).

To a solution of the quinazolinone, obtained as described above, (100 g, 90% pure, 210 mmol) and 3-iodo-1H-pyrazolo[3,4-d]pyrimidin-4-amine (50.4 g, 193 mmol) in DMF (600 mL) at RT was added potassium carbonate (80.0 g, 580 mmol) and after 18 hr the reaction mixture was poured into water (1.2 L). The resulting precipitate was collected by filtration, and was washed sequentially with water (500 mL), with EtOAc (600 mL) and finally with Et$_2$O (400 mL). The resulting cake was dried in vacuo to afford the title compound, Intermediate A, as an off white solid (115 g, 89%); R$^t$ 2.28 min, m/z 656/658 (M+H)$^+$ (ES$^+$).

Intermediate B: 2-((4-Amino-3-(3-fluoro-5-hydroxyphenyl)-1H-pyrazolo[3,4-d]pyrimidin-1-yl) methyl)-5-bromo-3-(2-(trifluoromethyl)benzyl)quinazolin-4(3H)-one

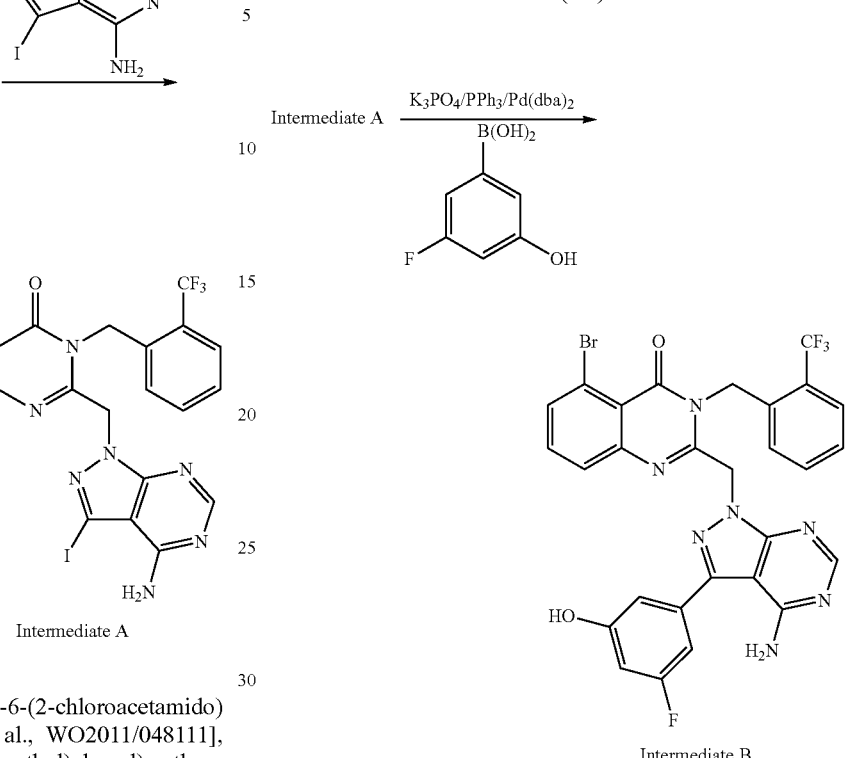

A solution of Intermediate A (54.4 g, 83.0 mmol), (3-fluoro-5-hydroxyphenyl)boronic acid (15.5 g, 99.0 mmol) and K$_3$PO$_4$ (19.1 g, 83.0 mmol) in 1-butanol (900 mL) was sparged with nitrogen at RT for 20 min. The mixture was treated with PPh$_3$ (3.26 g, 12.4 mmol) and with Pd$_2$(dba)$_3$ (1.90 g, 2.07 mmol) and was sparged with nitrogen for an additional 10 min and was then heated to 90° C. under a flow of nitrogen. After 40 hr the mixture was cooled to 70° C. and water (250 mL) was added dropwise. The mixture was cooled to 50° C. for 3 hr and then to RT for 3 days during which time a beige precipitate formed. The solid was collected by filtration, washed with 1-butanol (2×100 mL) and with water (2×100 mL) and was then dried in vacuo at 40° C. to afford the title compound, Intermediate B, as an off-white solid (35.2 g, 65%); R$^t$ 2.25 min, m/z 640/642 (M+H)$^+$ (ES$^+$).

Compound (I): 2-((4-Amino-3-(3-fluoro-5-hydroxyphenyl)-1H-pyrazolo[3,4-d]pyrimidin-1-yl)methyl)-5-(3-(2-(2-methoxyethoxy)ethoxy)prop-1-yn-1-yl)-3-(2-(trifluoromethyl)benzyl)quinazolin-4(3H)-one

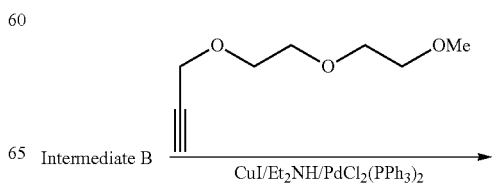

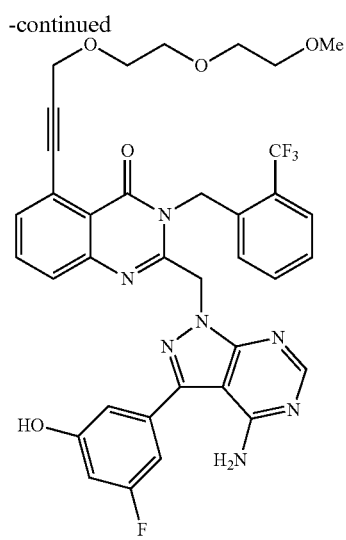

Compound (I)

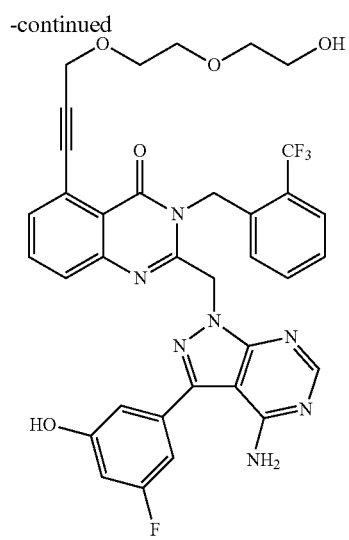

Compound (Ia)

A suspension of Intermediate B (35.2 g, 55.0 mmol), 3-(2-(2-methoxyethoxy)ethoxy)prop-1-yne [King-Underwood et al., WO2011/048111], (17.4 g, 110 mmol), PdCl$_2$(PPh$_3$)$_2$ (3.86 g, 5.50 mmol) and copper(I) iodide (1.05 g, 5.50 mmol) in a mixture of Et$_2$NH and DMF (4:1 v/v, 820 mL) was sparged with nitrogen at RT for 10 min. The mixture was heated to 65° C. for 1.5 hr and was then cooled to RT. The volatiles were evaporated in vacuo and the residue was partitioned between EtOAc (600 mL) and sat. aq. NH$_4$OAc (650 mL). The aq layer was separated and was extracted with EtOAc (300 mL) and the combined organic layers were evaporated in vacuo to afford a dark brown viscous oil. Methanol (200 mL) was added and the mixture was stirred at RT for 16 hr. A yellow precipitate was formed which was collected by filtration and washed with MeOH (100 mL). The resulting solid was purified by flash column chromatography in two separate batches (SiO$_2$, 330 g, MeOH in DCM, 0-6%, gradient elution). The purified materials were taken up together, in a mixture of DCM/MeOH (10:1 v/v) to give a homogeneous solution which was then evaporated and dried in vacuo to afford the title compound, Compound (I), as an off-white solid (20.1 g, 51%); Rt 2.15 min, m/z 718 (M+H)$^+$ (ES$^+$); $^1$H NMR δ: 3.19 (3H, s), 3.35-3.38 (2H, overlapping m), 3.44-3.49 (4H, overlapping m), 3.60-3.63 (2H, overlapping m), 4.37 (2H, s), 5.49 (2H, s), 5.76 (2H, s), 6.42 (1H, d), 6.65 (1H, m), 6.73 (1H, m), 6.79 (1H, m), 7.15 (1H, t), 7.28 (1H, t), 7.52 (1H, d), 7.65-7.69 (2H, overlapping m), 7.82 (1H, m), 8.12 (1H, s), 10.15 (1H, s)

Compound (Ia): 2-((4-Amino-3-(3-fluoro-5-hydroxyphenyl)-1H-pyrazolo[3,4-d]pyrimidin-1-yl)methyl)-5-(3-(2-(2-hydroxyethoxy)ethoxy)prop-1-yn-1-yl)-3-(2-(trifluoromethyl)benzyl)quinazolin-4(3H)-one

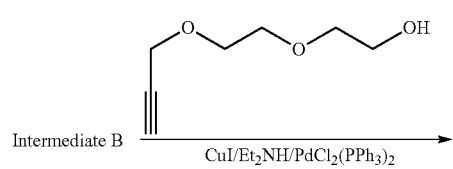

A suspension of Intermediate B (190 mg, 0.297 mmol), 2-(2-(prop-2-yn-1-yloxy)ethoxy)ethanol [King-Underwood et al., WO2011/048111] (257 mg, 0.890 mmol), PdCl$_2$(PPh$_3$)$_2$ (208 mg, 0.297 mmol) and copper(I) iodide (57 mg, 0.30 mmol) in a mixture of Et$_2$NH and DMF (4:1 v/v, 7.5 mL) was degassed with N$_2$ and was then heated to 60° C. for 16 hr. The reaction mixture was cooled to RT and was evaporated in vacuo onto silica gel and purified by flash column chromatography (SiO$_2$, 12 g, MeOH in DCM, 0-5%, gradient elution) to afford the title compound, Compound (Ia), as a pale tan solid (30 mg, 14%); Rt 1.88 min, m/z 704 (M+H)$^+$ (ES$^+$); $^1$H NMR δ: 3.36-3.50 (6H, overlapping m), 3.61-3.63 (2H, overlapping m), 4.37 (2H, s), 4.58 (1H, m), 5.48 (2H, s), 5.76 (2H, s), 6.41 (1H, d), 6.64 (1H, m), 6.72 (1H, d), 6.78 (1H, s), 7.14 (1H, t), 7.27 (1H, t), 7.52 (1H, d), 7.65-7.71 (2H, overlapping m), 7.82 (1H, t), 8.13 (1H, s), 10.19 (1H, br s).

Based on the analysis of structurally similar compounds (see WO2011/048111), it is considered very unlikely that compound (I) will exhibit atropisomerism. The additional complexity and consequences for drug development resulting from atropisomerism are analogous to those arising from other sources of molecular isomerism such as the presence of a stereogenic centre. This property renders such molecules both chiral, and unless resolved, a racemic mixture; the components of which could possess different pharmacological and toxicological profiles. This feature is likely to significantly increase downstream development costs for such molecules, and the absence of atropisomerism in compound (I) is therefore a highly desirable and advantageous property.

Example 2—Preparation of Compound (I) as the Form 1 Crystalline Polymorph

Compound (I) as the Form 1 crystalline polymorph was prepared starting from Intermediate B, which may be prepared as summarised in the following scheme:

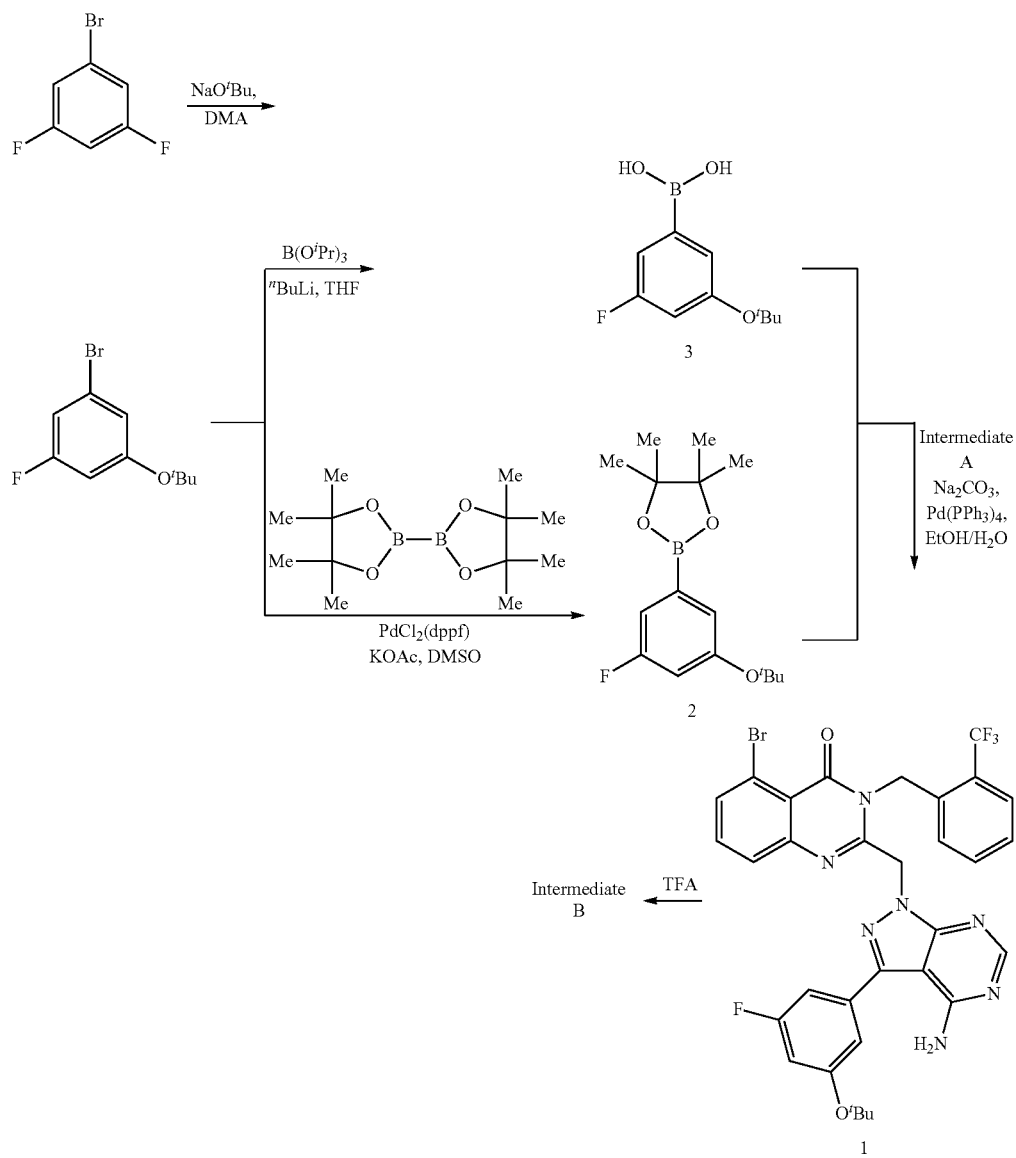

The preparation of the intermediates is set out below.

1-Bromo-3-(tert-butoxy)-5-fluorobenzene

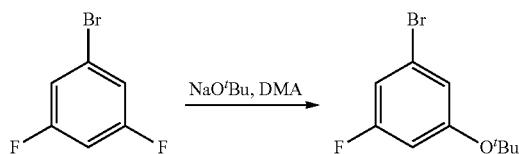 [SMILES: Fc1cc(F)cc(Br)c1 ; CC(C)(C)Oc1cc(F)cc(Br)c1]

To ice cooled DMA (2.0 L) was added sodium tert-butoxide (284 g, 3.89 mols) portionwise followed by dropwise addition of 1-bromo-3,5-difluorobenzene (298 mL, 2.59 mols). Upon completion of the addition the mixture was warmed to RT and stirred for 72 hr. Water (200 mL) was added and the resulting gummy precipitate was filtered. The supernatant was concentrated in vacuo and the residue purified by vacuum distillation. The resulting oil was dissolved in diethyleter (1.0 L), washed with water (6×250 mL), dried (MgSO$_4$) and concentrated in vacuo to yield the title compound as a colourless oil (220 g, 881 mmol, 34.0%): b.p. 84-86° C. (8 mbar); $^1$H NMR (400 MHz, CDCl$_3$) δ: 1.35 (9H, s), 6.64 (1H, dt), 6.92-6.96 (2H, overlapping m).

(3-(tert-Butoxy)-5-fluorophenyl)boronic acid; 2

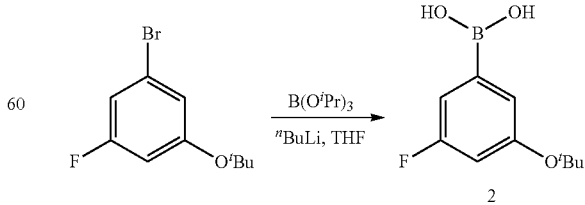

To a solution of 1-bromo-3-(tert-butoxy)-5-fluorobenzene (75.0 g, 304 mmol) in THF (1.0 L) was added n-butyllithium (2.5 M in hexanes, 150 mL, 337 mmol) dropwise at −78° C. The resulting mixture was stirred at this temperature for 45 mins and then triisopropyl borate (105 mL, 455 mmol) was added dropwise. The mixture was stirred at that temperature for 1.5 hr, and then warmed to −5° C. over 1.5 hr. The mixture was diluted with diethyl ether (1.0 L) and 1M aq HCl solution (450 mL) and the layers separated. The aqueous layer was extracted with further diethyl ether (2×250 mL). The combined organic extracts were dried (MgSO$_4$), filtered and then evaporated in vacuo to yield a pale yellow oil. The oil was redissolved in iso-hexanes (300 mL) and concentrated again to afford an off-white sticky solid. The solid was triturated with iso-hexanes (150 mL) and filtered to afford a white powder. The material was partitioned between 2M NaOH (600 mL) and diethyl ether (600 mL). The aqueous layer was collected and the organic extracted with further NaOH (2×200 mL). A significant quantity of material was not soluble and this was filtered, washing with diethyl ether (confirmed as clean product by LCMS). The basic aqueous layer was cooled in an ice bath and acidified to pH 1 with conc. HCl (~130 mL). The aqueous layer was extracted with DCM (3×300 mL) and the combined organics dried (Na$_2$SO$_4$), filtered and concentrated in vacuo to yield a beige powder. This was triturated with iso-hexanes (100 mL) to afford further clean product. The two batches were combined to yield the title compound 2 as an off-white powder (17.2 g, 73.0 mmol, 24.1%): R$_t$: 1.87 min.

2-(3-(tert-Butoxy)-5-fluorophenyl)-4,4,5,5-tetramethyl-1,3,2-dioxaborolane; 3

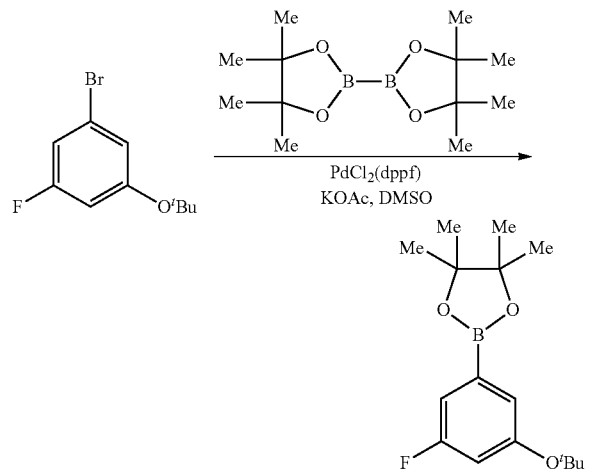

A mixture of palladium(II)dichloride-1,1'-bis(diphenylphosphino)ferrocene (6.81 g, 9.31 mmol), potassium acetate (54.8 g, 558 mmol) and 4,4,4',4',5,5,5',5'-octamethyl-2,2'-bi (1,3,2-dioxaborolane) (52.0 g, 205 mmol) was flushed with nitrogen and to this was added a solution of 1-bromo-3-(tert-butoxy)-5-fluorobenzene (46.0 g, 186 mmol) in DMSO (528 mL). The resulting mixture was sonicated for 3 minutes, degassed for 5 minutes and heated at 80° C. for 23 hr. The reaction mixture was partitioned between diethyl ether (500 mL) and water (500 mL). The aqueous layer was extracted with further diethyl ether (3×400 mL). The combined organic extracts were washed with brine (300 mL), dried (MgSO$_4$), filtered and evaporated in vacuo to yield a dark brown residue. This residue was dissolved in a mixture of iso-hexanes/EtOAc, filtered through a short plug of silica and evaporated in vacuo to yield a light brown solid. The solid residue was pre-adsorbed onto silica and was purified by column chromatography, (SiO$_2$, eluting with 0-4% EtOAc in iso-hexanes, gradient elution) to yield the title compound 3 as a white solid. (27.0 g, 87.0 mmol, 46.8%): $^1$H NMR (400 MHz, CDCl$_3$) δ: 1.31 (12H, s), 1.34 (9H, s), 6.78 (1H, m), 7.17-7.20 (2H, overlapping m).

2-((4-Amino-3-(3-(tert-butoxy)-5-fluorophenyl)-1H-pyrazolo[3,4-d]pyrimidin-1-yl)methyl)-5-bromo-3-(2-(trifluoromethyl)benzyl)quinazolin-4(3H)-one; 1 (from boronic acid, 3)

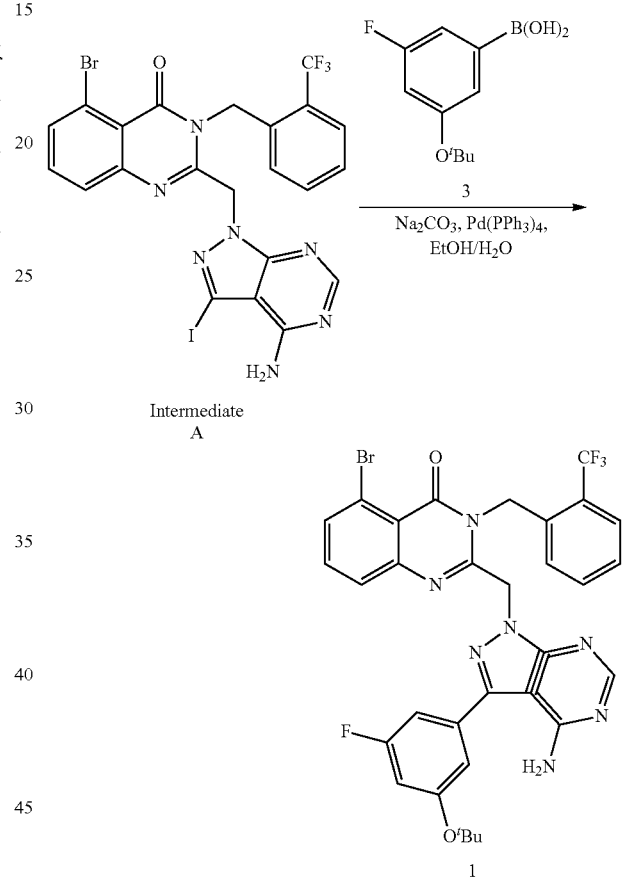

A mixture Intermediate A (2×10.0 g, 14.9 mmol), (3-(tert-butoxy)-5-fluorophenyl)boronic acid 3 (2×3.17 g, 14.9 mmol), sodium carbonate decahydrate (2×6.75 g, 23.6 mmol) and palladium tetrakis triphenylphosphine (2×0.52 g, 0.45 mmol) in a mixture of EtOH/water (9:1, 2×500 mL) was degassed with nitrogen, sonicated for 10 mins and was then stirred at 65° C. under nitrogen for 18 hr. The reaction mixtures were combined and the solvents were removed in vacuo, the residue dissolved in 10% MeOH in DCM solution (500 mL) and washed with sat. ammonium acetate solution (400 mL). The aqueous layer was extracted with further 10% MeOH in DCM solution (2×400 mL). The combined organic extracts were evaporated in vacuo and the residue was pre-adsorbed onto silica gel and purified by flash column chromatography (eluting with 0-40% EtOAc in DCM, gradient elution) to yield the title compound 1 as a pale yellow solid (8.4 g, 9.89 mmol, 32.4%): R$_t$ 2.70 min, $^1$H NMR (400 MHz, DMSO-d$_6$) δ: 1.37 (9H, s), 5.50 (2H, s), 5.78 (2H, s), 6.49 (1H, d), 6.91 (1H, t), 6.95 (1H, dt), 7.04 (1H, m), 7.15 (1H, t), 7.28 (1H, t), 7.54 (1H, d), 7.68-7.72 (2H, overlapping m), 7.83 (1H, dd), 8.15 (1H, s). The material was approximately 80% pure.

2-((4-Amino-3-(3-(tert-butoxy)-5-fluorophenyl)-1H-pyrazolo[3,4-d]pyrimidin-1-yl)methyl)-5-bromo-3-(2-(trifluoromethyl)benzyl)quinazolin-4(3H)-one; 1 (from boronic ester, 2)

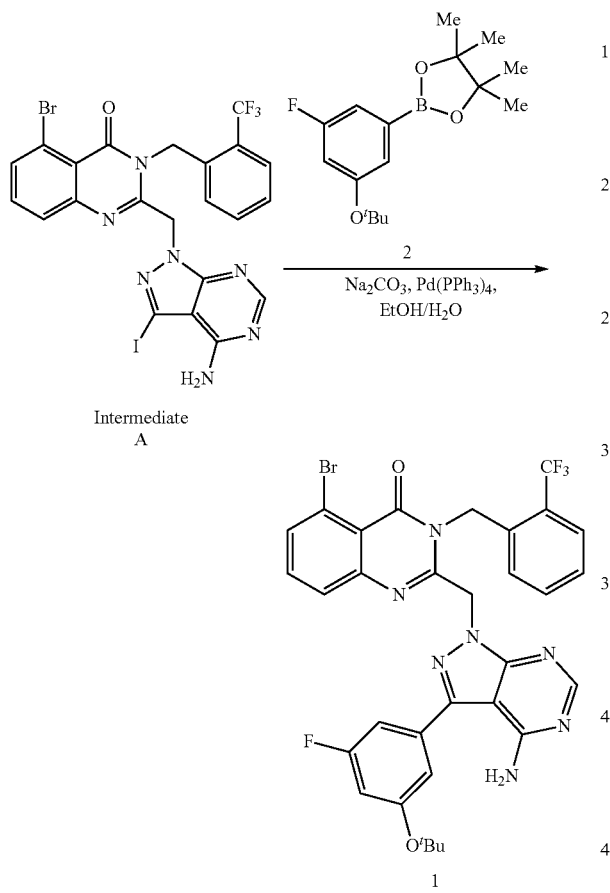

A mixture of Intermediate A (10.0 g, 14.9 mmol; prepared as described in Example 1), 2-(3-(tert-butoxy)-5-fluorophenyl)-4,4,5,5-tetramethyl-1,3,2-dioxaborolane 2 (6.59 g, 22.40 mmol) (3.17 g, 14.9 mmol), sodium carbonate decahydrate (26.75 g, 23.6 mmol) and palladium tetrakis triphenylphosphine (0.52 g, 0.45 mmol) in a mixture of EtOH/water (9:1, 500 mL) was degassed with nitrogen, sonicated for 10 mins and was then stirred at 65° C. under nitrogen for 40 hr. The solvents were removed in vacuo, the residue dissolved in 10% MeOH in DCM solution (250 mL) and washed with sat. ammonium acetate solution (200 mL). The aqueous layer was extracted with further 10% MeOH in DCM solution (2×200 mL). The combined organic extracts were evaporated in vacuo and the residue was pre-adsorbed onto silica gel and purified by flash column chromatography (eluting with 0-40% EtOAc in DCM, gradient elution) to yield the title compound as a pale yellow solid (4.5 g, 6.14 mmol, 41.1%): $R_t$ 2.70 min.

2-((4-Amino-3-(3-fluoro-5-hydroxyphenyl)-1H-pyrazolo[3,4-d]pyrimidin-1-yl)methyl)-5-bromo-3-(2-(trifluoromethyl)benzyl)quinazolin-4(3H)-one

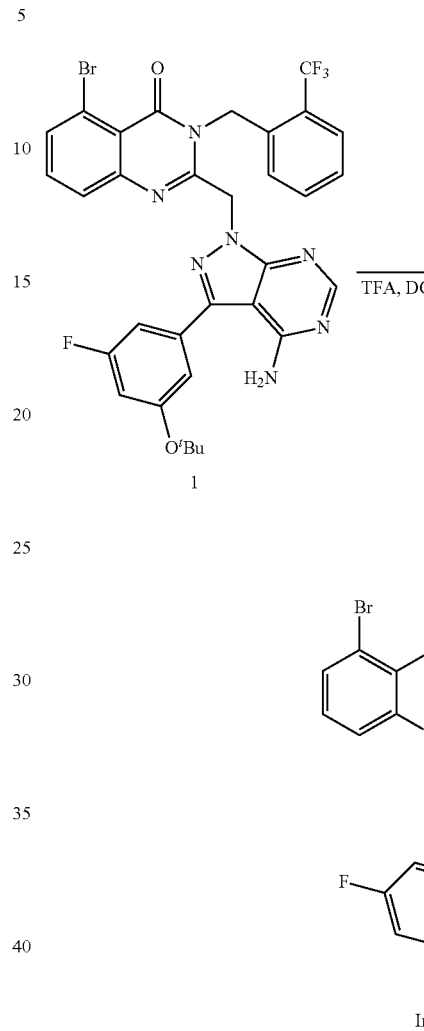

To a solution of 2-((4-amino-3-(3-(tert-butoxy)-5-fluorophenyl)-1H-pyrazolo[3,4-d]pyrimidin-1)methyl)-5-bromo-3-(2-(trifluoromethyl)benzyl)quinazolin-4(3H)-one 1 (13.0 g, 18.6 mmol) in DCM (150 mL) was added trifluoroacetic acid (21.6 mL, 280 mmol) and the resulting solution was stirred for 2 hr. The solvent was removed in vacuo. The residue was taken up in DCM (200 mL) and a saturated solution of NaHCO$_3$ (200 mL). The aqueous layer was extracted further with 10% MeOH in DCM (2×100 mL) and the combined organic extracts were evaporated in vacuo. The residue was pre-adsorbed onto silica gel and was purified by flash column chromatography eluting with 0-3% MeOH in DCM to yield the title compound 1b as a white solid (7.60 g, 11.8 mmol, 63.0%): m/z 640 (M+H)$^+$ (ES$^+$); $^1$H NMR (400 MHz, DMSO-d$_6$) δ: 5.47 (2H, s), 5.78 (2H, s), 6.43 (1H, d), 6.65 (1H, dt), 6.75 (1H, m), 6.79 (1H, t), 7.14 (1H, t), 7.28 (1H, t), 7.53 (1H, d), 7.69-7.73 (2H, overlapping m), 7.85 (1H, m), 8.13 (1H, s), 10.18 (1H, d).

Compound (I): 2-((4-Amino-3-(3-fluoro-5-hydroxy-phenyl)-1H-pyrazolo[3,4-d]pyrimidin-1-yl)methyl)-5-(3-(2-(2-methoxyethoxy)ethoxy)prop-1-yn-1-yl)-3-(2-(trifluoromethyl)benzyl)quinazolin-4(3H)-one as the Form 1 crystalline polymorph

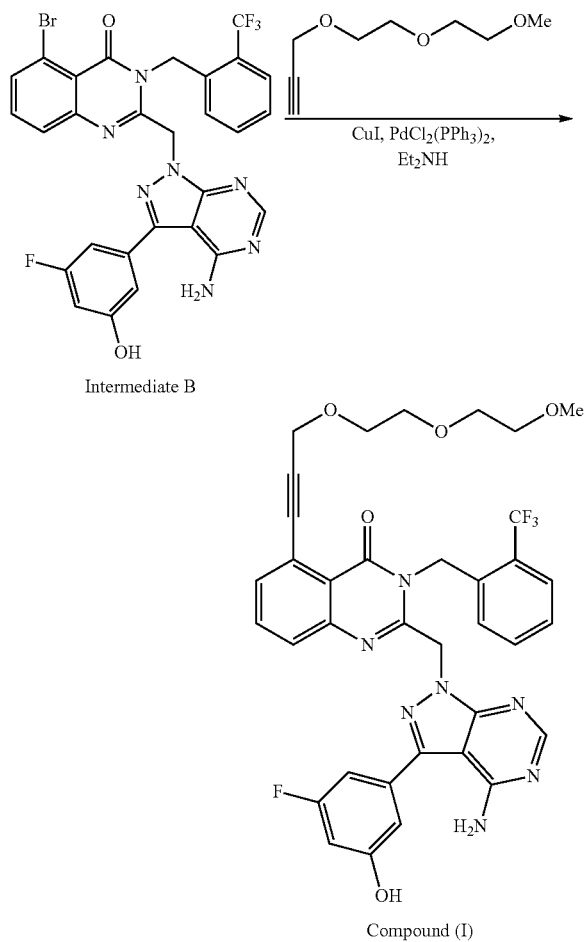

Intermediate B

Compound (I)

A mixture of 3-(2-(2-methoxyethoxy)ethoxy)prop-1-yne (4.69 g, 29.7 mmol), copper(I) iodide (226 mg, 1.19 mmol), Intermediate B (7.6 g, 11.9 mmol) and bis(triphenylphosphine)palladium(II) dichloride (833 mg, 1.19 mmol) in diethylamine (330 mL) was thoroughly degassed with nitrogen and stirred at 60° C. for 3 hr. More 3-(2-(2-methoxyethoxy)ethoxy)prop-1-yne (400 mg), bis(triphenylphosphine)palladium(II) dichloride (167 mg, 0.24 mmol) and copper(I) iodide (0.45 g, 0.24 mmol) was added in diethylamine (30.0 mL) and stirred at 60° C. for 3 hr. A further aliquot of 3-(2-(2-methoxyethoxy)ethoxy)prop-1-yne 7 (400 mg), bis(triphenylphosphine)palladium(II) dichloride (167 mg, 0.24 mmol) and copper(I) iodide (0.45 g, 0.24 mmol) was added and the reaction mixture was stirred at 60° C. for a further 7 hr. The solvent was removed in vacuo, the residue dissolved in 10% MeOH in DCM solution (200 mL) and washed with aqueous ammonium acetate solution (10 wt %, 300 mL). The aqueous layer was further extracted with 10% MeOH in DCM solution (2×200 mL). The combined organic layer was evaporated in vacuo. The residue was slurried in MeOH (30.0 mL) overnight and filtered. The solid residue was pre adsorbed onto silica and was purified by column chromatography, (SiO$_2$, eluting with 0-5% MeOH in DCM, gradient elution) to yield compound (I) as a tan solid in the form of the Form 1 crystalline polymorph (4.73 g, 6.52 mmol, 55.0%): m/z 718 (M+H)$^+$ (ES$^+$); $^1$H NMR (400 MHz, DMSO-d$_6$) δ: 3.20 (3H, s), 3.35-3.39 (2H, overlapping m), 3.43-3.50 (4H, overlapping m), 3.60-3.64 (2H, overlapping m), 4.38 (2H, s), 5.49 (2H, s), 5.77 (2H, s), 6.42 (1H, d), 6.65 (1H, dt), 6.74 (1H, dq), 6.79 (1H, t), 7.15 (1H, t), 7.28 (1H, t), 7.52 (1H, d), 7.65-7.72 (2H, overlapping m), 7.83 (1H, m), 8.13 (1H, s), 10.19 (1H, s).

XRPD analysis of a sample of this material was undertaken using XRPD method 2 in the General Procedures. The material was crystalline as shown in the XRPD pattern obtained (FIG. 3), but also contained some amorphous material.

Figure 4:
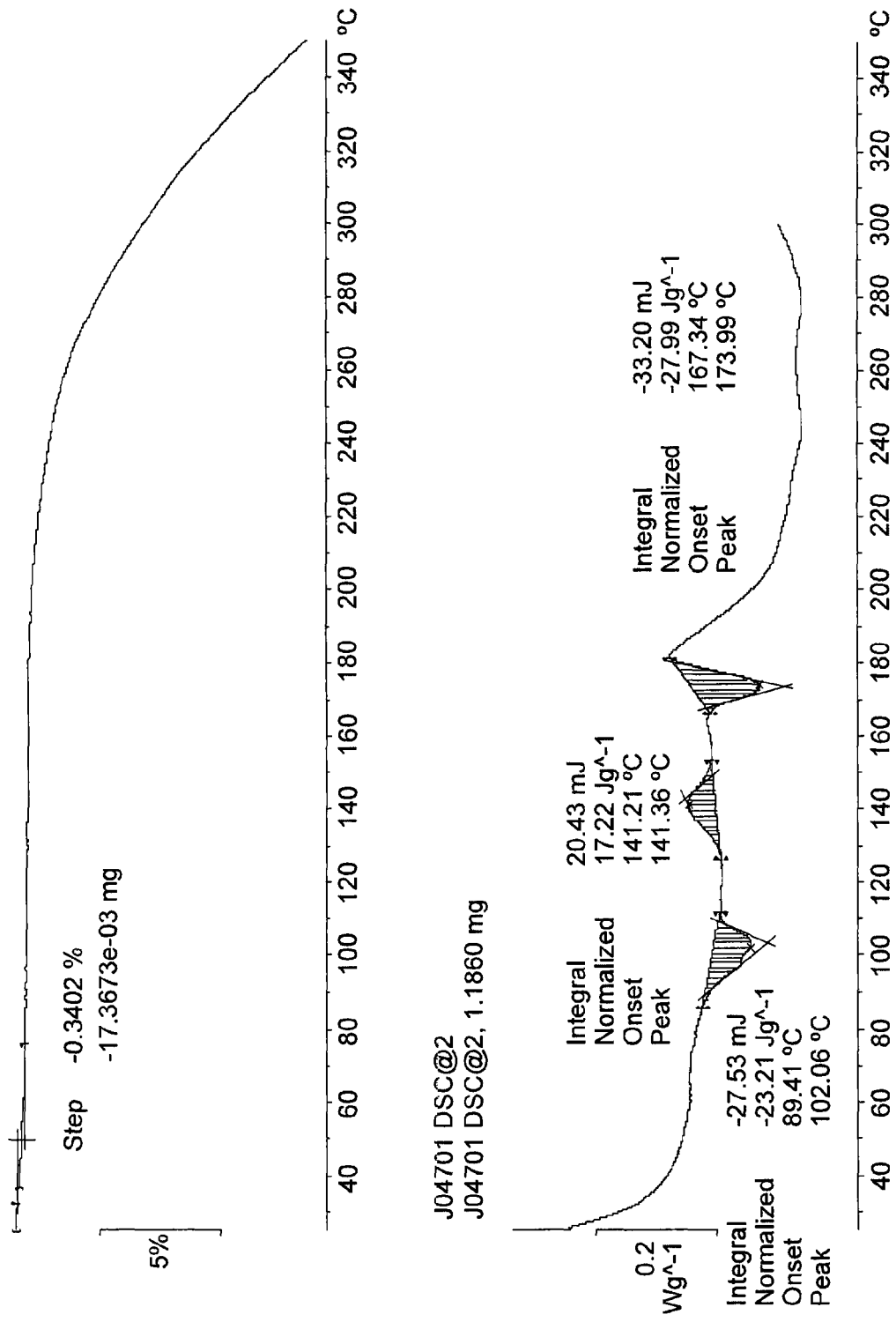
FIG. 4: shows a thermo-gravimetric analysis (TGA) (top plot) and differential scanning calorimetry analysis (DSC) (bottom plot) analysis of a sample of the Form 1 crystalline polymorph (see Example 2)

A DSC analysis (using DSC method 1 in the General procedures) on a sample of the Form 1 crystalline polymorph is shown in FIG. 4 (bottom plot), where it can be seen that the sample underwent a number of events on heating. A broad endotherm with a peak maximum of 102° C. was followed by an exotherm with a peak maximum of 141° C., which was followed by a sharper endotherm with a peak maximum of 174° C. It was observed that during heating a new crystalline polymorph was formed—later found to be the Form 2 crystalline polymorph. TGA analysis (using TGA method 1 in the General Procedures) on a sample of the Form 1 crystalline polymorph (FIG. 4; top plot) showed weight loss of 0.34% from ambient to 75° C. probably due to evaporation of free solvent and/or hygroscopic water.

Example 3—Preparation of Compound (I) as the Form 2 Crystalline Polymorph

Method 1

The Form 2 crystalline polymorph may be prepared by crystallizing from a solution in 1-propanol, as follows. A 100 ml reactor was charged with 1.98 g of compound (I) and 49.5 ml 1-propanol (25 L/kg). The mixture was stirred and warmed to 95° C. (a solution was observed at 92° C.). The solution was held at 95° C. for 30 minutes before being cooled to 23° C. over 10 hours, with spontaneous crystallization occurring at 72° C. The heterogeneous mixture was stirred for 4 hours, then the precipitate was filtered and washed with 1-propanol (2 mL). The product was dried at 45° C. in vacuo for 18 hours to give 1.71 g of Form 2 crystalline polymorph in a yield of 86.4%.

Method 2

Crystallization of the Form 2 crystalline polymorph from a solution in 1-propanol may also be facilitated by seeding with a crystal or crystals of the Form 2 crystalline polymorph, as follows. 1-Propanol (25.00 L/kg, 275.0 mL) was added to compound (I) (11.00 g). The mixture was stirred at 350 rpm at 25° C. The heterogeneous mixture was then warmed to 97° C. over 40 minutes (reflux temperature), kept for 5 minutes at 97° C., then cooled to 96° C. over 5 minutes, then kept for 1 hour at 96° C. The homogeneous, slightly orange solution was cooled to 85° C. over 15 minutes. The stirring speed was then decreased to 250 rpm and the solution was seeded with Form 2 crystalline polymorph (0.01 kg seed crystal/kg compound (I) starting material, 0.11 g). The mixture was stirred for 10 minutes at 85° C., then cooled to 22° C. over 8 h, using cubic cooling with a non-linear coefficient of 2.3. The heterogeneous mixture stirred for 10 hours at 22° C. before the precipitate was filtered. The product was washed with 1-propanol (1.00

L/kg, 8.84 g, 11.00 mL) then was dried at 45° C. (weekend; 72 hours) to give the Form 2 crystalline polymorph (9.5 g, 86.4%).

Method 3

The Form 2 crystalline polymorph may be prepared by slurrying the Form 1 crystalline polymorph in methanol, ethanol, 2-propanol, 1-propanol, acetone, ethyl acetate, acetonitrile, toluene, isopropylacetate, TBME, 2-butanone, DMSO, diethyl ether, MIBK, heptane, nitromethane, 10% water/ethanol, 10% water/acetonitrile or 10% water/2-propanol.

Method 4

The Form 2 crystalline polymorph may be prepared by slurrying compound (I) in amorphous form in methanol, ethanol, 2-propanol, 1-propanol, acetone, ethyl acetate, acetonitrile, toluene, isopropylacetate, TBME, 2-butanone, DMSO, diethyl ether, MIBK, nitromethane, 10% water/ethanol or 10% water/2-propanol.

Method 5

A scaled-up preparation of the Form 2 crystalline polymorph is as follows: 200 mg of Form 1 crystalline polymorph was weighed into a 20 ml scintillation vial. 50 volumes of methanol were added and the sample was slurried for 24 hours between 20° C. and 50° C. (4 hours at each temperature) with constant stirring at 500 rpm. The resulting material was filtered under vacuum and dried in the vacuum oven overnight at 40° C.

Example 4—Characterization of Compound (I) as the Form 2 Crystalline Polymorph

XRPD analysis of a sample of the Form 2 crystalline polymorph was undertaken using XRPD method 3 in the General procedures. The XRPD pattern obtained is shown in FIG. 5.

Figure 6:
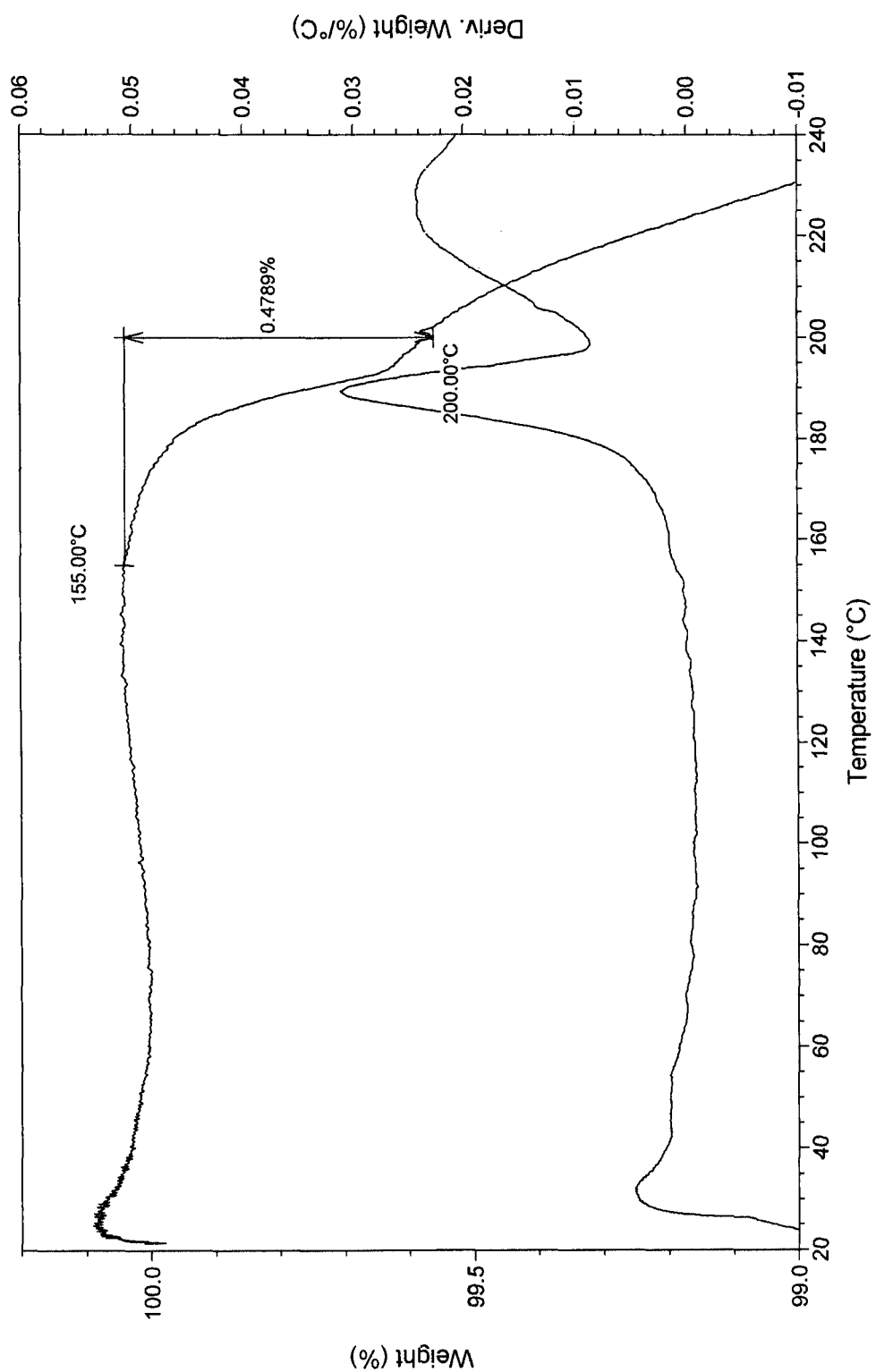
FIG. 6: shows a TGA analysis of a sample of the Form 2 crystalline polymorph (see Example 4).

TGA analysis of a sample of the Form 2 crystalline polymorph was undertaken using TGA method 2 in the General procedures. The data obtained are shown in FIG. 6 from which it is evident that the Form 2 crystalline polymorph showed a weight loss of ±0.5% from 155° C. up to 200° C.

Figure 7:
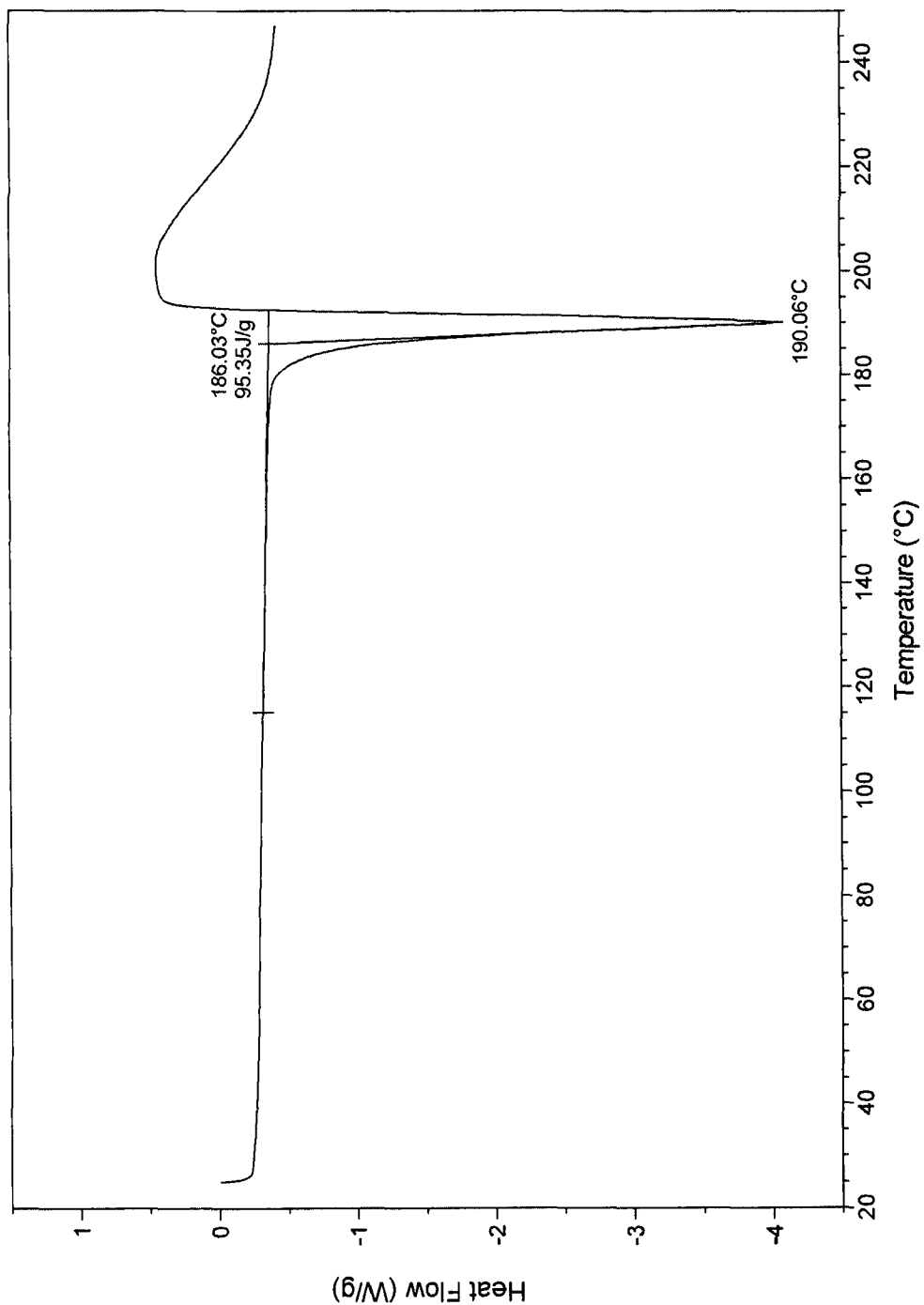
FIG. 7 shows a DSC analysis of a sample of the Form 2 crystalline polymorph (see Example 4).

DSC analysis on a sample of the Form 2 crystalline polymorph was undertaken using DSC method 2 in the General procedures. The data obtained are shown in FIG. 7 from which it is evident that the Form 2 crystalline polymorph showed melting with decomposition at 190.1° C. (peak maximum).

Figure 8:
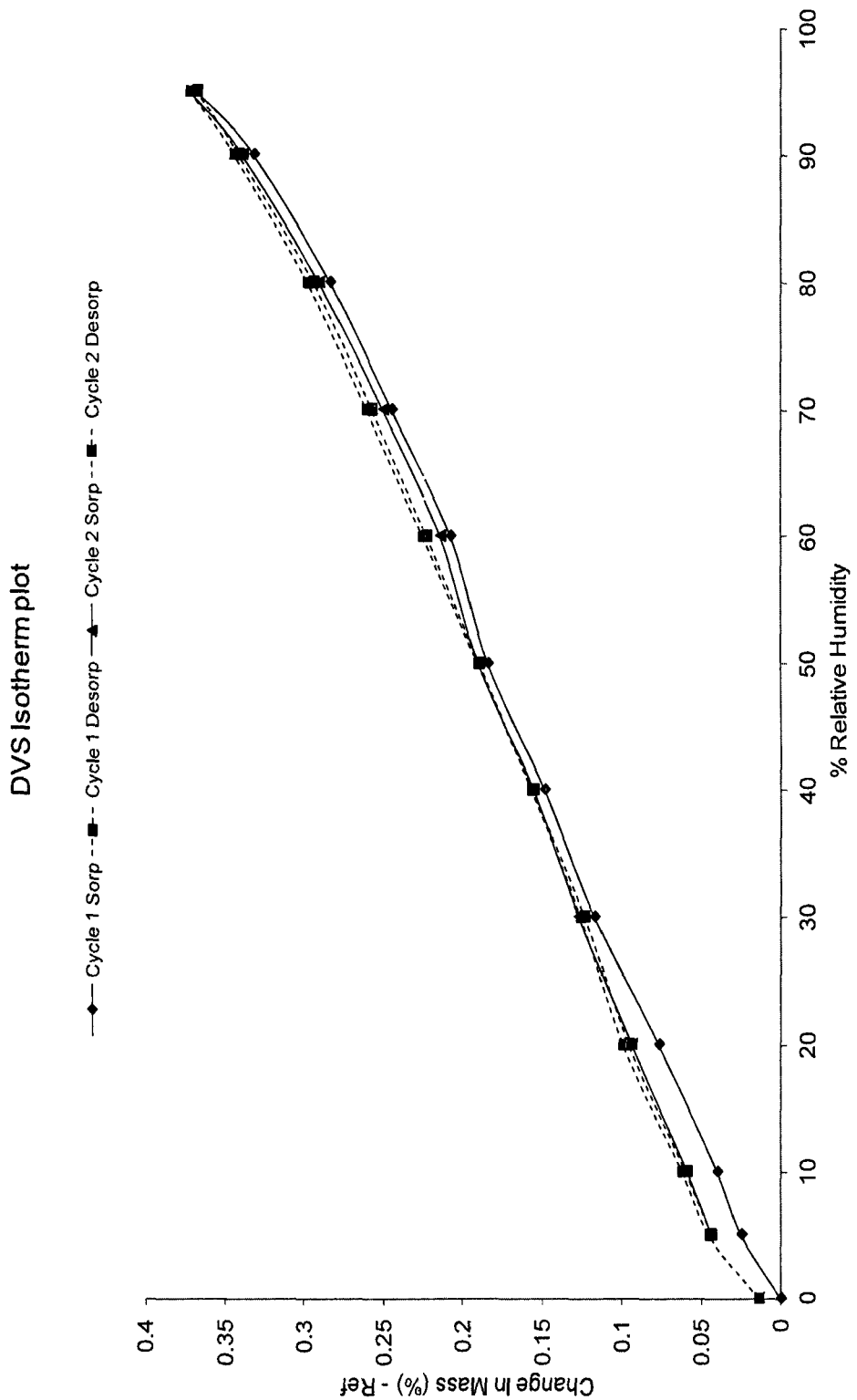
FIG. 8: is a DVS isotherm plot for a sample of the Form 2 crystalline polymorph (see Example 4).
Figure 9:
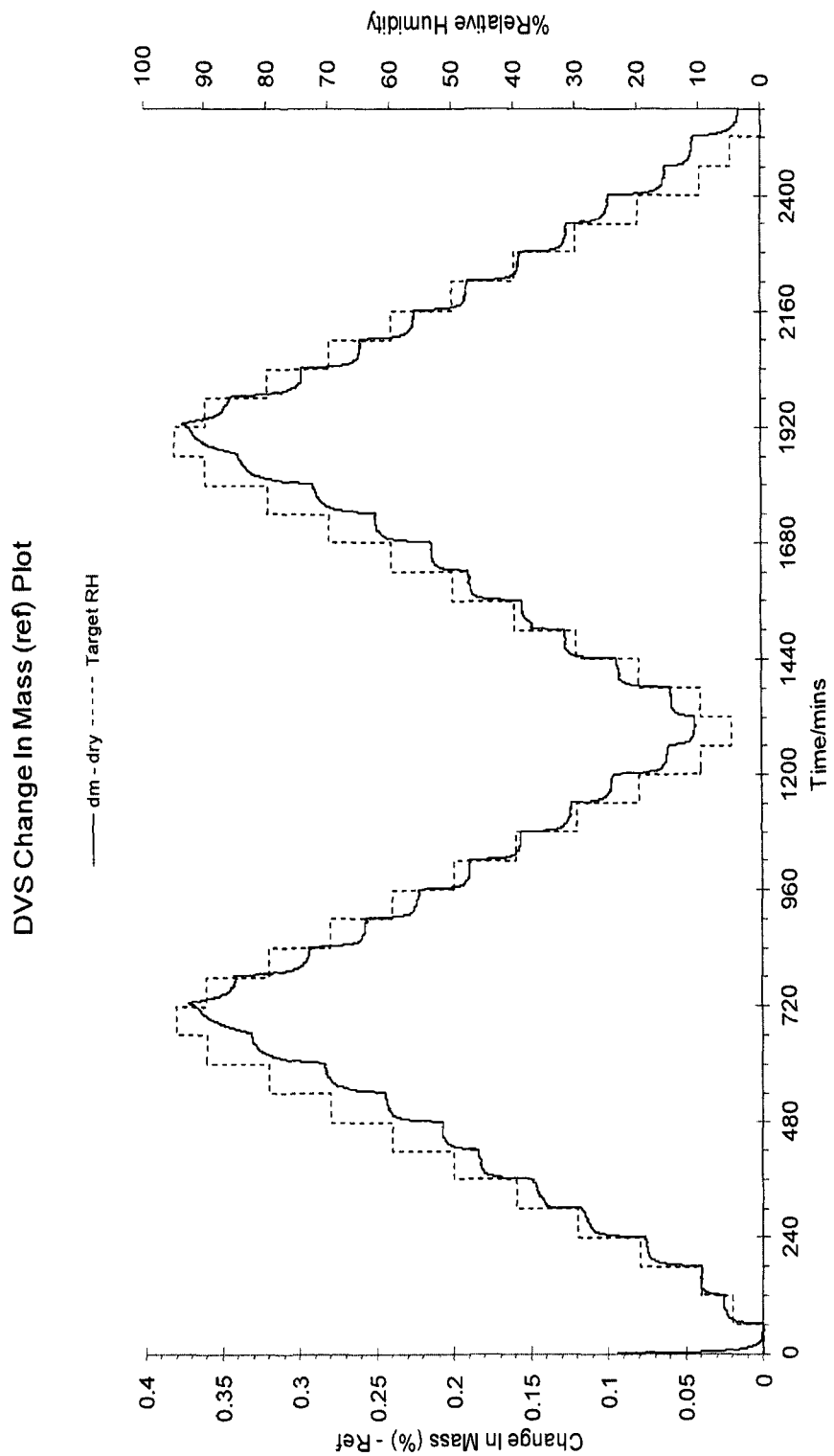
FIG. 9: is a DVS change in mass plot for a sample of the Form 2 crystalline polymorph (see Example 4).

A DVS isotherm plot of a sample of the Form 2 crystalline polymorph is shown in FIG. 8 and a DVS change in mass plot is shown in FIG. 9. The Form 2 crystalline polymorph was observed to absorb water gradually ±0.4% from 0% RH up to 95% RH and the water uptake was reversible, indicating that the Form 2 is not hygroscopic.

Figure 10:
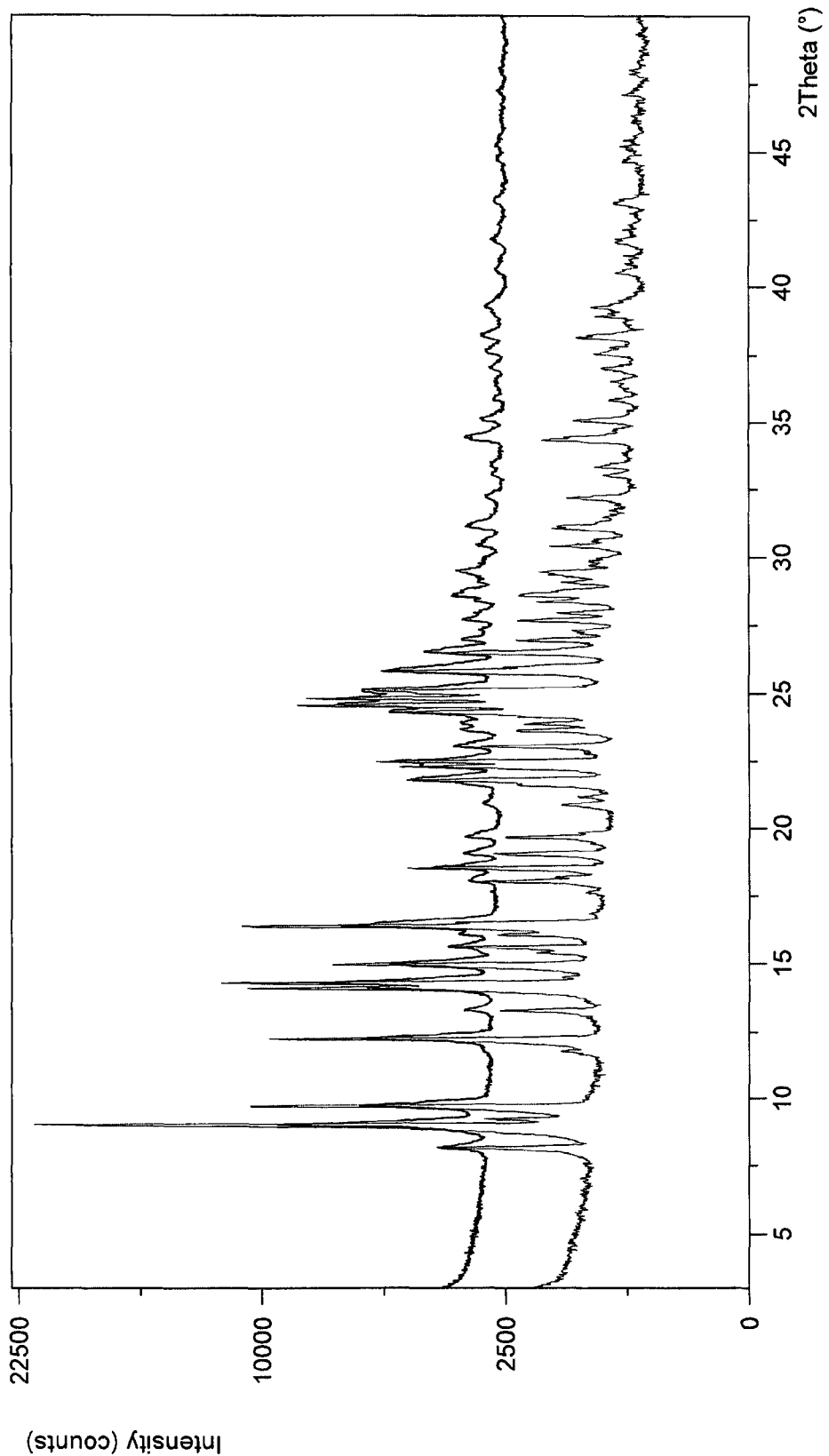
FIG. 10: shows XRPD patterns obtained before (bottom plot) and after (top plot) DVS analysis on a sample of the Form 2 crystalline polymorph (see Example 4)
Figure 11:
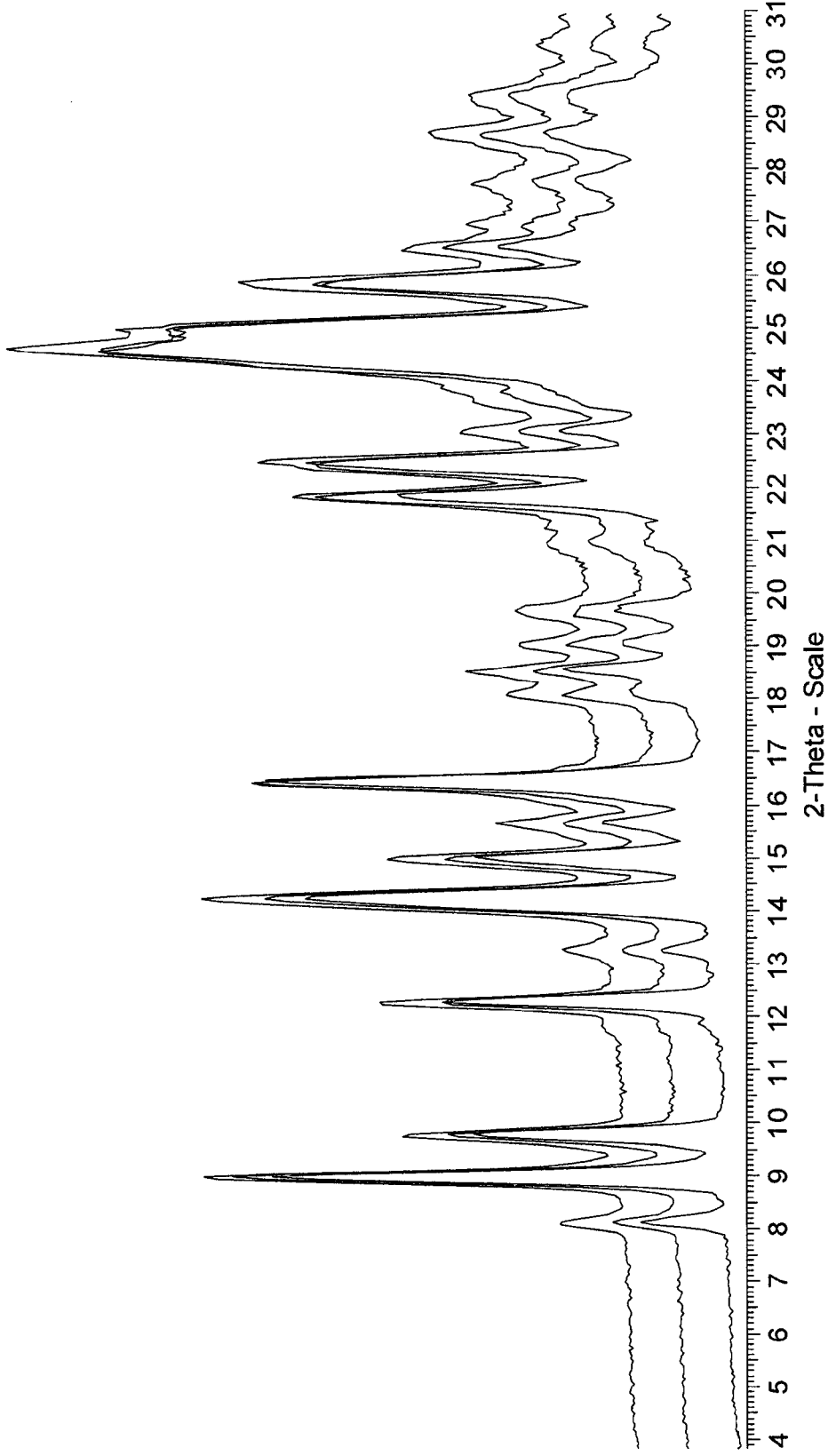
FIG. 11: shows XRPD patterns of a sample of the Form 2 crystalline polymorph obtained before (bottom plot) and after 1 week storage at 25° C./96% RH (middle plot) and 40° C./75% RH (top plot) (see Example 4).

A static stability study of a sample of the Form 2 crystalline polymorph demonstrated that the sample was stable to moisture with respect to solid form as no changes were noted by XRPD (using XRPD method 3 in the General Procedures) after the DVS analysis (see FIG. 10) and 1 week storage at 25° C./96% RH and 40° C./75% RH (see FIG. 11, using XRPD method 1 in the General Procedures).

Example 5—Stability of Micronized Compound (I) as the Form 2 Crystalline Polymorph Micronized Form 2 crystalline polymorph was prepared using a 5 cm Jetmill micronization device to produce the following particle size distribution: $D_{10}$=1.14 μm; $D_{50}$=1.94 μm and $D_{90}$=3.39 μm (the particle size distribution was determined using laser diffraction (Malvern Mastersizer instrument).

The micronized material was analyzed by TGA, XRPD, and DSC at time zero and after different conditions of storage. Samples were stored under the following conditions: (i) 7 weeks at RT/<5% RH; (ii) 7 weeks at RT/56% RH; (iii) 7 weeks at RT/75% RH; (iv) 7 weeks at 50° C.; and (v) 7 weeks at 40° C./75% RH.

The data shown in Table 3 indicate that the sample was crystallographically and thermodynamically stable as no significant changes were observed under the different conditions.

TABLE 3 stability data for the Form 2 crystalline polymorph (micronized)

| | TGA | | | | DSC | | |
|---|---|---|---|---|---|---|---|
| Conditions | <100 | <185° C. | XRD | IR | Max (° C.) | Extra (° C.) | Appearance |
| 0 days | 0.1 | 0.3 | REF | REF | 188.4 | 113.3 (17 J/g) | white |
| RT/<5% RH* | 0.1 | 0.3 | ~Ref | ~Ref | 188.6 | 113.8 (11 J/g) | white |
| RT/56% RH* | 0.1 | 0.4 | ~Ref | ~Ref | 188.5 | 113.7 (8 J/g) | white |
| RT/75% RH* | 0.2 | 0.4 | ~Ref | ~Ref | 188.7 | 113.7 (10 J/g) | white |
| 50° C.* | 0.0 | 0.3 | ~Ref | ~Ref | 187.8 | 119.8 (3 J/g) | white |
| 40° C./75% RH* | 0.1 | 0.2 | ~Ref | ~Ref | 188.5 | 117.4 (1 J/g) | white |

*for 7 weeks;
REF = crystalline reference;
~Ref = identical to reference

Example 6—Preparation of Compound (I) in Amorphous Form

Compound (I) in amorphous form was prepared by heating the Form 1 crystalline polymorph (obtained using the procedure of Example 2) to 120° C.

Example 7—Preparation of Compound (I) as the Form 3 Crystalline Polymorph

Method 1

The Form 3 crystalline polymorph may be prepared by slurrying compound (I) in amorphous form in dichloromethane.

Method 2

A scaled-up preparation of the Form 3 crystalline polymorph is as follows: 200 mg of the Form 1 crystalline polymorph was added to a 4 ml vial containing 5 volumes of dichloromethane. The sample was vortexed for 30 seconds. A further 5 volumes DCM were then added and the sample vortexed for another 30 seconds. The sample was filtered under vacuum and dried in a vacuum oven over the course of a weekend at 25° C.

Example 8—Characterization of Compound (I) as the Form 3 Crystalline Polymorph XRPD analysis of a sample of the Form 3 crystalline polymorph was undertaken using XRPD method 2 in the General Procedures. The XRPD pattern is shown in FIG. 12.

Figure 13:
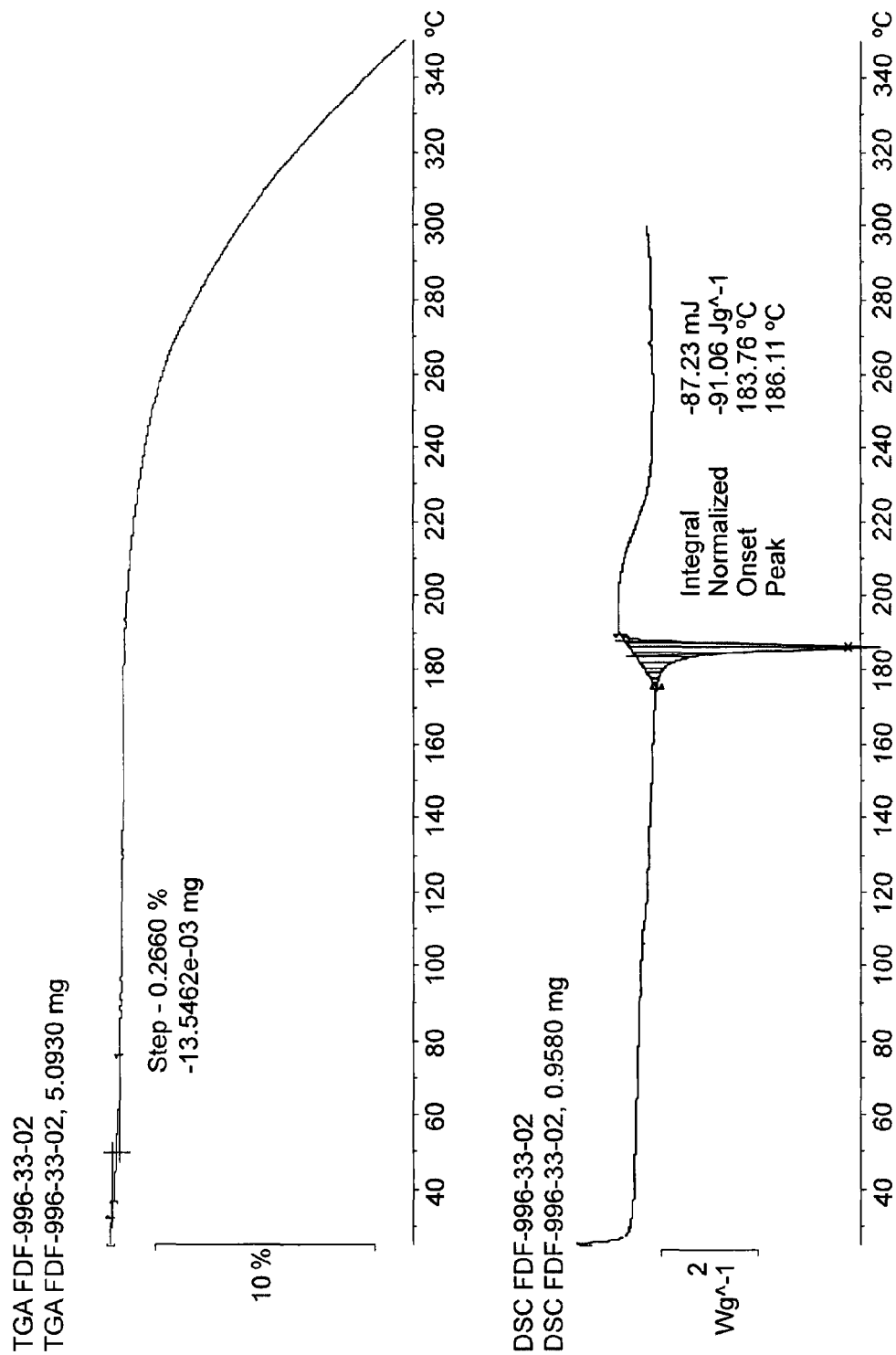
FIG. 13: shows a TGA (top plot) and DSC (bottom plot) analysis of a sample of the Form 3 crystalline polymorph (see Example 8).

TGA and DSC data (using TGA method 1 and DSC method 1 in the General procedures) obtained on a sample of Form 3 crystalline polymorph are shown in FIG. 13. The Form 3 crystalline polymorph melts with decomposition at about 186° C. (peak maximum; DSC—bottom plot).

Figure 14:
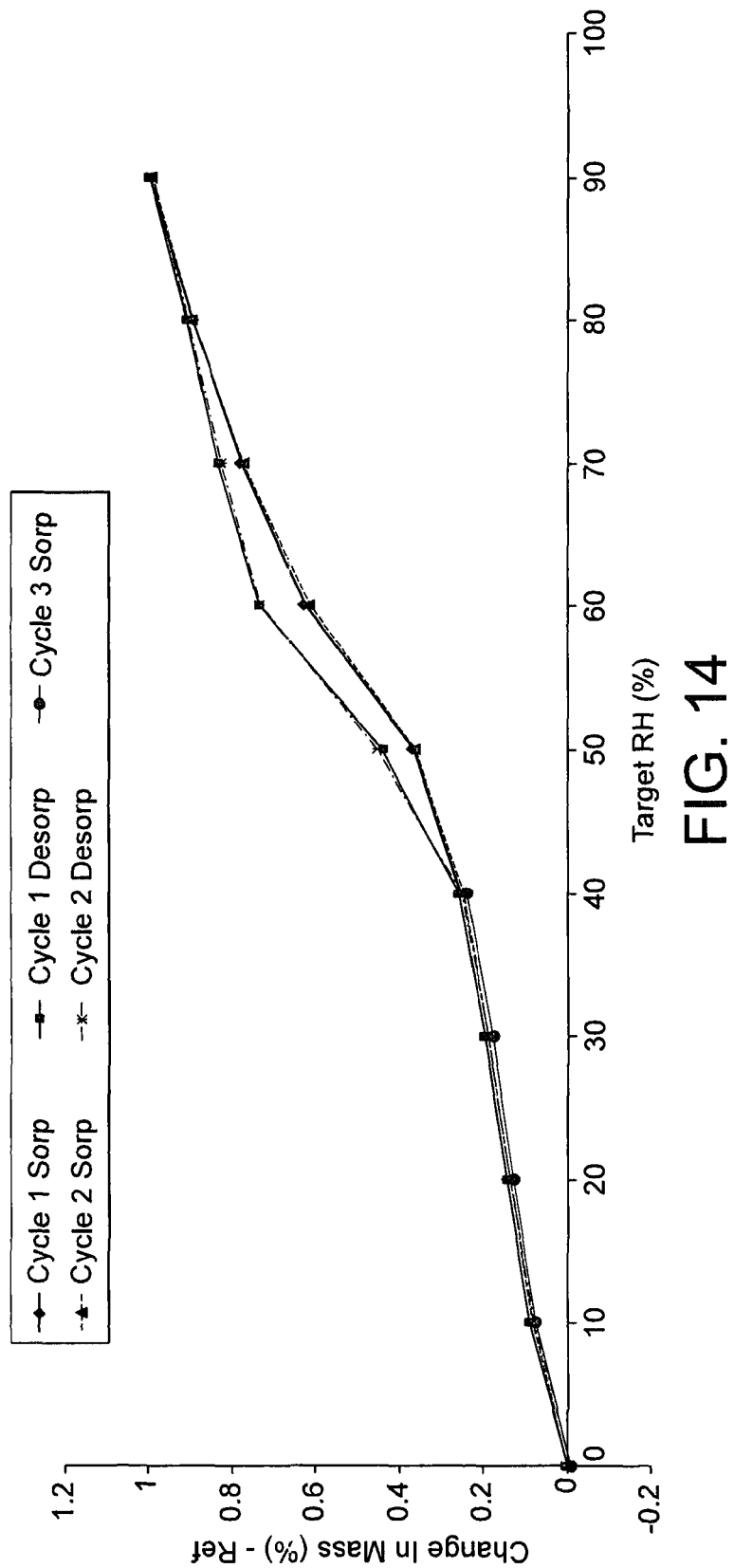
FIG. 14: is a GVS analysis on a sample of the Form 3 crystalline polymorph (see Example 8).

A GVS isotherm obtained on a sample of the Form 3 crystalline polymorph is shown in FIG. 14, where a 0.99% mass change from 0-90% RH was observed.

Figure 15:
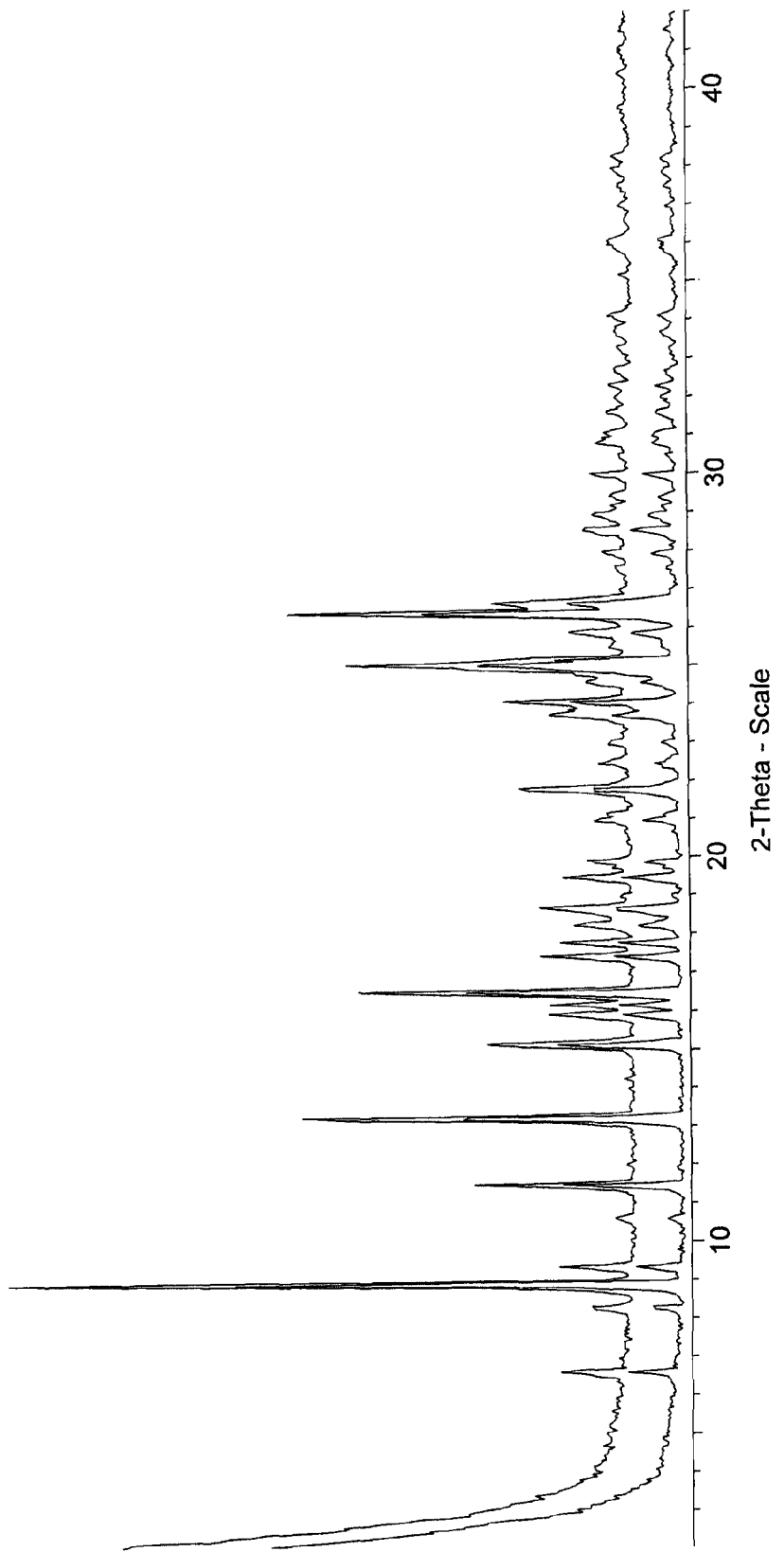
FIG. 15: shows XRPD patterns obtained before (bottom plot) and after (top plot) GVS analysis on a sample of the Form 3 crystalline polymorph (see Example 8).
Figure 16:
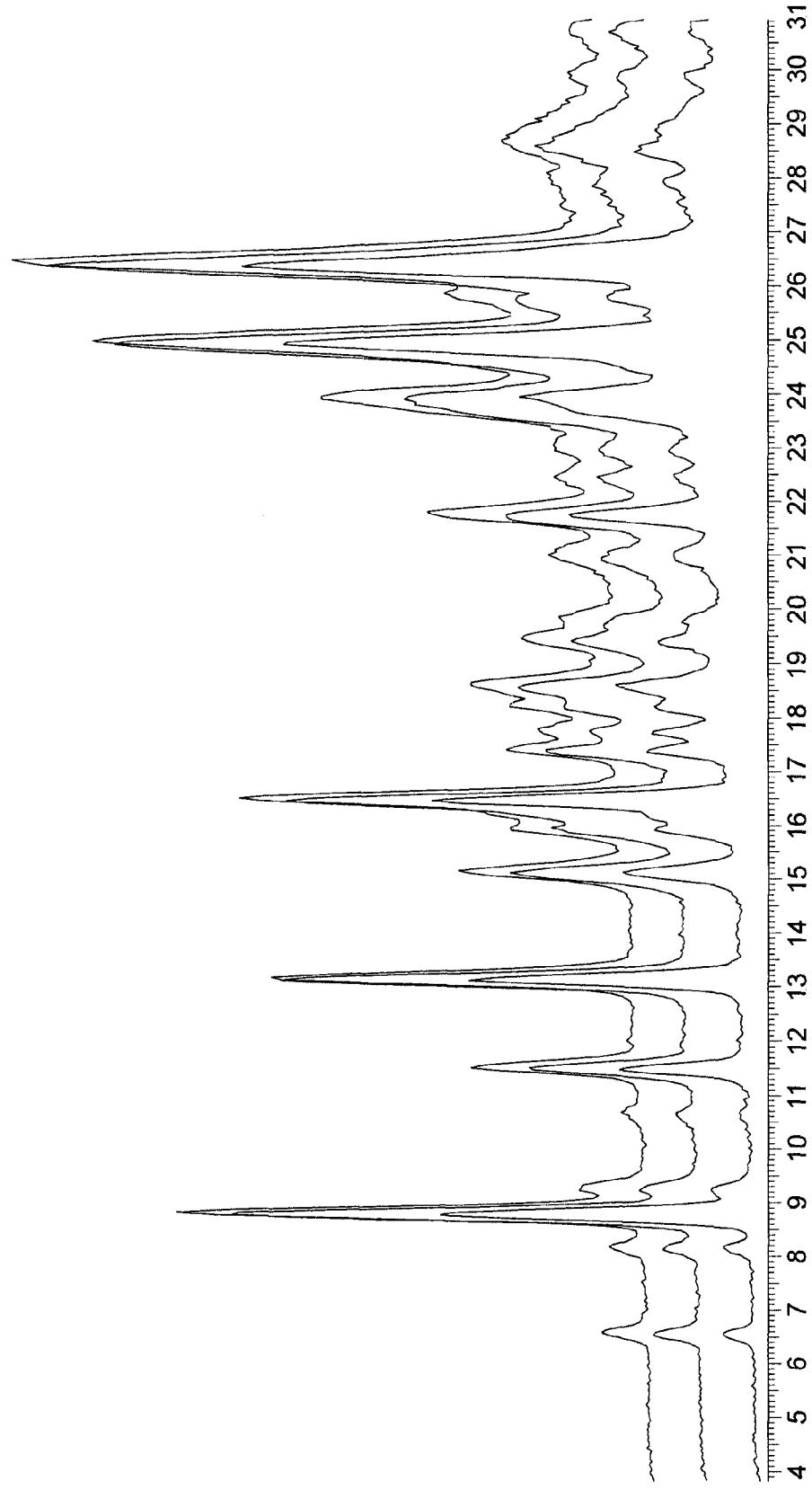
FIG. 16: shows XRPD patterns of a sample of the Form 3 crystalline polymorph obtained before (bottom plot) and after 1 week storage at 25° C./96% RH (middle plot) and 40° C./75% RH (top plot) (see Example 8).

A static stability study of a sample of the Form 3 crystalline polymorph demonstrated that the sample was stable to moisture with respect to solid form as no changes were noted by XRPD (using XRPD method 2 in the General procedures) after GVS analysis (see FIG. 15) and after 1 week storage at 25° C./96% RH and 40° C./75% RH (see FIG. 16; using XRPD method 1 in the General procedures).

Example 9—Preparation of Compound (I) as the Form 4 Pseudopolymorph

Compound (I) in the form of the Form 1 crystalline polymorph (20 mg) or compound (I) in amorphous form (20 mg) was weighed into a HPLC vial. THF was then added in increments at room temperature with shaking for 1 minute. The sample was then shaken (500 rpm) at 50° C. for 15 minutes before the next addition of THF. This process was continued until 80 volumes of THF had been added to obtain a solution. The solution was cooled from 50° C. to 5° C. at 0.1° C./min and held at 5° C. overnight. The solution was then left to evaporate in order to obtain a solid. The solid was filtered under vacuum, air dried (under vacuum) for 2 hours before being analyzed by XRPD using XRPD method 1 in the General procedures. The XRPD pattern of a sample of the solid obtained using compound (I) in amorphous form as starting material is shown in FIG. 17 and corresponds to the Form 4 pseudopolymorph. A sample of the solid obtained using the Form 1 crystalline polymorph as starting material was dried in a vacuum oven at 25° C. for >48 hours before being analyzed again by XRPD. Following this extended drying period the Form 4 crystalline polymorph was observed to have converted into compound (I) in amorphous form. As such, the Form 4 pseudopolymorph is a meta-stable solvate.

Example 10—Preparation of Compound (I) as the Form 5 Pseudopolymorph

Compound (I) in the form of the Form 1 crystalline polymorph (20 mg) or compound (I) in amorphous form (20 mg) was weighed into a HPLC vial. 1,4-dioxane was then added in increments at room temperature with shaking for 1 minute. The sample was then shaken (500 rpm) at 50° C. for 15 minutes before the next addition of 1,4-dioxane. This process was continued until 80 volumes of 1,4-dioxane had been added to obtain a solution. The solution was cooled from 50° C. to 5° C. at 0.1° C./min and held at 5° C. overnight. The solution was then left to evaporate in order to obtain a solid. The solid was filtered under vacuum, air dried (under vacuum) for 2 hours before being analyzed by XRPD using XRPD method 1 in the General procedures. The XRPD pattern of a sample of the solid obtained using compound (I) in amorphous form as starting material is shown in FIG. 17 and corresponds to the Form 5 psuedopolymorph. A sample of the solid obtained using the Form 1 crystalline polymorph as starting material was dried in a vacuum oven at 25° C. for >48 hours before being analyzed again by XRPD. Following this extended drying period the Form 5 pseudopolymorph did not change form. Further characterization was conducted to generate $^1$H NMR, TGA and DSC data (not shown) which showed that the Form 5 pseudopolymorph reverted back to compound (I) in amorphous form after solvent loss. As such, the Form 5 pseudopolymorph is a meta-stable solvate.

Example 11—Preparation of Compound (I) as the Form 6 Pseudopolymorph

Compound (I) in amorphous form (20 mg) was weighed into a HPLC vial. 10% water/acetonitrile was then added in increments at room temperature with shaking for 1 minute. The sample was then shaken (500 rpm) at 50° C. for 15 minutes before the next addition of 10% water/acetonitrile. This process was continued until 80 volumes of 10% water/acetonitrile had been added. The resulting slurry was left to mature between 25° C. and 50° C. (4 hours at each temperature) with shaking at 500 rpm for 2 days. The solid was then filtered under vacuum, air dried for 2 hours and analyzed by XRPD using XRPD method 1 in the General procedures. The XRPD pattern of a sample this material is shown in FIG. 17 and corresponds to the Form 6 pseudopolymorph. Following XRPD analysis the material was dried in a vacuum oven at 40° C. overnight. Following this extended drying period the Form 6 pseudpolymorph was observed to have lost solvent and converted into the Form 2 crystalline polymorph. As such, the Form 6 pseudopolymorph is a meta-stable solvate.

Example 12—Preparation of Compound (I) as a the Form 7 Pseudopolymorph

Compound (I) in amorphous form (20 mg) was weighed into a HPLC vial. 10% water/acetone was then added in increments at room temperature with shaking for 1 minute. The sample was then shaken (500 rpm) at 50° C. for 15 minutes before the next addition of 10% water/acetone. This process was continued until 80 volumes of 10% water/acetone had been added. The resulting slurry was left to mature between 25° C. and 50° C. (4 hours at each temperature) with shaking at 500 rpm for 2 days. The solid was then filtered under vacuum, air dried for 2 hours and analyzed by XRPD using XRPD method 1 in the General procedures. The XRPD pattern of a sample this material is shown in FIG. 17 and corresponds to the Form 7 pseudopolymorph. Following XRPD analysis the material was dried in a vacuum oven at 40° C. overnight. Following this extended drying period the Form 7 pseudopolymorph was observed to have lost solvent and converted into the Form 2 crystalline polymorph. As such, the Form 7 pseudopolymorph is a meta-stable solvate.

Example 13—Thermodynamic Stability of the Form 2 and Form 3 Crystalline Polymorphs and Their Inter-Conversion Competitive slurry experiments were performed on 50:50 mixtures of the Form 2 and Form 3 crystalline polymorphs. 50 volumes of solvent were added and the samples were stirred (300 rpm) at a set temperature for 3 days. All samples were then filtered under vacuum and air dried for 30 minutes prior to XRPD analysis.

The results of the slurry experiments are summarized in Table 4 below:

TABLE 4

Competitive slurry results

| Solvent | Temperature | Observation | XRPD Result |
| --- | --- | --- | --- |
| Chloroform | 50° C. | clear solution and solid | Form 2 |
| Chloroform | 25° C. | slurry | Form 2 |
| Chloroform | 5° C. | slurry | Form 2 |
| Acetonitrile | 50° C. | clear solution and solid | Form 2 |
| Acetonitrile | 25° C. | slurry | Form 2 |
| Acetonitrile | 5° C. | slurry | Form 2 |
| 10% water/ACN | 50° C. | clear solution and solid | Form 2 |
| 10% water/ACN | 25° C. | slurry | Form 2 |
| 10% water/ACN | 5° C. | slurry | Form 2 |
| Ethanol | 25° C. | slurry | Form 2 |
| Ethanol | 40° C. | slurry | Form 2 |
| Ethanol | 60° C. | clear solution and solid | Form 2 |
| Acetone | 25° C. | slurry | Form 2 |
| Acetone | 40° C. | slurry | Form 2 |
| Acetone | 60° C. | clear solution and solid | Form 2 |
| Ethyl acetate | 25° C. | slurry | Form 2 |
| Ethyl acetate | 40° C. | slurry | Form 2 |
| Ethyl acetate | 60° C. | clear solution and solid | Form 2 |

All competitive slurry experiments resulted in Form 2 indicating that this is the more stable thermodynamic form.

Example 14—In Vitro and In Vivo Screening Methodology and Results

In Vitro Screening
Biological Testing: Experimental Methods
Enzyme Inhibition Assay The PI3K enzymes catalyse the phosphorylation of phosphatidylinositol 4,5-biphosphate (PIP2) to phosphatidylinositol 3,4,5-triphosphate (PIP3) in the presence of ATP and $Mg^{2+}$ ions. The PIP3 product can be detected by displacement of biotin-PIP3 from energy transfer complexes consisting of europium labelled anti-GST monoclonal antibody, a GST-tagged Pleckstrin homology (PH) domain, biotinylated PIP3 and streptavidin-allophycocyanin (APC) by the time-resolved fluorescence resonance energy transfer (TR-FRET) (HTRF®PI3K enzyme assay, Millipore). Excitation, at 330 nm, of europium in the complex results in an energy transfer to the APC and a fluorescent emission at 665 nm although europium itself emits at its characteristic wavelength of 620 nm. The PIP3 product formed by PI3K activity displaces biotin-PIP3 from the complex and results in a loss of energy transfer (decreasing signal).

The compound to be tested was added, at the desired final concentrations, to a mixture of PIP2 substrate and a recombinant PI3K enzyme (either α, β or δ isoforms, ex Millipore, or γ isoform [p110γ+p101 construct], ex United States Biological, Swampscott, Mass.) and the mixture incubated for 2 hr at RT. Following this incubation period, ATP (10 µM) was added to the enzyme/compound/PIP2 substrate mixture and the resulting mixture was incubated for a further 30 min at RT. A stopping solution containing biotinylated PIP3 and the detection mix containing the GST tagged GRP1 pleckstrin homology (PH) domain and fluorophores were then added and the mixture was incubated at RT for 15-18 hr, prior to detection in a fluorescence microplate reader (Synergy 4, BioTek UK, Bedfordshire, UK).

The results were calculated according to the formula: APC signal (emission at 665 nm)/europium signal (emission at 620 nm)×$10^4$. The percentage inhibition of each reaction was calculated relative to DMSO treated control, and the 50% inhibitory concentration ($IC_{50}$ value) then calculated from the concentration-response curve.

PI3K δ Cell Based Assay

As a means of assessing PI3K δ activation in response to stimuli, the phosphorylation status of the protein, Akt, a downstream product of PI3Kδ, signaling was determined.

U937 cells, obtained from a human, leukemic, monocyte lymphoma cell line, were differentiated to macrophage-type cells by incubation with PMA (100 ng/mL) for 48 to 72 hr. Cells were then pre-incubated with either the test compound or vehicle for 2 hr and were then stimulated briefly by exposure to $H_2O_2$ (10 mM, 5-7 min) and the reaction stopped by replacing the media with 4% formaldehyde solution. Endogenous peroxide activity and formaldehyde were inactivated by incubating with quenching buffer (0.1% sodium azide, 1% $H_2O_2$ in PBS with 0.1% Triton X-100) for 20 min. The cells were washed with buffer (PBS containing 0.1% Triton X-100) and were incubated with blocking solution (1% BSA in PBS) for 1 hr and were then re-washed with buffer and incubated overnight with either anti-pAkt antibody or anti-pan-Akt antibody (both from Cell Signaling Technology). After washing with buffer (PBS containing 0.1% Triton X-100), cells were incubated with an HRP-conjugated secondary antibody (Dako) and the resultant signal was determined colorimetrically (OD: 450 nm with a reference wavelength of 655 nm) using TMB substrate (substrate reagent pack supplied by R&D Systems, Inc.).

This reaction was stopped by the addition of $H_2SO_4$ solution (100 µL). Cells were then washed with buffer (PBS containing 0.1% Triton X-100) and 5% crystal violet solution (100 µL) was applied for 30 min. After washing with buffer (PBS containing 0.1% Triton X-100) 1% SDS (100 µL) was added to each well and the plates were shaken lightly for 1 hr prior to measuring the absorbance at 595 nm (Varioskan® Flash, Thermo-Fisher Scientific). The measured $OD_{450-655}$ readings were corrected for cell number by dividing the $OD_{450-655}$ by the $OD_{595}$ readings. The ratio of pAkt signal to total Akt signal was used to quantitate the extent of PI3K δ activation. The percentage inhibition for each well was calculated relative to a 10 µg/mL standard control (LY294002) set to 100% inhibition versus $H_2O_2$ only controls as 0% inhibition. The $IC_{50}$ values were calculated from the concentration-response curves generated by the serial dilutions of the test compounds.

PI3K γ Cell Based Assay

As a means of assessing the activation of PI3K γ in response to stimuli, the phosphorylation status of the protein, Akt, a downstream product of PI3K γ signalling, was determined following stimulation with MCP-1.

U937 cells were differentiated to macrophage-type cells by incubation with PMA (100 ng/mL) for 48 to 72 hr. Cells were then pre-incubated with either the test compound or vehicle for 2 hr and were then stimulated briefly with MCP-1

(10 nM, 1 min) and the reaction stopped by replacing the media with 4% formaldehyde solution. Endogenous peroxide activity and formaldehyde were inactivated by incubating with quenching buffer (0.1% sodium azide, 1% $H_2O_2$ in PBS with 0.1% Triton X-100) for 20 min. The cells were washed with buffer (PBS containing 0.1% Triton X-100) and were incubated with blocking solution (1% BSA in PBS) for 1 hr and were then re-washed with buffer and incubated overnight with either anti-pAkt antibody or anti-pan-Akt antibody (both from Cell Signaling Technology). After washing with buffer (PBS containing 0.1% Triton X-100), cells were incubated with an HRP-conjugated secondary antibody (Dako) and the resultant signal was determined colorimetrically (OD: 450 nm with a reference wavelength of 655 nm) using TMB substrate (substrate reagent pack supplied by R&D Systems, Inc.).

This reaction was stopped by addition of 1N $H_2SO_4$ solution (100 μL). Cells were then washed with buffer (PBS containing 0.1% Triton X-100) and 5% crystal violet solution (100 μL) was applied for 30 min. After washing with buffer (PBS containing 0.1% Triton X-100) 1% SDS (100 μL) was added to each well and the plates were shaken lightly for 1 hr prior to measuring the absorbance at 595 nm (Varioskan® Flash, Thermo-Fisher Scientific). The measured $OD_{450-655}$ readings were corrected for cell number by dividing the $OD_{450-655}$ by the $OD_{595}$ readings. The ratio of pAkt signal to total Akt signal was used to quantitate the extent of PI3K γ activation. The percentage inhibition for each well was calculated relative to a 10 μg/mL standard control (LY294002) set to 100% inhibition versus MCP-1 only controls as 0% inhibition. The $IC_{50}$ values were calculated from the concentration-response curves generated by the serial dilutions of the test compounds using XL-Fit (idbs, Guildford, UK).

Superoxide Anion Production Assay

As a means of assessing PI3Kδ dependent cell function, superoxide anion production in IFNγ-primed U937 cells was evaluated by a chemiluminescence assay. The U937 cells (purchased from ATCC, Manassas, Va.) were maintained in RPMI 1640 (Invitrogen Ltd., Paisley, UK) with 10% FCS at 37° C. The cells were suspended at a density of $10^7$ cells/mL in 40 mL 10% FCS RPMI 1640, and treated with 20 μL of 100 μg/mL IFNγ solution (final concentration: 50 ng/mL), and incubated at 37° C., 5% $CO_2$ for 4 days.

IFNγ-primed U937 cells were seeded at $0.2 \times 10^6$ cells/well in a 96-well plate, and pre-incubated with test compounds for 2 hr in starvation media (0.5% FCS RPMI1640-phenol red free). Zymosan A (10 mg) from Saccharomyses cerevisiae (ex Sigma-Aldlich) was resuspended in 1 mL of 150 mM NaCl and boiled at 100° C. for 15 min. After boiling, Zymosan particles were washed with 1 mL of PBS twice, and incubated with 0.5 mL of BioParticles™ opsonized reagents (Life technologies) for 60 min at 37° C. Cells were treated with a mixture of Zymosan particle solution (10 μL), assay buffer (85 μL), luminol (2.5 μL) and enhancer solution (2.5 μL), which are all provided (apart from Zymosan) in the Superoxide Anion Assay Kit (#CS1000, Sigma-Aldrich Ltd, Poole, UK). Chemiluminescence indicating released superoxide anion was measured every 15 min up to 60 min by luminometric measurement (Varioskan® Flash, Thermo-Fisher Scientific).

The data at 60 min after incubation was used for analysis. The percentage inhibition for each well was calculated relative to a 10 μg/mL IC87114, a standard PI3Kδ inhibitor, set to 100% inhibition versus control as 0% inhibition. The relative $EC_{50}$ values were calculated from the concentration-response curves generated by the serial dilutions of the test compounds using XL-Fit (idbs, Guildford, UK).

Cytostim-Induced Cytokine Production in PBMCs

As a means of assessing PI3Kδ-dependent cell function, cytostim-induced IL-4, IL-5, IL-13 and IFNγ production in PBMCs were evaluated by Luminex multiplex assay. All healthy volunteers were recruited by Quintiles Limited (London, UK), and blood samples were delivered to Respivert Ltd. This study was approved by the local Ethics Committee, and all subjects gave written informed consent.

PBMC suspensions (200 μL; $2 \times 10^6$ cells/mL) were added to a 96-well plate. Cells were treated with either test compounds in neat DMSO or DMSO as vehicle (2 μL) and incubated at RT for 1 hr. Cytostim (Miltentyi Biotec, Surrey, UK) was introduced at a ratio of 1:50 and the cells were incubated for 20 hr (37° C.; 5% $CO_2$). Plates were spun at 500×g for 5 min and the supernatant collected. A high sensitivity cytokine magnetic bead kit (#HSCYTMAG-60SK, Millipore, Watford, UK) was used to measure the four analytes (IL-4, IL-5, IL-13 and IFNγ) by Luminex as follows: The magnetic antibody beads were multiplexed and incubated in a 96-well plate with standard, media only or sample (50 μL) overnight with shaking at 4° C. After washing twice with Millipore wash buffer provided in the kit using a magnetic plate washer, the beads were incubated for 1 hr with detection antibody (50 μL) with shaking at RT. A streptavidin-phycoerythrin solution provided in the kit was added for 30 min with shaking at RT. After washing, the beads were re-suspended in sheath fluid (150 μL) and analysed immediately. The Luminex system was set up to count 50 beads and the amount of each analyte in the supernatant was calculated against a standard curve. The $IC_{50}$ values were determined from concentration-inhibition curves using XL-Fit (IDBS, Guildford, UK)

Chemotaxis to MCP1

As a means of assessing PI3K γ dependent cell function, THP1 cell chemotaxis to MCP-1 was evaluated using a 48 well-chemotaxis chamber. THP1 cells from a human leukemic monocyte lymphoma cell line, (purchased from ATCC Manassas, Va.) were maintained in RPMI 1640 (Invitrogen Ltd., Paisley, UK) with 10% FCS at 37° C. Cells were re-suspended in 0.5% BSA/RPMI1640 ($2 \times 10^6$ cells/mL) and incubated for 10 min at 37° C., 5% $CO_2$. Cell suspension aliquots (500 μL) were then treated either with compounds in neat DMSO or with DMSO as vehicle (2.5 μL) for 1 hr (37° C., 5% $CO_2$).

MCP1 (50 nM) was prepared in 0.5% BSA/RPMI1640. MCP1 solution (50 μL) was added to each well in the bottom plate of a 48-well chemotaxis chamber (AP48, NeuroProbe Inc., Gaithersburg, Md.). A polycarbonate membrane (8 μm) was mounted on the bottom chamber, and then the top plate was mounted on the bottom chamber and filter membrane. Cell suspension aliquots (50 μL) were treated with compounds or vehicle before being added into the top chamber carefully, and 0.5% BSA RPMI1640 (50 μL) was applied on top. The chamber was then left for 2 hr (37° C., 5% $CO_2$). The membrane was then carefully removed and sample (25 μL) from the bottom chamber was transferred to a new 96 well plate.

A solution of MTT (50 μL) in 10% FCS phenol red-free RPMI1640 was added to each well, and the plate was incubated for 2 hr (37° C., 5% $CO_2$). Neat DMSO (100 μL) was added to each well to extract formazan formed from MTT and the plates were shaken lightly for 1 hr prior to measuring the absorbance at 595 nm (Varioskan® Flash, Thermo-Fisher Scientific). Values were compared to inhibition by AS604850 (10 μg/mL), a selective PI3Kγ inhibitor, to calculate the relative percent inhibitions. Relative $EC_{50}$ values were determined from concentration-inhibition curves using XL-Fit (idbs, Guildford, UK).

CXCL8 Release from Neutrophils Obtained from COPD Patients

The effects of treatment on CXCL8 release from neutrophils obtained from COPD patients were evaluated by an ELISA assay. All patients were recruited by Quintiles Limited (London, UK), and blood samples were delivered to Respivert Ltd. This study was approved by the local Ethics Committee, and all subjects gave written informed consent. Whole blood (30 mL) was mixed gently with ACD (5 mL; comprising: 7.36 g citric acid, 14.71 g sodium citrate, 9.91 g dextrose in 250 ml sterile, double distilled water) and 6% dextran (15 mL; diluted in 0.9% NaCl) to remove the red blood cells. The tubes were incubated at RT for 45 min, and the supernatant (white cell rich fraction) was then collected, leaving the red blood cells.

This fraction was centrifuged (10 min at 1200 rpm, 4° C.) with low braking. The supernatant was aspirated and the pellet was re-suspended in ice-cold, sterile double distilled $H_2O$ (10 mL), and 0.6 M KCl (4 mL) was added 30 seconds later. The cell suspension was diluted with sterile PBS (to a final volume of 50 mL) and then centrifuged at 1500 rpm for 5 min. The supernatant was aspirated and the pellet re-suspended in PBS (2.5 mL), and two tubes from the same donor were pooled into one.

This cell suspension was carefully layered on top of 5 mL of Ficoll-Paque™ premium (GE Healthcare Bio Science AB, Uppsala, Sweden) using a Pasteur pipette, and then centrifuged (30 min at 1500 rpm with low braking). The isolated neutrophils at the bottom of the tubes were re-suspended in RPMI-1640 medium (Gibco, Paisley, UK) containing 5% FCS and seeded at a density of $4\times10^5$ cells/well in a 96 well plate. The cells were incubated for 30 min (37° C.; 5% $CO_2$) before treatment was begun.

Neutrophils were pre-incubated with test compounds or with DMSO vehicle for 1 hr and then stimulated with TNFα (10 ng/mL). Cell free supernatant was collected at 3 hr after TNFα stimulation, and CXCL8 was measured by ELISA using DuoSet ELISA development kit (R&D systems, Abingdon, UK). The $IC_{50}$ values reported were determined from concentration-inhibition curves using XL-Fit (IDBS, Guildford, UK).

MTT Assay

PMA-differentiated U937 cells were pre-incubated with test compound (10 µg/mL) or vehicle for 4 hr in 5% FCS or 10% FCS for 24 hr. The supernatant was replaced with new media (200 µL) and MTT stock solution (10 µL, 5 mg/mL) was added to each well. After 1 hr incubation, the media were removed, 200 µL of DMSO was added to each well and the plates were shaken lightly for 1 hr prior to reading the absorbance at 550 nm. The percentage loss of cell viability was calculated for each well relative to vehicle (0.5% DMSO)-treatment.

In Vivo Screening: Pharmacodynamics and Anti-inflammatory Activity

LPS-Induced Airway Neutrophil Accumulation in Mice

Non-fasted BALB/c mice (6-8 weeks old) were dosed with vehicle or with test compound by intra-tracheal administration (dose volume 20 µL) at time points T=−2 hr, −8 hr, or −12 hr with respect to the start of LPS treatment. The LPS was prepared in a solution of 0.5 mg/mL and aerosolised using a De Vibliss ultrasonic nebuliser 2000 (7 mL during 30 min exposure). At eight hr after LPS challenge, the trachea was cannulated and bronchoalveolar lavage fluid (BALF) extracted by infusing and then withdrawing PBS (1 mL) into the lungs via the tracheal catheter. This procedure was repeated to give a yield of approximately 2 mL lavage fluid. Total cell numbers in the BALF samples were measured using a haemocytometer. Cytospin smears of the BALF samples were prepared by centrifugation at 1200 rpm for 2 min at RT and stained using a DiffQuik stain system (Dade Behring) for differential cell counts. Cells were counted using oil immersion microscopy. Data are expressed as neutrophil number of cells per mL of BALF (mean±S.E.M).

LPS-Induced Airway Neutrophil Accumulation in Rats

Non-fasted rats were dosed with either vehicle or the test compound by intra-tracheal administration (dose volume 100 µL) at time points T=−2 h, −8 h, or −12 h with respect to the start of LPS treatment. The LPS solution (0.3 mg/mL) was aerosolised using a De Vibliss ultrasonic nebuliser 2000 (7 mL during 30 min). At eight hr after LPS challenge, the trachea was cannulated and bronchoalveolar lavage fluid (BALF) extracted by infusing and then withdrawing PBS (1 mL) into the lungs via the tracheal catheter. This procedure was repeated to provide approximately 2 mL of lavage fluid.

Total cell numbers in the BALF samples were measured using a Countess automated cell counter (Invitrogen). Cytospin smears of the BALF samples were prepared by centrifugation at 1200 rpm for 2 min at RT and stained using a DiffQuik stain system (Dade Behring) for differential cell counts. Cells were counted using oil immersion microscopy. Data are expressed as neutrophil number of cells per mL of BALF (mean±S.E.M).

Ovalbumin-Induced Airway Eosinophil and Neutrophil Accumulation in Mice

BALB/c mice (6-8 weeks old) were immunized with OVA (10 µg/mouse i.p.) on days 0 and 7. In order to elicit a local inflammatory response in the lung, mice were repeatedly challenged between days 13-15 with a nebulised solution of ovalbumin (10 mg/mL, 30 min exposure, De Vilibiss Ultra-neb 2000). On day 17 each animal received via intra-tracheal administration of either vehicle or test compound 2 hr prior to the final OVA challenge. Animals were anaesthetized 8 hr later before undergoing a tracheotomy. BAL was obtained by instilling PBS (1 mL) into the lungs, which was then withdrawn. This procedure was repeated to provide approximately 2 mL of lavage fluid. Total cell numbers in the BALF samples were measured using a haemocytometer. Cytospin smears of the BALF samples were prepared by centrifugation at 200 rpm for 5 min at RT and stained using a DiffQuik stain system (Dade Behring) for differential cell counts. Cells were counted using oil immersion microscopy. Data is expressed as differential number of cells per mL of nasal lavage fluid (mean±S.E.M).

Poly-I:C-Induced Cell Accumulation in Mice

Specific pathogen-free A/J mice (males, 5 weeks old) were dosed with poly (I:C)-LMW (1 mg/mL, 40 µL) (InvivoGen, San Diego, Calif., USA) intranasally twice daily for 3 days under anaesthesia (3% isoflurane). Test substances were dosed intra-nasally (50 µL in 10% DMSO/isotonic saline vehicle) 2 hr before each poly-I:C treatment. At 24 hr after the last poly-I:C challenge, animals were anesthetized, the trachea was cannulated and bronchial alveolar lavage (BAL) was obtained by instilling into and then withdrawing from the lungs, isotonic saline (100 mL/kg). Total cell numbers in the BALF samples were measured using a haemocytometer under a phase-contrast microscope.

The proportions of alveolar macrophages and neutrophils were determined by FACS analysis using anti-mouse MOMA2-FITC (macrophage) or anti-mouse 7/4-FITC (neutrophil). Cells were suspended in PBS and incubated with anti-MOMA2-FITC (2 μg/mL, Catalogue no SM065F, Acris Antibodies GmbH, Herford, Germany) or anti-7/4-FITC (2 μg/mL, Catalogue no CL050F, Acris Antibodies GmbH, Herford, Germany) for 30 min at 30° C., and then counterstained with propidium iodide (2 μg/mL) to allow exclusion of necrotic cells. The cells were washed with PBS, and transferred to FACS tubes. Samples was set in a flow cytometer (ALTRA II; Beckman Coulter Japan, Tokyo, Japan), and a single-parameter FL2 [PMT2] (FITC) histogram with log x-axis was plotted to illustrate relative intensity of FITC. Data files were stored for subsequent analysis using Kaluza analysis software (ver. 1.2) to calculate the proportion of each cell type.

Cigarette Smoke Model

A/J mice (males, 5 weeks old) were exposed to cigarette smoke (4% cigarette smoke, diluted with compressed air) for 30 min/day for 11 days using a Tobacco Smoke Inhalation Experiment System for small animals (Model SIS-CS; Sibata Scientific Technology, Tokyo, Japan). Test substances were administered once daily for 3 days after the final cigarette smoke exposure (intra-nasal dose comprising 35 μL of solution in 50% DMSO/isotonic saline).

At 12 hr after administration of the last dose, animals were anesthetized, the trachea was cannulated and bronchial alveolar lavage (BAL) was carried out by the instillation into and then withdrawal from the lungs, of PBS (100 mL/kg). Total cell numbers in the BALF samples were measured using a haemocytometer under a phase-contrast microscope. The proportions of alveolar macrophages and neutrophils were determined by FACS analysis using anti-mouse MOMA2-FITC (macrophage) or anti-mouse 7/4 (neutrophil).

Cells were suspended in PBS and were incubated with anti-MOMA2-FITC (2 μg/mL, Catalogue no SM065F, Acris Antibodies GmbH, Herford, Germany) or anti-7/4-FITC (2 μg/mL, Catalogue no CL050F, Acris Antibodies GmbH, Herford, Germany) for 30 min at 30° C., and also counterstained with propidium iodide (2 μg/mL) to allow exclusion of necrotic cells. The cells were washed with PBS, and transferred to FACS tubes. Samples was set in a flow cytometer (ALTRA II; Beckman Coulter Japan, Tokyo, Japan), and a single-parameter FL2[PMT2] (FITC) histogram with log x-axis was plotted to illustrate relative intensity of FITC.

Data files are stored for subsequent analysis using Kaluza analysis software (ver. 1.2) to calculate the proportion of each cell type. The levels of CXCL1(KC), MCP1, TNFα, IL-17 or osteopontin in BALF were determined using Quentikine® mouse KC, MCP1, TNFα, IL-17 or osteopontin ELISA kit (R&D systems, Inc., Minneapolis, Minn., USA). The presence of malondialdehyde was measured using OxiSelect® TBARS Assay Kit (MDA Quantitation; Cell Biolabs Inc, San Diego, Calif., USA).

Summary of In Vitro and In Vivo Screening Results

The in vitro profile of the compound of formula (I), as determined using the methods described above is presented below (Tables 5, 6 and 7). The compound of the present invention demonstrates potent inhibition of both PI3K δ and γ isoforms, and shows no inhibitory activity versus PI3K α and only low inhibitory activity versus PI3K β in enzyme assays (Table 5).

These effects translate into potent inhibition of Akt phosphorylation induced by the stimulation of cells with either hydrogen peroxide or MCP-1, No effects on cell viability, resulting from incubation with the compound of formula (I), were detected (Table 6). Furthermore treatment of cells with the compound of formula (I) disclosed herein was found to inhibit production of ROS from U937 cells and of cytokines from cytostim-challenged PBMCs (Table 7).

It is notable that the likely metabolic product of the compound of formula (I), namely corresponding alcohol, compound (Ia), is a significantly less active inhibitor of both PI3K δ and γ isoforms than the compound of formula (I) (Table 6). Consequently the compound of formula (Ia), is a significantly less active inhibitor of ROS production from U937 cells and of cytokines from cytostim-challenged PBMCs (Table 7) than the compound of formula (I).

TABLE 5

Comparison of the PI3K isoform inhibitory activities of prior art compounds with Compound (I).

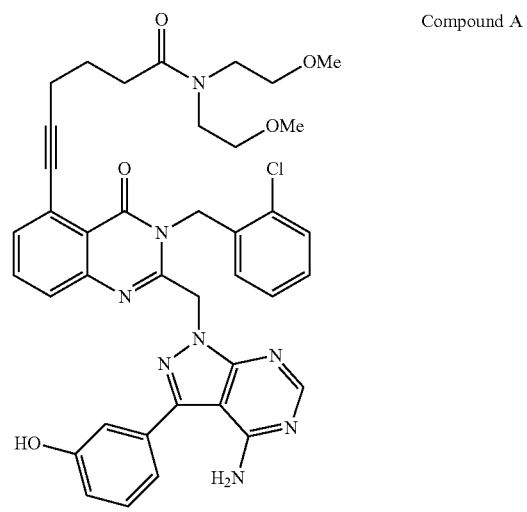

Compound A

TABLE 5-continued

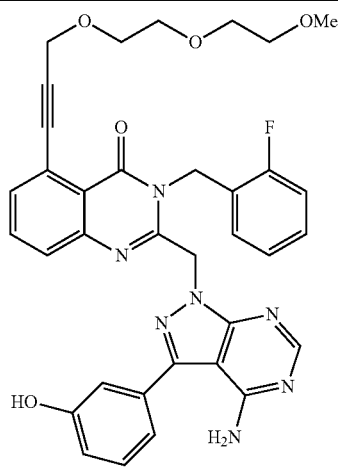

Example 50

| Test Compounds | IC$_{50}$ Values for PI3K inhibition at isozyme indicated (nM) | | | |
|---|---|---|---|---|
| | PI3K α | PI3K β | PI3K δ | PI3K γ |
| Compound (I) | >13900 | 4890 | 2.5 | 28 |
| Compound A[1] | 193 | NT | 12 | 25 |
| Example 50[2] | 653 | NT | 5.7 | 120 |

[1]Prior art compound disclosed in WO 2012/052753;
[2]Prior art compound disclosed in WO 2011/048111;
NT not tested;

TABLE 6

The inhibitory activity of compounds (I) and (Ia) on PI3K enzyme isoforms; the inhibition of inducd phosphylation of Akt in cells and on cell viability.

| Test Cmpd | PI3 Kinase Inhibition IC$_{50}$ value at isozyme (nM) | | | | Cellular Activity REC$_{50}$ values[a] in d-U937 cells (nM) | | Cell Viability MTT Assay[b] in d-U937 cells | |
|---|---|---|---|---|---|---|---|---|
| | δ | γ | α | β | H$_2$O$_2$ stim-ulus | MCP-1 stimulus | at 4 hr | at 24 hr |
| (I) | 2.5 | 28 | >13900 | 4890 | 7.4 | 16.5 | –ve | –ve |
| (Ia) | 17 | 577 | >14200 | >14200 | ND | ND | –ve | –ve |

[a]for the inhibition of induced Akt phosphorylation;
[b]–ve indicates a value of <30% inhibition at 10 μg/mL;
ND: not done

TABLE 7

The effects of the compounds of formula (I) and (Ia) on ROS production from U937 cells and cytokine release from PBMCs

| Cellular system | REC$_{50}$[1] or IC$_{50}$[2] value (nM) | |
|---|---|---|
| | Compound (I) | Compound (Ia) |
| Zymosan-induced Ros[a] production in IFNγ-primed U937 cells[1] | 11.8 | 143 |
| Cytostim-induced IL-4 in PBMCs[2] | <1.4 | 674 |
| Cytostim-induced IL-5 in PBMCs[2] | <1.4 | 14.5 |
| Cytostim-induced IL-13 in PBMCs[2] | <1.4 | 6.1 |

TABLE 7-continued

The effects of the compounds of formula (I) and (Ia) on ROS production from U937 cells and cytokine release from PBMCs

| Cellular system | REC$_{50}$[1] or IC$_{50}$[2] value (nM) | |
|---|---|---|
| | Compound (I) | Compound (Ia) |
| Cytostim-induced IFNγ in PBMCs[2] | 13.8 | 60.8 |
| THP1 cell chemotaxis to MCP1[1] | 33.9 | >14200 |
| TNFα-induced CXCL8 in neutrophils from COPD patients[1] | 2.2 | ND |

[a]ROS: reactive oxygen species.

The effects of treatment with compound (I) on LPS-induced airway neutrophilia in mice and rats are reported in Tables 8 and 9, respectively. Treatment was found to produce a dose-dependent inhibition of LPS-induced neutrophilia in both species. Furthermore, the inhibitory effects of treatment on cell accumulation were found to demonstrate a long duration of action.

TABLE 8

The Effects of Treatment with Compound (I) on LPS-induced airway neutrophilia in mice.

| Compound (I) | Neutrophil numbers in BALF (×10$^5$/mL, mean ± SEM) at pre-dose time indicated (% inhibition) | | |
|---|---|---|---|
| (mg/mL) | 2 hr | 8 hr | 12 h |
| Vehicle | 17.1 ± 2.5 | — | — |
| 0.05 | 13.8 ± 2.5 (19) | — | — |
| 0.2 | 8.0 ± 1.4 (53) | 9.4 ± 2.0 (45) | 13.1 ± 2.5 (23) |
| 1.0 | 5.5 ± 0.9 (68) | — | — |

N = 8 animals per group

TABLE 9

The Effects of Treatment with Compound (I) on LPS-Induced Airway Neutrophilia in Rats.

| Compound (I) | Neutrophil numbers in BALF (×10$^5$/mL, mean ± SEM) at pre-dose time indicated (% inhibition) | | |
|---|---|---|---|
| (mg/mL) | 2 hr | 8 hr | 12 h |
| Vehicle | 15.1 ± 2.6 | — | — |
| 0.05 | 13.2 ± 2.3 (9) | — | — |
| 0.2 | 6.3 ± 1.6 (58) | 10.1 ± 1.8 (33) | 13.6 ± 2.7 (10) |
| 1.0 | 4.1 ± 0.7 (73) | — | — |

N = 8 animals per group

The effects of treatment with compound (I) on allergen challenge-induced airway eosinophilia and neutrophilia in mice are reported in Table 10. Treatment of mice with the compound disclosed herein was found to produce a dose-dependent inhibition of both eosinophil and neutrophil accumulation in bronchoalveolar lavage following allergen challenge.

TABLE 10

The effects of treatment with Compound (I) on ovalbumin-induced airway eosinophilia and neutrophilia in ovalubumin sensitized mice.

| Compound (I) | Cell numbers in BALF ($\times 10^4$/mL, mean ± SEM) and (% inhibition) | |
|---|---|---|
| (mg/mL) | Eosinophils | Neutrophils |
| Vehicle | 24.7 ± 3.1 | 9.8 ± 0.6 |
| 0.05 | 19.7 ± 3.2 (20) | 8.0 ± 0.4 (18) |
| 0.2 | 3.8 ± 0.9 (85) | 2.9 ± 0.5 (70) |
| 1 | 2.1 ± 0.4 (91) | 2.0 ± 0.3 (80) |

N = 8 animals per group

Figure 1B:
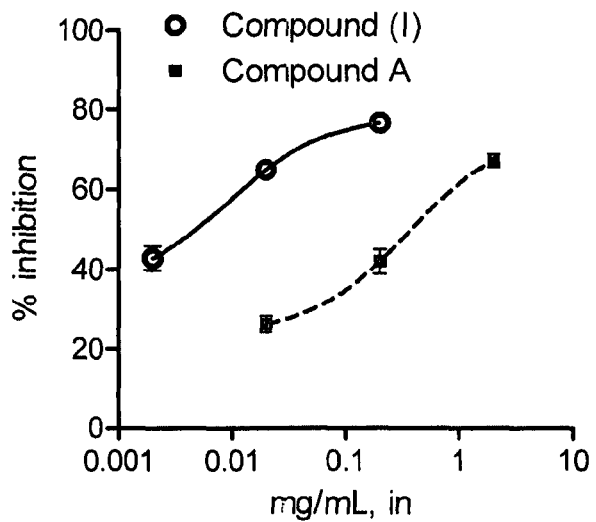
FIG. 1b: shows a comparison of the inhibitory potencies of compound (I) against compound A on poly-I:C-induced neutrophil accumulation in mouse airways

The effect of treatment with compound (I) or with compound A on macrophage and neutrophil accumulation in BALF following exposure of mice to poly-I:C was also investigated. In this direct comparison, treatment with either compound (I) or compound A was found to produce a dose-dependent inhibition of poly-I:C-induced macrophage and neutrophil accumulation into BALF (Table 11). It is notable that compound (I) shows significantly greater potency than compound A and this data is represented graphically for neutrophils (FIG. 1)

TABLE 11

The effects of treatment with Compound (I) or Compound A on poly-I:C-induced cell accumulation in mice airways.

| Treatment and dose of Compound (I) or Compound A | Cell numbers in BALF[a] ($\times 10^4$/mL) and (% inhibition) | |
|---|---|---|
| (mg/mL) | Macrophages | Neutrophils |
| Vehicle | 3.6 ± 0.2 | 1.4 ± 0.1 |
| Vehicle + Poly I:C | 19.0 ± 0.5 | 11.6 ± 0.2 |
| Compound (I) (0.002) + Poly I:C | 11.5 ± 0.2 (49) | 7.3 ± 0.3 (43) |
| Compound (I) (0.02) + Poly I:C | 8.3 ± 0.3 (69) | 5.0 ± 0.2 (65) |
| Compound (I) (0.2) + Poly I:C | 6.8 ± 0.2 (79) | 3.8 ± 0.2 (77) |
| Compound A (0.02) + Poly I:C | 14.3 ± 0.3 (31) | 8.9 ± 0.2 (26) |
| Compound A (0.2) + Poly I:C | 11.0 ± 0.4 (52) | 7.3 ± 0.3 (42) |
| Compound A (2) + Poly I:C | 7.8 ± 0.2 (73) | 4.8 ± 0.2 (67) |

[a]The data for cell numbers are shown as the mean ± SEM;
N = 5 animals per group

TABLE 12

The effect of treatment with Compound (I) ± fluticasone propionate on cigarette smoke (CS)-induced cell accumulation in murine BALF.

| Treatment and dose of Compound (I) (mg/mL) | Cell numbers in BAL[b] ($\times 10^4$/mL) and (% inhibition) | |
|---|---|---|
| | Macrophages | Neutrophils |
| Air + Vehicle | 4.5 ± 0.3 | 1.5 ± 0.2 |
| CS + Vehicle | 17.9 ± 0.6 | 11.1 ± 0.5 |
| CS + Compound (I) (0.02) | 13.6 ± 0.2 (32) | 8.6 ± 0.2 (26) |
| CS + Compound (I) (0.2) | 9.5 ± 0.2 (63) | 6.0 ± 0.1 (54) |
| CS + Compound (I) (2) | 7.4 ± 0.3 (79) | 4.6 ± 0.1 (68) |
| CS + Compound (I) (0.02) + FP[a] | 13.6 ± 0.4 (32) | 8.7 ± 0.2 (26) |
| CS + Compound (I) (0.2) + FP[a] | 9.4 ± 0.3 (63) | 5.8 ± 0.3 (55) |
| CS + Compound (I) (2) + FP[a] | 7.0 ± 0.3 (81) | 4.3 ± 0.2 (71) |

Figure 2A:
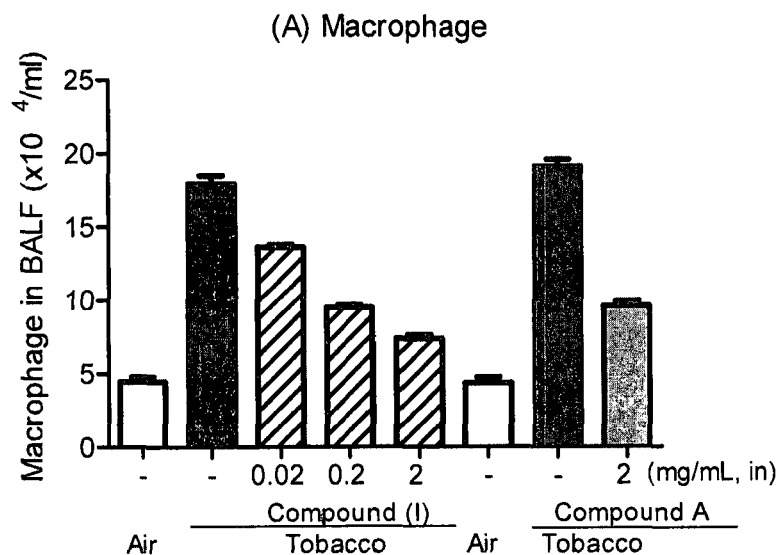
FIG. 2a: is a bar graph representing the effect of treatment with compound (I) or compound A on cigarette smoke-induced macrophage accumulation in murine BALF.
Figure 2B:
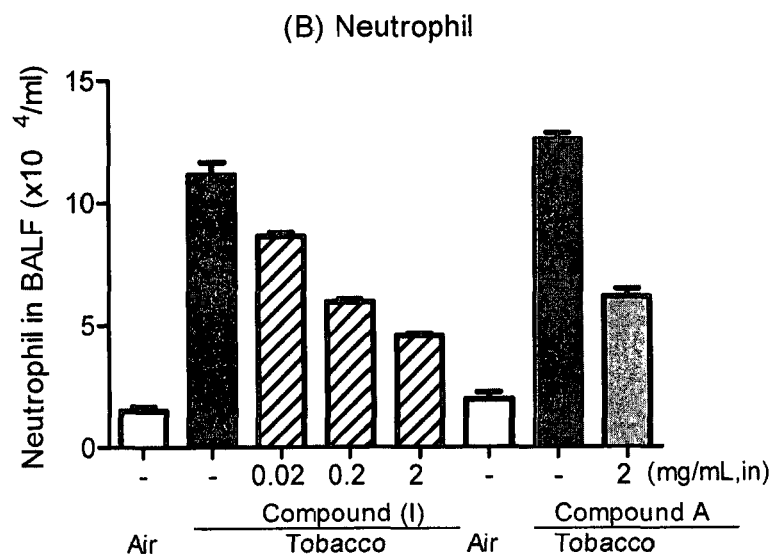
FIG. 2b: is a bar graph representing the effect of treatment with compound (I) or compound A on cigarette smoke-induced neutrophil accumulation in murine BALF.

N = 5 animals per group;
[a]FP = fluticasone propionate dosed at 50 µg/mL;
[b]The data for cell numbers are shown as the mean ± SEM, The effects of treatment with compound (I) on macrophage and neutrophil accumulation in BALF following exposure to cigarette smoke was determined (Table 12). The cigarette smoke model used for this study is reported to be a corticosteroid refractory system [To, Y. et al., *Am. J. Respir. Crit. Care Med.*, 2010, 182:897-904; Medicherla, S. et al., *J. Pharmacol. Exp. Ther.* 2008, 324:921-9] and the data reveal that dexamethasone (0.3-10 mg/kg, p.o.) was, as anticipated, inactive. The effects of treatment with compound (I) on BALF neutrophils and on activated alveolar macrophage numbers demonstrate that it possesses anti-inflammatory activity when administered as a monotherapy. Moreover, when compound (I) was co-administered with fluticasone propionate, at a dose which lacks any significant effect as monotherapy, a marked enhancement of anti-inflammatory activity was detected. In a contemporaneous study, the effects of treatment, with compound A, of mice exposed to cigarette-smoke were evaluated. A comparison of these data with those presented above for compound (I), demonstrates that compound (I) is a more potent inhibitor of cigarette-smoke induced cell accumulation in murine BALF than is compound A (FIG. 2).

Tobacco smoke exposure also increased the concentrations of the inflammatory biomarkers CXCL1, MCP1, TNFα, IL17, osteopontin and malondialdehyde in broncho-alveolar lavage fluid. Treatment with compound (I) decreased the concentrations of each of the biomarkers in a dose-dependent manner. Furthermore, treatment with both compound (I) and fluticasone propionate in combination showed greater decreases in biomarker concentrations than was achieved with treatment with compound (I) alone (Table 13).

TABLE 13

The effect of treatment with Compound (I) ± fluticasone propionate on biomarkers in murine BALF.

| Biomarker | Concentration of biomarker in BALF against treatment (pg/mL) | | Inhibition[1] (%) | | | | | |
|---|---|---|---|---|---|---|---|---|
| | | | Compound (I) (mg/mL) | | | Compound (I) (mg/mL) + FP[2] | | |
| | Air | Tobacco | 0.02 | 0.2 | 2 | 0.002 | 0.02 | 0.2 |
| CXCL1 | 8.4 ± 0.1 | 18 ± 0.3 | 32 | 52 | 71 | 32 | 58 | 77 |
| MCP-1 | 2.3 ± 0.2 | 7.2 ± 0.1 | 28 | 45 | 78 | 29 | 53 | 73 |
| TNF α | 1.5 ± 0.04 | 3.6 ± 0.1 | 22 | 38 | 62 | 22 | 39 | 64 |
| IL-17 | 1.2 ± 0.1 | 2.7 ± 0.1 | 27 | 41 | 60 | 26 | 51 | 67 |

TABLE 13-continued

The effect of treatment with Compound (I) ± fluticasone propionate on biomarkers in murine BALF.

| | Concentration of biomarker in BALF against treatment (pg/mL) | | Inhibition[1] (%) | | | | | |
|---|---|---|---|---|---|---|---|---|
| | | | Compound (I) (mg/mL) | | | Compound (I) (mg/mL) + FP[2] | | |
| Biomarker | Air | Tobacco | 0.02 | 0.2 | 2 | 0.002 | 0.02 | 0.2 |
| Osteopontin | 11 ± 0.3 | 23 ± 0.4 | 22 | 44 | 63 | 21 | 45 | 62 |
| MDA | 0.3 ± 0.02[3] | 1.6 ± 0.04[3] | 25 | 42 | 64 | 29 | 43 | 64 |

N = 5 animals per group;
[1]Percentage inhibition with respect to tobacco,
[2]fluticasone propionate (0.5 mg/mL);
[3]These data are are μM values; are smoke control after subtracted air control values In summary, the compound of the invention is a potent inhibitor of both PI3K δ and γ isoforms. The in vitro profile translates into a broad anti-inflammatory phenotype in vivo. In this setting, the inhibitory effects of the compound disclosed herein versus Poly I:C-induced cell accumulation in the airways is notable. It is also particularly striking that, unlike selective inhibitors of PI3K δ, treatment with compound (I) disclosed herein alone results in marked inhibition of cigarette-smoke induced airways inflammation and that these effects occur at lower doses when it is co-administered with a corticosteroid, fluticasone propionate, under conditions where treatment with the corticosteroid alone is without effect.

Example 15—Pharmaceutical Formulations Comprising Compound (I)

A composition of compound (I) may be formulated for a Dry Powder Inhaler as follows:

Compound (I) micronized by a suitable method such as an airjet mill to give a D50 value of approximately 2 μm and then is formulated in a blend with or without magnesium stearate. The blend is filled into unit dose containers (for example, capsules, blisters) for inhalation via a Dry Powder Inhaler. Examples of formulations are given containing between 0 and 1% magnesium stearate, with an example fill weight of 25 mg per dose and with a dose strength ranging from 1 to 1000 micrograms (mcg) per dose. Different strengths, different amounts of magnesium stearate and different fill weights per dose can also be used.

TABLE 14

Formulations containing 0% magnesium stearate

| | % w/w product strength mcg per dose | | | | | |
|---|---|---|---|---|---|---|
| Material | 1 | 5 | 25 | 100 | 250 | 1000 |
| Compound of formula (I) | 0.004 | 0.02 | 0.1 | 0.4 | 1 | 4 |
| Lactose for inhalation | 99.996 | 99.98 | 99.9 | 99.6 | 99.0 | 96.0 |

TABLE 15

Formulations containing 0.5% magnesium stearate

| | % w/w product strength in mcg per dose | | | | | |
|---|---|---|---|---|---|---|
| Material | 1 | 5 | 25 | 100 | 250 | 1000 |
| Compound of formula (I) | 0.004 | 0.02 | 0.1 | 0.4 | 1 | 4 |
| Magnesium stearate | 0.5 | 0.5 | 0.5 | 0.5 | 0.5 | 0.5 |
| Lactose for inhalation | 99.496 | 99.48 | 99.4 | 99.1 | 98.5 | 95.5 |

TABLE 16

Formulations containing 1% magnesium stearate

| | % w/w product strength mcg per dose | | | | | |
|---|---|---|---|---|---|---|
| Material | 1 | 5 | 25 | 100 | 250 | 1000 |
| Compound of formula (I) | 0.004 | 0.02 | 0.1 | 0.4 | 1 | 4 |
| Magnesium stearate | 1 | 1 | 1 | 1 | 1 | 1 |
| Lactose for inhalation | 98.996 | 98.98 | 98.9 | 98.6 | 98.0 | 95.0 |

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A crystalline form of a compound of formula (I)

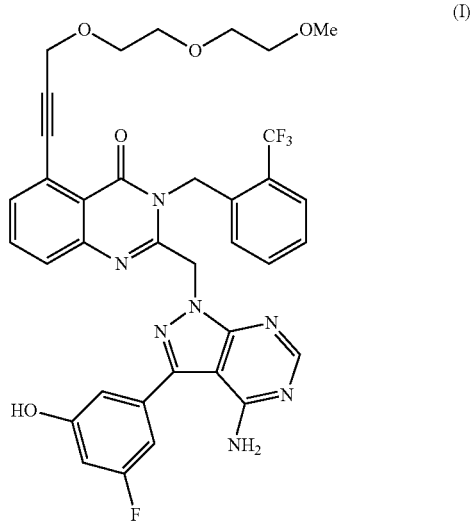 [SMILES: COCCOCCOCC#Cc1cccc2nc(Cn3nc(-c4cc(O)cc(F)c4)c4c(N)ncnc43)n(Cc3ccccc3C(F)(F)F)c(=O)c12]

or a pharmaceutically acceptable salt thereof.

2. The crystalline form of claim 1, wherein the crystalline form is the Form 2 crystalline polymorph.

3. The crystalline form of claim 1, wherein the crystalline form is the Form 3 crystalline polymorph.

4. A pharmaceutical composition comprising the crystalline form of claim 1 in combination with one or more pharmaceutically acceptable diluents or carriers.

5. A pharmaceutical composition according to claim 4 further comprising a second or further active ingredient selected from the group consisting of corticosteroids, beta agonists, xanthines, muscarinic antagonists and p38 MAP kinase inhibitors.

6. A combination product comprising:
   (A) the crystalline form of claim 1; and
   (B) a further active ingredient selected from the group consisting of corticosteroids, beta agonists, xanthines, muscarinic antagonists, phosphodiesterase inhibitors and p38 MAP kinase inhibitors;
   wherein each of components (A) and (B) is formulated in admixture with a pharmaceutically-acceptable diluent or carrier.

7. A method of treatment of an inflammatory condition of the lungs comprising administering to a subject an effective amount of the crystalline form of claim 1.

8. A compound of formula (I):

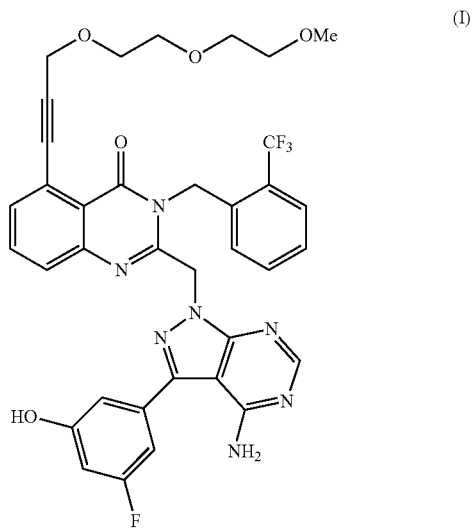 [SMILES: COCCOCCOCC#Cc1cccc2nc(Cn3nc(-c4cc(O)cc(F)c4)c4c(N)ncnc43)n(Cc3ccccc3C(F)(F)F)c(=O)c12]

in the form of its Form 2 crystalline polymorph having an XRPD pattern substantially as shown in FIG. 5.

9. A compound of formula (I)

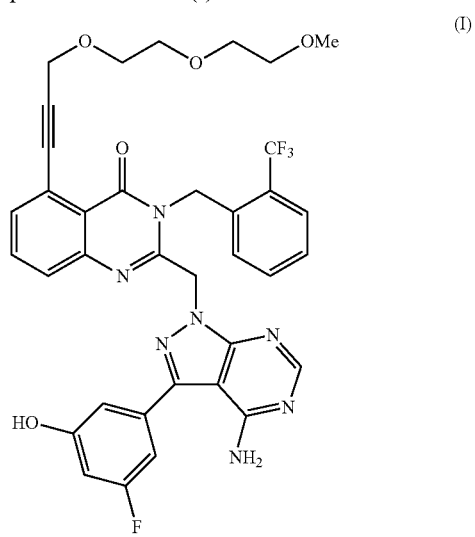

in the form of its Form 2 crystalline polymorph having an XRPD pattern containing three, four, five, six, seven, eight, nine, ten, eleven, twelve, thirteen, fourteen, fifteen, sixteen, seventeen, eighteen, nineteen, twenty or twenty one peaks at positions selected from the group consisting of 8.2, 9.0, 9.2, 9.7, 12.2, 14.1, 14.3, 15.0, 16.4, 18.0, 18.5, 19.0, 19.6, 21.8, 22.3, 22.5, 24.3, 24.5, 24.8, 25.1 and 25.8 (±0.2 degrees, 2-theta values).

10. A compound of formula (I) according to claim 9 having an XRPD pattern containing one, two, three or four peaks at positions selected from the group consisting of 9.7, 12.2, 14.1 and 14.3 (±0.2 degrees, 2-theta values).

11. A method of treatment of an inflammatory condition of the lungs comprising administering to a subject a pharmaceutical composition according to claim 5.

12. A method of treatment of an inflammatory condition of the lungs comprising administering to a subject a combination product according to claim 6.

13. A method of preparing the crystalline form of claim 1, comprising contacting compound (I)

with a solvent selected from the group consisting of methanol, ethanol, 2-propanol, 1-propanol, acetone, ethyl acetate, acetonitrile, toluene, isopropylacetate, TBME, 2-butanone, DMSO, diethyl ether, MIBK, heptane, nitromethane, 10% water/ethanol, 10% water/acetonitrile and 10% water/2-propanol.

14. The pharmaceutical composition of claim 4, wherein the crystalline form is micronized.

15. The pharmaceutical composition of claim 4, wherein the pharmaceutically acceptable diluent or carrier comprises lactose and magnesium stearate.

* * * * *